(12) United States Patent
Guo et al.

(10) Patent No.: US 9,274,105 B2
(45) Date of Patent: Mar. 1, 2016

(54) ANALYZING CHEMICAL AND BIOLOGICAL SUBSTANCES USING NANO-STRUCTURE BASED SPECTRAL SENSING

(71) Applicant: OptoTrace (Suzhou) Technologies, Inc., SuZhou (CN)

(72) Inventors: Xun Guo, San Jose, CA (US); Chunwei Liu, Beijing (CN); Anping Deng, SuZhou (CN); Huafang Chang, SuZhou (CN); Hong Wang, Cupertino, CA (US)

(73) Assignee: Optrotrace (SuZhou) Technologies, Inc., Suzhou (CN)

( * ) Notice: Subject to any disclaimer, the term of this patent is extended or adjusted under 35 U.S.C. 154(b) by 477 days.

(21) Appl. No.: 13/724,619

(22) Filed: Dec. 21, 2012

(65) Prior Publication Data

US 2013/0115717 A1   May 9, 2013

Related U.S. Application Data

(63) Continuation-in-part of application No. 13/442,835, filed on Apr. 9, 2012, now Pat. No. 8,699,019.

(60) Provisional application No. 61/507,592, filed on Jul. 13, 2011.

(51) Int. Cl.
| | |
|---|---|
| *G01N 33/558* | (2006.01) |
| *G01N 33/543* | (2006.01) |
| *B82Y 30/00* | (2011.01) |
| *B82Y 5/00* | (2011.01) |

(52) U.S. Cl.
CPC .......... *G01N 33/54346* (2013.01); *B82Y 30/00* (2013.01); *B82Y 5/00* (2013.01)

(58) Field of Classification Search
CPC .................... G01N 21/658; G01N 2015/0088; G01N 2021/6439; G01N 2021/656; G01N 27/3278; C12Q 2565/632; G01J 3/44; B01J 2219/00605
See application file for complete search history.

(56) References Cited

U.S. PATENT DOCUMENTS

| | | | |
|---|---|---|---|
| 4,933,274 A | 6/1990 | Sanford | |
| 5,017,007 A | 5/1991 | Milne | |
| 5,244,788 A | 9/1993 | Hubscher | |

(Continued)

FOREIGN PATENT DOCUMENTS

CN          102168072 B   *   8/2011

OTHER PUBLICATIONS

Translated Chinese patent CN 102168072 B, Gao et al.*

*Primary Examiner* — Chris L Chin
(74) *Attorney, Agent, or Firm* — SV Patent Service

(57) ABSTRACT

An integrated chromatography-immunoassay system for integrated chromatography-immunoassay system includes a chromatographic unit that receives labeled nano-structured probes comprising nano particles and antibodies attached to the nano particles, and a test membrane comprising coating antigens. The chromatographic unit allows the labeled nano-structured probes to diffuse there through and into the test membrane, wherein the antibodies on the nano particles are bound to the coating antigens. A laser device emits a laser light to illuminate the labeled nano-structured probes having the antibodies bound to the coating antigens on the test membrane. A spectral analyzer obtains a Raman spectrum from light scattered from the labeled nano-structured probes having the antibodies bound to the coating antigens on the test membrane, and to identify a spectral signature in the Raman spectrum associated with the antibody-antigen pair, which enables detection and identification of the antibody.

13 Claims, 50 Drawing Sheets

(56) References Cited

U.S. PATENT DOCUMENTS

| | | |
|---|---|---|
| 5,527,712 A | 6/1996 | Sheehy |
| 5,864,397 A | 1/1999 | Vo-Dinh |
| 6,361,861 B2 | 3/2002 | Gao |
| 6,406,777 B1 | 6/2002 | Boss |
| 6,614,523 B1 | 9/2003 | Boss |
| 7,355,703 B2 * | 4/2008 | Mondello ............. G01N 21/65 356/301 |
| 7,518,721 B2 * | 4/2009 | Burrell ................. G01N 21/65 356/301 |
| 7,688,440 B2 * | 3/2010 | Clarke ................. G01N 21/65 356/301 |
| 2002/0045195 A1 * | 4/2002 | Hubscher et al. ............. 435/7.9 |
| 2002/0123050 A1 | 9/2002 | Poponin |
| 2002/0146844 A1 * | 10/2002 | Pronovost et al. ............ 436/514 |
| 2003/0059820 A1 | 3/2003 | Vo-Dinh |
| 2003/0175472 A1 | 9/2003 | Den |
| 2004/0106203 A1 | 6/2004 | Stasiak |
| 2005/0136552 A1 | 6/2005 | Buechler |
| 2008/0064120 A1 * | 3/2008 | Clarke ................. G01N 21/658 436/514 |
| 2009/0325318 A1 * | 12/2009 | Carron .......................... 436/526 |
| 2010/0055721 A1 * | 3/2010 | Lambert ................. B82Y 5/00 435/7.33 |

* cited by examiner

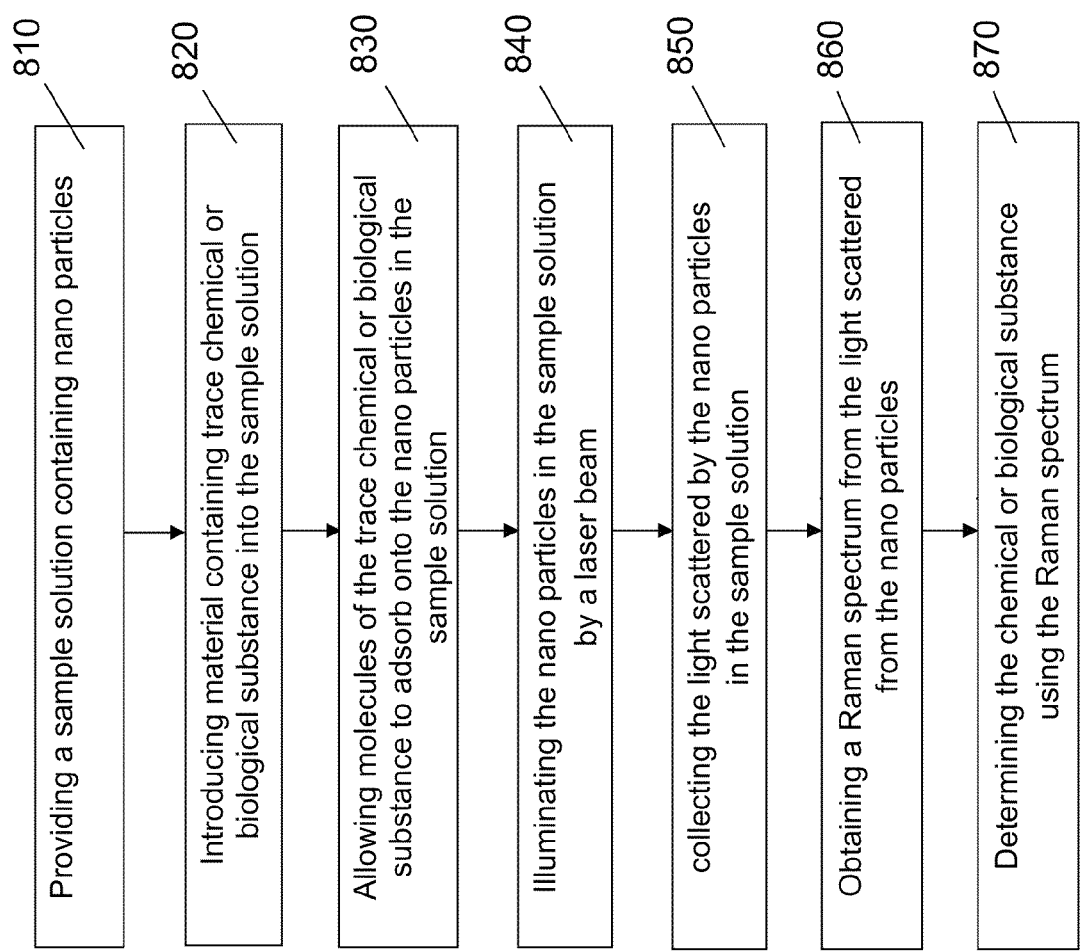

SECTION A-A

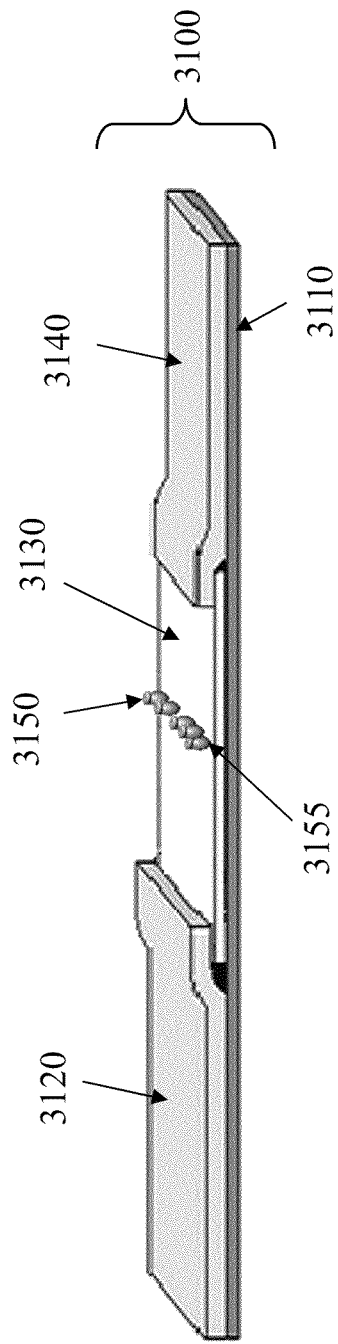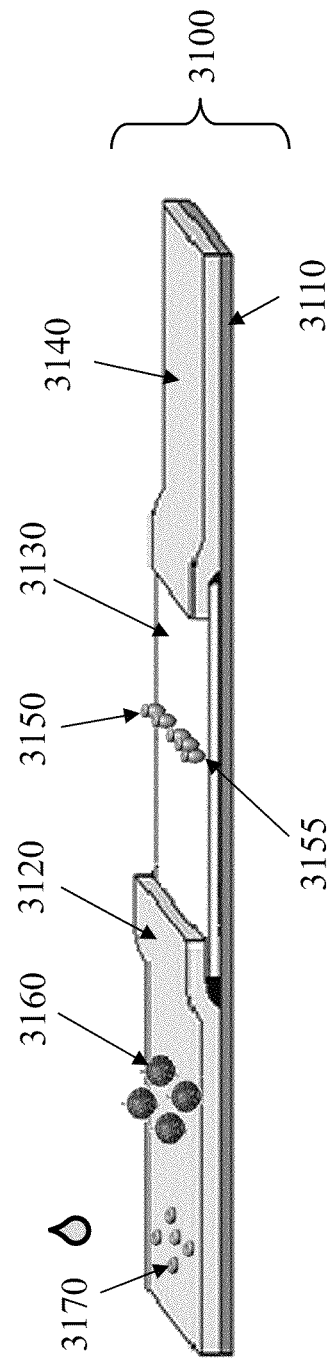
Fig. 30A
Fig. 30B

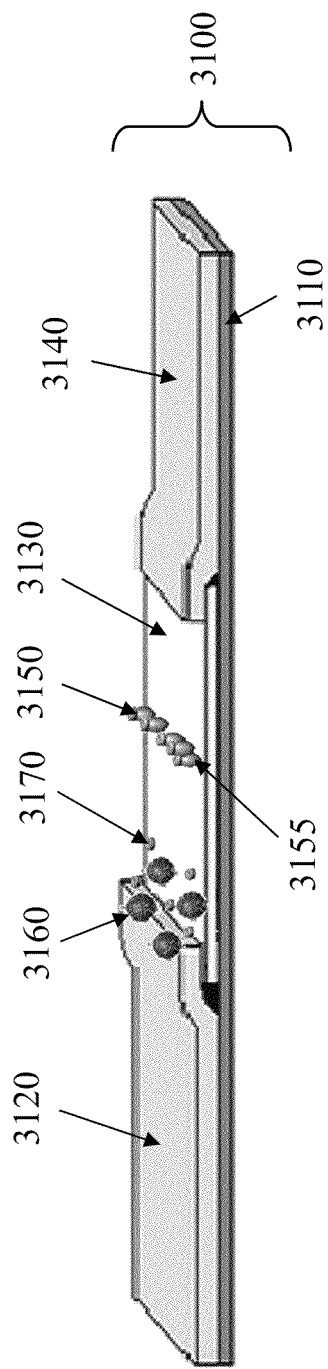
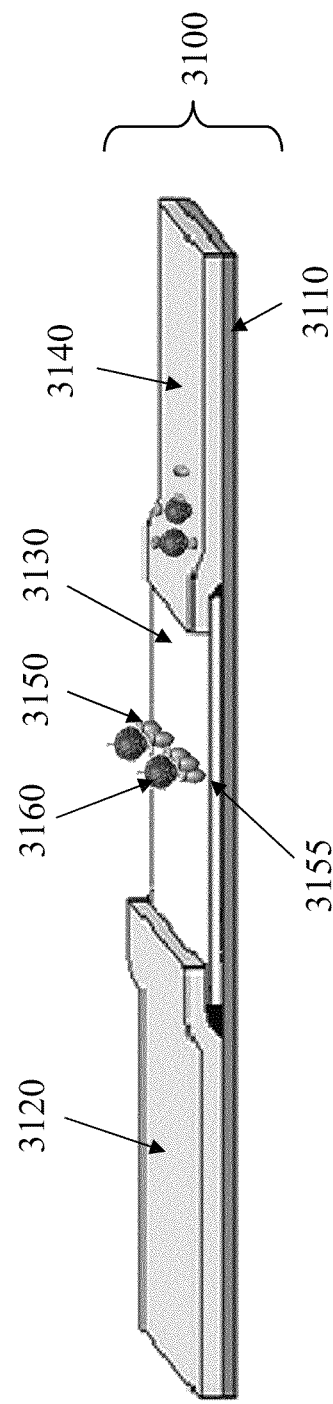
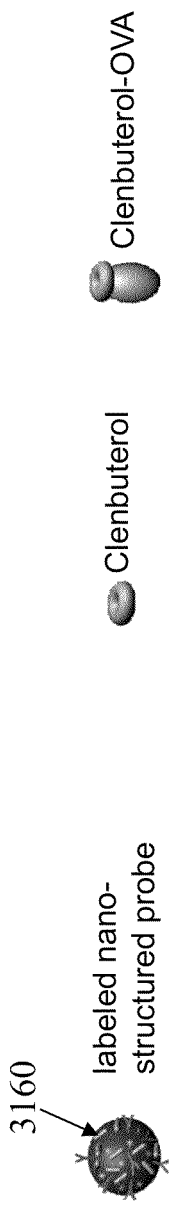
Fig. 31A
Fig. 31B
Fig. 32

ANALYZING CHEMICAL AND BIOLOGICAL SUBSTANCES USING NANO-STRUCTURE BASED SPECTRAL SENSING

The present application is a continuation application of and claims priority to commonly assigned pending U.S. patent application Ser. No. 13/442,835, entitled "Assuring food safety using nano-structure based spectral sensing" filed Apr. 9, 2012. U.S. patent application Ser. No. 13/442,835 claims priority to U.S. Provisional Patent Application 61/507,592, entitled "Analyzing chemical and biological substances using nano-structure based spectral sensing" filed Jul. 13, 2011. The disclosures of the above patent applications are incorporated herein by reference.

BACKGROUND OF THE INVENTION

The present invention generally relates to detection of chemical, biological, radioactive, and other substances by a light scattering probe and a chemical sensor.

Light scattering techniques such as Raman spectroscopy are known to be capable of identifying chemicals and biological agents. A major limitation associated with Raman spectroscopy is that the Raman scattering signals from chemicals and biological agents tend to be very weak. Although many attempts have been made to increase Raman scattering intensity, such efforts have not yielded practical and economical detectors based on Raman spectroscopy. As a result, Raman scattering so far only has very limited applications in sensing chemicals and biological agents.

A need therefore exists for effective and practical Raman spectroscopy based detectors for trace amount of chemical, biological, radioactive, and other substances.

SUMMARY OF THE INVENTION

The present application discloses Raman spectral sensing systems and methods that are capable of detecting biological or chemical substance at ultra-high sensitivity. The disclosed Raman spectral sensing systems and methods can detect biological or chemical substances at concentration levels a several orders of magnitude lower than those in the conventional sensing techniques. The biological and chemical substances include antigens, antibodies, and a wide range of small molecules and metallic elements. Specifically, when applied to biological immunoassay, detection sensitivity and specificity can be significantly enhanced.

In one general aspect, the present invention relates to an integrated chromatography-immunoassay system that includes a chromatographic unit that can receive labeled nano-structured probes comprising nano particles and antibodies attached to the nano particles and a test membrane comprising coating antigens, wherein the chromatographic unit can allow the labeled nano-structured probes to diffuse there through and into the test membrane, wherein the antibodies on the nano particles are bound to the coating antigens. The integrated chromatography-immunoassay system also includes a laser device that can emit a laser light to illuminate the labeled nano-structured probes having the antibodies bound to the coating antigens on the test membrane, and a spectral analyzer that can obtain a Raman spectrum from light scattered from the labeled nano-structured probes having the antibodies bound to the coating antigens on the test membrane, and to identify a spectral signature in the Raman spectrum associated with the antibody-antigen pair, which enables detection and identification of the antibody.

Implementations of the system may include one or more of the following. The chromatographic unit can receive a competitive antigen and to allow the competitive antigen to diffuse there through and into the test membrane, wherein the competitive antigen competes with the coating antigens to bind to the antibodies on the nano particles. The labeled nano-structured probes can include a spectral marker attached to the nano particles or the antibodies. The antigen can include clenbuterol, nitrofurans, organic phosphorus, organochlorine, pro terephthalate, a pesticide, a rodenticide, or a veterinary drug. The antigen can include melamine, sodium cyclamate, sodium cyclohexylsulfamate, cane sugar, starch, Sudan I, II, III and IV, malachite green, methomidophos, acephate, DDT, DDV, malathion, fenitrothion, deltamethrin, cypermethrin, methyl parathion, phosmet, dimethoate, nitrofuran, furanzolidole, chloramphenicol, chlortetracycline, ciprofloxacin, clenbuterol, or enorfloxacin. The nano particles can have an average diameter in a range from 10 nm and 100 nm. The nano particles can include a material selected from a group consisting of a metal, a metal alloy, an oxide material, silicon, a polymeric material, a magnetic or ferromagnetic material, and a combination thereof, or a material selected from a group consisting of Al, Ag, Au, Cu, Fe, Co, Ni, Cr, Zn, Sn, Pd, Pt, and a combination thereof. The coating antigens can include clenbuterol, wherein the clenbuterol is bound to an OVA molecule to form an OVA-clenbuterol complex, the OVA-clenbuterol complex bound to the test membrane.

In another general aspect, the present invention relates to a method for a method for substance identification. The method includes allowing an antibody to be adsorbed to a nano surface structure, introducing an unknown antigen to the nano surface structure to allow the unknown antigen to bind with antibody on the nano surface structure, illuminating, by a laser beam, the bound unknown antigen and antibody on the nano surface structure, collecting light scattered by the bound unknown antigen and antibody on the nano surface structure, obtaining a Raman spectrum from the light scattered by the bound unknown antigen and antibody on the nano surface structure, finding a spectral signature associated with the bound unknown antigen and antibody in the Raman spectrum, and identifying the unknown antigen as an antigen that matches the antibody on the nano surface structure based on the spectral signature.

Implementations of the system may include one or more of the following. The antigen can be selected from the group consisting of clenbuterol, nitrofurans, organic phosphorus, organochlorine, pro terephthalate, a pesticide, a rodenticide, a substance in a veterinary drug, an arsenic compound, and a cyanide. The antigen can be selected from the group consisting of melamine, sodium cyclamate, sodium cyclohexylsulfamate, cane sugar, starch, nitrite, nitrate, Sudan I, II, III and IV, malachite green, methomidophos, acephate, DDT, DDV, malathion, fenitrothion, deltamethrin, cypermethrin, methyl parathion, phosmet, dimethoate, nitrofuran, furanzolidole, chloramphenicol, chlortetracycline, ciprofloxacin, clenbuterol, and enorfloxacin. The method can further include diagnosing a disease in the person based on the identification of the unknown antigen associated with the disease. The reagent can include a body fluid obtained from a person. The disease can be selected from the group consisting of a cancer, asthma, allergy, liver cirrhosis, a failing kidney, leukemia, Alzheimer's disease, Parkinson disease, diabetes, smoking addiction, arthritis, a cardiovascular disease, SARS, a flu, and human immunodeficiency virus (HIV). The unknown antigen can include an illicit drug substance selected from a group consisting of heroin, methamphetamine, cocaine, caffeine, morphine, codeine, amphetamine, ephedrine, papaverine, narcotine, Ketamine, and MDMA. The unknown antigen can include a protein carrier and the molecule of an unknown substance bound to the protein carrier, wherein the identification of the protein carrier leads to the identification of the unknown substance. The unknown substance can include Ketamine or fluoroacetamide. The unknown antigen can be extracted from a food product. The method can further include applying an electrical field, a magnetic field, or an electro-magnetic field to the nano surface structures when the light scattered by each of the nano surface structures is collected. The nano surface structure can include nano particles having an average dimension in a range from about 1 nm to about 1000 nm. The nano particles can include a material selected from a group consisting of a metal, a metal alloy, an oxide material, silicon, a polymeric material, a magnetic or ferromagnetic material, and a combination thereof, or a material selected from a group consisting of Al, Ag, Au, Cu, Fe, Co, Ni, Cr, Zn, Sn, Pd, Pt, and a combination thereof. The nano surface structure can be formed on a substrate. The nano surface structures comprise protrusions or columns formed on an upper surface of the substrate, wherein the neighboring protrusions or columns have average distances in a range from 10 nanometers to 1000 nanometers. The nano surface structures can include recesses or holes formed in an upper surface of the substrate. The neighboring recesses or holes can have average distances in a range from 10 nanometers to 1000 nanometers.

In another general aspect, the present invention relates to a method for a method for substance identification. The method includes applying a pre-treatment chemical or biological material to a nano surface structure; introducing a reagent containing an unknown substance to the nano surface structure to allow molecules of the unknown substance to adsorb to the nano surface structure with the assistance of the pre-treatment chemical or biological material; illuminating the nano surface structure adsorbed with molecules of the unknown substance by a laser beam; collecting light scattered by the nano surface structure adsorbed with molecules of the unknown substance; obtaining a Raman spectrum from the light scattered by the nano surface adsorbed with molecules of the unknown substance; finding a spectral signature associated with the unknown substance in the Raman spectra; and identifying the unknown substance in the reagent using the spectral signature.

Implementations of the system may include one or more of the following. The antigen can include a protein carrier and the molecule of an unknown substance bound to the protein carrier. The method can further include identifying the protein carrier based on the spectral signature, wherein the unknown substance is identified based on the identification of the protein carrier. The unknown substance can include Ketamine or fluoroacetamide. The pre-treatment chemical or biological material can include an antibody that can adsorb to the surfaces of the nano surface structure, wherein the unknown substance is an antigen that matches the antibody, wherein the spectral signature is associated with antigen-antibody pair adsorbed to the nano surface structure. The pre-treatment chemical or biological material can include an antigen that can adsorb to the surfaces of the nano surface structure, wherein the unknown substance is an antibody that matches the antigen, wherein the spectral signature is associated with antigen-antibody pair adsorbed to the nano surface structure. The nano surface structures can include nano particles having an average dimension in a range from about 1 nm to about 1000 nm, or nano structures formed on a substrate.

BRIEF DESCRIPTION OF THE DRAWINGS

The following drawings, which are incorporated in and from a part of the specification, illustrate embodiments of the present invention and, together with the description, serve to explain the principles of the invention.

FIG. 8 is flow diagram for detecting trace chemical or biological substance using a solution containing nano particles and a light scattering probe.

FIG. 30A-31B illustrate an integrated chromatography-immunoassay system configured for nano-structured based light scattering substance detection.

FIG. 32 illustrates symbols of nano-structured probe and exemplified antigen and coating antigen used in FIGS. 30A-31B.

DETAILED DESCRIPTION OF THE INVENTION

Figure 1:
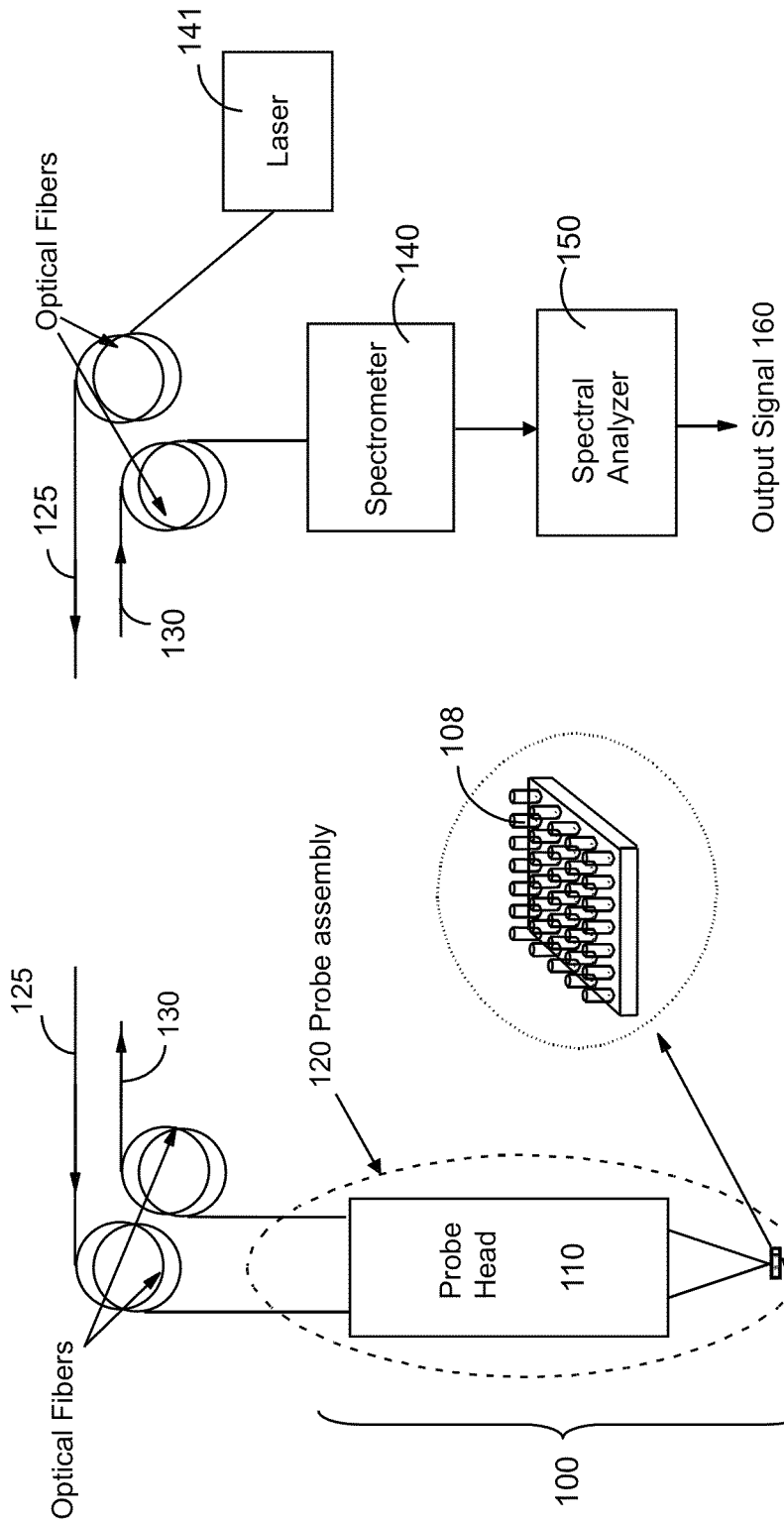
FIGS. 1A-1C illustrate an exemplified system for detection of chemical and biological substances using a Raman Scattering probe.

FIGS. 1A-1C respectively illustrate a system for detecting trace chemical or biological substances using surface-enhance Raman scattering. Referring to FIG. 1A, a light scattering probe 100 includes a probe head 110, and a sensor 105 positioned adjacent to the probe head 110. The sensor 105 includes a nano surface structure. For example, the nano surface structure can include a plurality of nano rods 108 (shown FIG. 1B), a plurality of nano holes, a cluster of nano particles in solution, or other surface structures having dimensions at nanometer scale. In some embodiments, as described below, a nano structured surface structures can be prepared by coating the surface of the sensor 105 of a solution containing a colloidal suspension of nano particles. The solution can be subsequently evaporated to deposit the nano particles on the surface. In the present specification, the term "nano particle" refers to a particle having at least in one dimension with a size smaller than 1,000 nm.

In some embodiments, a sample fluid can be introduced to the nano rods 108 in the sensor 105. The sample fluid can include a body fluid obtained from a patient or an illicit drug user for disease diagnosis and drug use determination, or a fluid of gas phase. Examples of the body fluid include blood, saliva, urine, serum, tear, sweat, stomach fluid, hydrothorax, ascites, CSF, sperm, and a secrete body fluid. The sample fluid can also comprise a food sample for detecting harmful or illegal additives in a food product to ensure food safety. Examples of food products include dairy products such as milk, milk powder, baby formula, cheese, yogurt, ice cream, milk-containing food products such as milk-containing candies, cake and cookies, and protein-containing food products. The probe head 110 and the sensor 105 can be enclosed in a probe assembly 120. The probe assembly 120 can be depressurized by a vacuum pump to reduce the contamination of the sensing surfaces by foreign substances.

A laser beam emitted by a laser 141 is guided by an optical fiber 125, as shown in FIG. 1C, to the probed head and to illuminate the nano surface structure on the sensor 105 (FIG. 1A). The light scattered by the sample solution on the nanosurface of the sensor 105 is collected by the probe head 110 and guided to a spectrometer 140 by an optical fiber 130. A Raman spectrum of the scattered light is obtained by a spectral analyzer 150 using the output of the spectrometer 140. One or more spectral signatures in the Raman spectrum are identified and compared with predetermined spectral signatures for various molecules. An output signal 160 indicates identification of a target molecule, for example, a harmful materials in food or water, dangerous materials (explosive or flammable materials), or disease related molecules, when a threshold of certain molecules under detection is exceeded. In the present specification, the term "spectral signature" refers to one or more spectral peaks, one or more spectral valleys, and other spectral shapes such as relative peak height, peak line width, and peak shape which can be used to characterize one or more molecular bonds in a biological, medical, or chemical substance.

In some embodiment, the sensor 105 can include various nano structures on sensors as disclosed in the commonly assigned pending U.S. patent application Ser. No. 12/014,800, titled "Optical sensing system on a micro-array structure", filed Jan. 26, 2008, the content of which is incorporated herein by reference. The optical sensing system that includes an optical sensor that includes a substrate having an upper surface and a plurality of tapered walls on the substrate, wherein at least one of the tapered walls is aligned along an longitudinal direction, wherein the plurality of tapered walls comprise sloped surfaces oriented at oblique angles relative to the upper surface, wherein the sloped surfaces are configured to adsorb molecules of a chemical sample; a light source configured to emit an incident light beam to impinge the plurality of tapered walls adsorbed with molecules of the chemical sample; and a detector that can collect light scattered by the plurality of tapered walls to allow a determination of the sample chemical.

The sensor 105 can also include a substrate having an upper surface and a plurality of tapered walls on the substrate, wherein the plurality of tapered walls comprise sloped surfaces oriented at oblique angles relative to the upper surface of the substrate, wherein at least two adjacent tapered walls define therein an air gap having a width that varies as a function of a distance from the upper surface; a light source configured to emit an incident light beam to impinge the plurality of tapered walls adsorbed with molecules of a chemical sample; and a detector that can collect light scattered by the plurality of tapered walls to allow a determination of the sample chemical.

In some embodiment, the sensor 105 can include multi-layer nano structures such as multi-layer nano rods and multi-layer nano holes as disclosed in the commonly assigned pending U.S. patent application Ser. No. 11/754,912, titled "Light scattering device having multi-layer micro structure", filed May 29, 2007, nano particle clusters or groups, or multi-layer nano particles in a solution, the content of which is incorporated herein by reference. The nano surface structure can include a silicon substrate; an adhesion layer on the silicon substrate; a bias layer on the adhesion layer; and one or more structure layers on the adhesion layer. The one or more structure layers can include different material compositions and a plurality of holes through at least two of the two or more of structure layers. The widths of the plurality of holes can be in the range of 0.5-1,000 nm. The nano surface structure can also include a silicon substrate; an adhesion layer on the silicon substrate; a bias layer on the adhesion layer; and a plurality of columns on the bias layer. At least one of the plurality of columns or holes can include two or more structure layers having different material compositions and have widths in the range of in the range of 0.5-1,000 nm.

Figure 2:
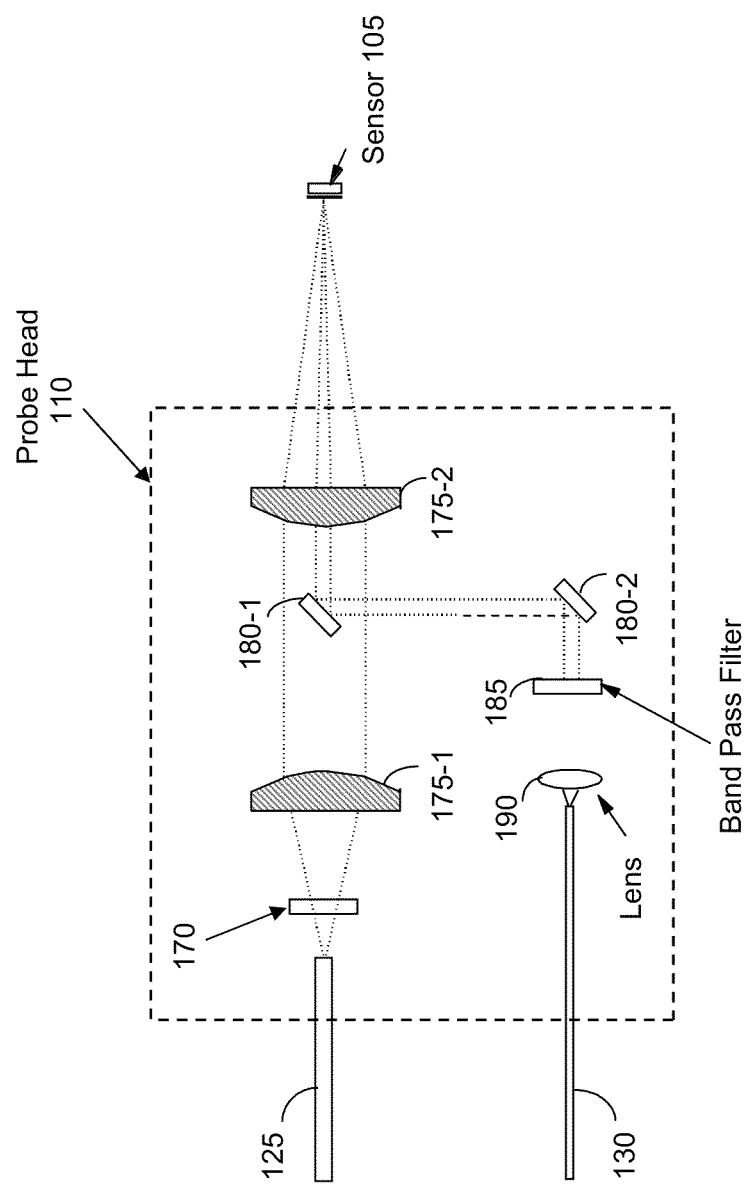
FIG. 2 illustrates an exemplified probe head for a Raman scattering probe compatible with FIGS. 1A-1C.

Referring to FIG. 2, the probe head 110 receives a laser beam from an input optical fiber 125. The laser beam passes through a band ejection filter 170 and lenses 175-1 and 175-2 to project onto the sensor 105. A scattering light from the sensor 105 is directed by a group of mirrors 180-1 and 180-2 to pass through another band-pass filter 185 and further collimated by a collimating lens 190 to enter the collection optical fiber 130.

The trace chemicals or biological agents to be detected can be provided in the form of a gas, a liquid, a solid, a sol gel, or an aerosol. The molecules are adsorbed onto the nano surface or nano particles of the sensor 105. Such adsorbed molecules have much larger scattering cross section under laser beam illustration than that they are in free form in a gas, a liquid, a solid, a sol gel, or an aerosol. When a laser beam illuminates the adsorbed molecules, Raman scattering spectrum of the molecules can be obtained. Target chemicals or biological agents can be identified using predetermined Raman spectral signatures for the molecules.

Figure 3A:
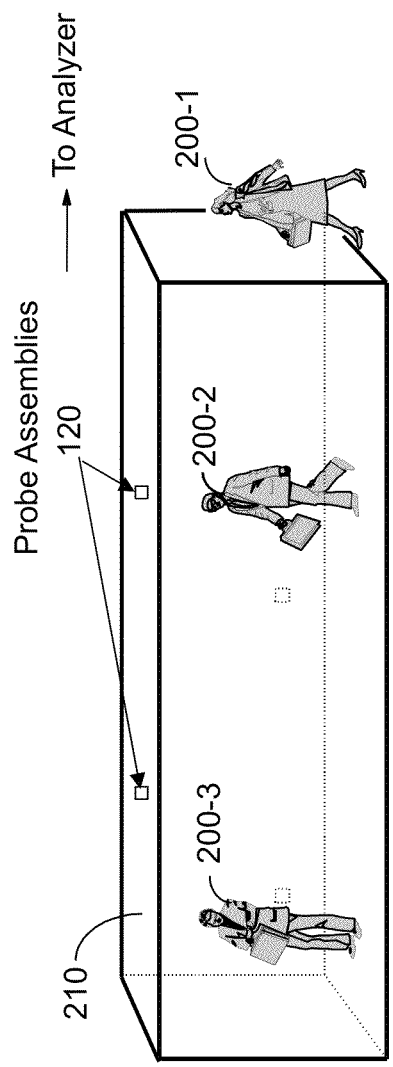
FIGS. 3A and 3B are schematic diagrams respectively showing inspections of passengers and luggage using a Raman scattering probe at an airport.

FIG. 3A shows an exemplified application of Surface-Enhance Raman Scattering in the area of transportation safety. Passengers 200-1, 200-2, and 200-3 walking through a passageway tunnel 210 are screened. One or more probe assemblies 120 with embedded sensor 105 are placed in the passageway tunnel 210. The probe assemblies 120 can be connected by fibers to a spectral analyzer 150 in a nearby or remote office. In each probe assembly 120, a probe head and a sensor are packaged together. The probe head is aligned to point to the sensing surface of a sensor 105. The passageway tunnel 210 can be forced ventilated and under little negative pressure and/or little higher temperature to increase evaporation of harmful materials. If a passenger (e.g., the passenger 200-2) carries an explosive material, a harmful chemical, a chemical weapon, a flammable liquid, a biochemical weapon, a nuclear weapon or a narcotic drug, a trace amount of such materials will volatilize into air such that molecules of the material can be adsorbed onto the surface of a sensor through a specially designed sample collection system (a detailed example is disclosed in the above referenced and commonly assigned U.S. Pat. No. 7,384,792). The Raman Spectra can be recorded and compared with the spectral signatures of known substances stored at a database at a central office. As soon as the harmful materials are detected, an alarm signal will be triggered. Appropriate security responses will be activated.

Figure 3B:
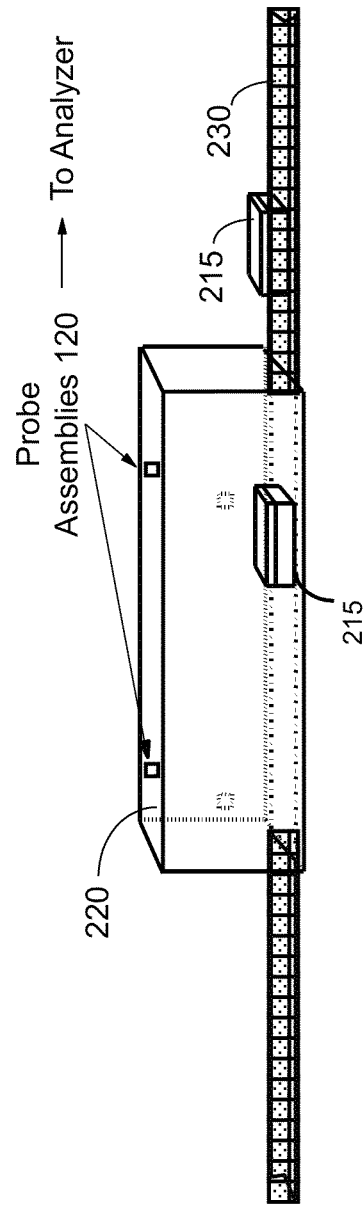

Referring to FIG. 3B, cargos 215 for freight transportation are carried by a conveyer 230 to pass through cargo screening channel 220. Probe assemblies 120 each embedded with a sensor 105 are placed around the cargo screen channel 220. The probe assemblies 120 can be connected with fibers to the spectral analyzer 150 in office near or far away from it. The probe assembly 120 is aligned to the surface of a sensor 105 and they are packaged together to detect any explosives, chemical or biochemical weapon, or harmful chemicals enclosed in the luggage 215. This configuration can be implemented in other applications such as checked-in luggage for passenger air travel, mail stations, railway stations, subway stations, custom inspection areas, traffic control zones, ship or submarine, airplanes, schools, hotels, restaurants, shopping centers, recreation centers, buildings, and other public places, etc. This configuration can be easily implemented to detect gun powders and other explosives, flammable materials including liquids, or other hazardous materials.

Wired Sensor Network

Figure 4A:
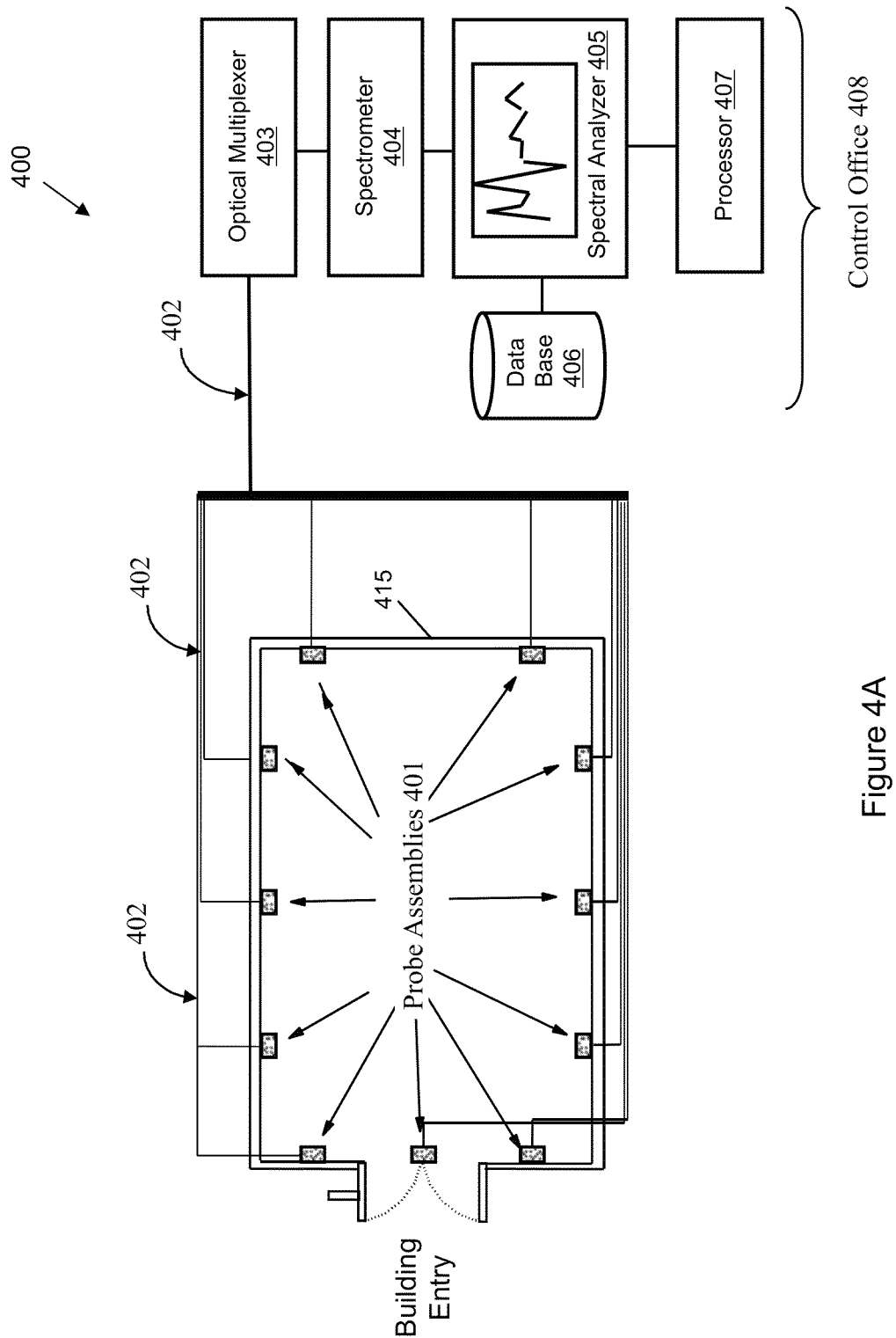
FIG. 4A is a schematic diagram for a network of wired-line connected Raman scattering probes for monitoring the safety of a building.

Referring to FIG. 4A, a sensor-network system 400 is used in safety monitoring of a public building such as airport, railway, bus stations, ballpark buildings, Federal buildings, auditoriums, theaters, courthouses, shopping mall, other public buildings, or a people gathering place. A plurality of probe assemblies 401 are installed at various locations in a public building 415 or others protected areas. Each probe assembly 401 includes a probe head and a sensor (not separately shown in FIG. 4A). The probe head can be implemented similar to the probe head 110 (FIG. 1A) but can include a laser device. The sensor is compatible with the sensor 105 (FIG. 1B) that includes a nano surface structure on the surface. The sensor can also be a liquid solution that is configured to receive reagent to be detected. The solution can also include nano particles configured to adsorb the molecules of the reagents. The probe assemblies 401 are applied to monitor many different molecular substances to provide earlier detection of any dangerous or harmful chemicals enter into the monitor areas. The optical signals collected by the probe assemblies 401 can be fed in multiple channels via optical fibers 402 to an optical multiplexer 403 at a control office 408. The optical signals are analyzed by a spectrometer 404 to produce spectral signals, which are analyzed by a spectral analyzer 405. Spectral signatures are identified in the spectral data by the processor 407 using pre-stored spectral signatures in a database 406. Particular examples of hazardous material monitoring include, but not limited to detection of explosive materials including liquids, chemical or biochemical weapons including anthrax, flammable liquid materials, drugs, and so on.

Wireless Sensor Network

Figure 4B:
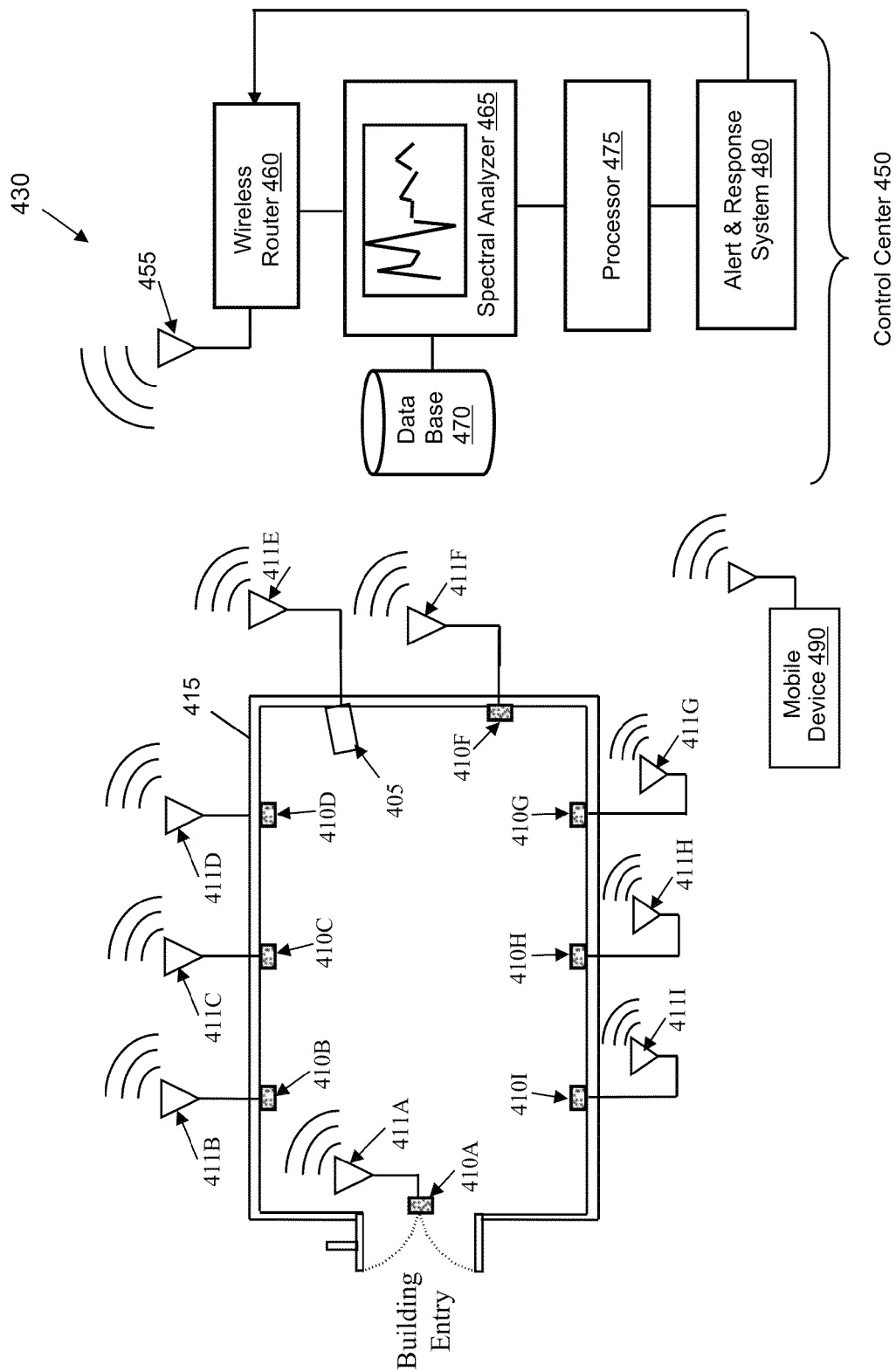
FIG. 4B is a schematic diagram for a network of wireless connected Raman scattering probes for monitoring the safety of a building.

In some embodiments, a sensor-network system 430 is shown in FIG. 4B. A building 415 includes a building entry and a plurality of walls. Probe assemblies 410A-410I are installed at various locations in the building 415. The probe assemblies 410A-410I are respectively coupled to antenna 411A-411I which can transmit locally detected spectral information to a control center 450.

Figure 4C:
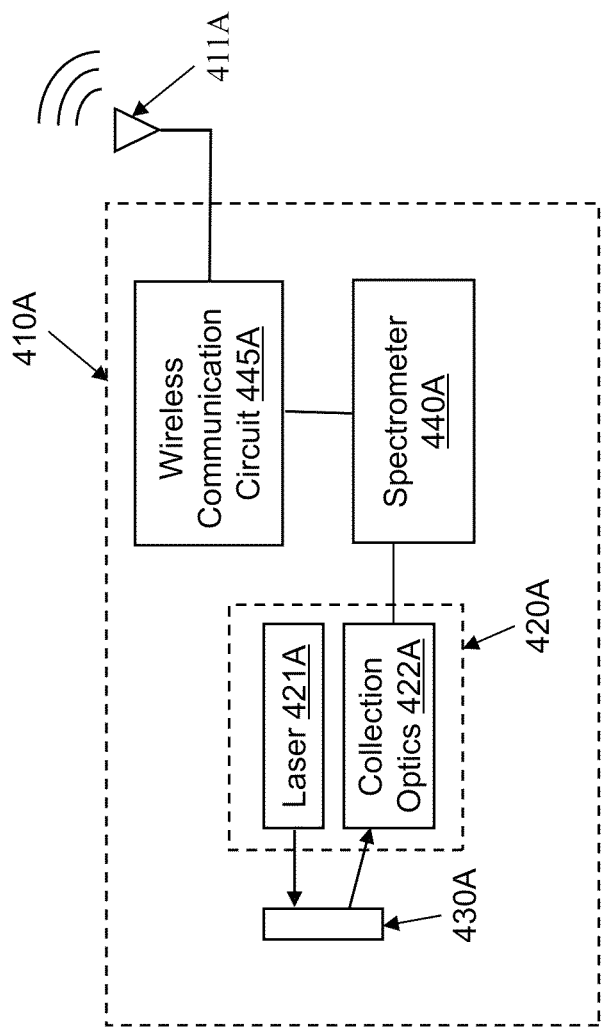
FIG. 4C illustrates an exemplified configuration for a probe assembly capable of wireless communication with a control center.

Each probe assembly 410A, as shown in FIG. 4C, includes a probe head 420A and a sensor 430A positioned adjacent to the probe head 420A. The sensor 430A can collect substances in the ambient environment. In some embodiments, the sensor 430A includes a nano-structured surface that can adsorb molecules of the substance collected in the ambient environment. The probe head 420A includes a compact laser 421A (e.g., a semiconductor laser) that is configured to illuminate a laser beam on the sample molecules in or adsorbed on the sensor 430A. The probe head 420A further includes collection optics 422A that can collect light scattered from the sample molecules in or adsorbed on the sensor 430A, wherein the scattered light comprises information about molecules of the sample molecules. The sensor 430A is compatible with the sensor 105 (FIG. 1B) that includes a nano structure on the surface. The sample molecules can be adsorbed on the nano surface structures to scatter the incident laser light. The sensor 430A can also include a liquid solution that is configured to receive reagent to be detected (e.g., see FIG. 7 below). The solution can also include nano particles configured to adsorb the molecules of the reagents.

The probe head 420A also includes a compact spectrometer 440A that is configured to produce a spectrum of the scattered light collected by the probe head 420A. The spectral data is output from the spectrometer 440A to a wireless communication circuit 445A. The wireless communication circuit 445A can include an RF transceiver, one or more amplifiers, and impedance matching circuit. The wireless communication circuit 445A is configured to transmit the spectral data detected by probe assembly 410A to the control center 450 (FIG. 4B).

The control center 450, referring back to FIG. 4B, includes a wireless router 460 coupled with an antenna 455 configured to receive the wireless signals from the antenna 411A-411I and produce electronic signals comprising spectral data extracted from the wireless signals. The control center 450 can be located within a short range (e.g., within a couple of miles) from the source location (e.g., the building 415) to allow wireless signals comprising the spectral data to be communicated in a wireless protocol such as Bluetooth, WiMax, WiBro, WiFi, WLAN, 802.16, and others. The control center 450 can also be located at a long distance from the source location, wherein the wireless signals comprising the spectral data can be communicated using wireless communications standards and protocols such as Global System for Mobile communications (GSM), Universal Mobile Telecommunications Service (UMTS), and Code Division Multiple Access (CDMA). GSM can include GPRS, EDGE and CSD. UMTS can include Wideband Code Division Multiple Access (WCDMA), High-Speed Packet Access (HSPA), High-Speed Downlink Packet Access (HSDPA), UMTS-TDD, and Long Term Evolution (LTE). CDMA can include CDMA2000 and Ultra Mobile Broadband (UMB).

A spectral analyzer 465 at the control center 450 is configured to receive the electronic signals comprising the spectral data from the wireless router 460. A spectrum such as Raman spectrum is obtained and analyzed by the spectral analyzer 465. As described in more detail below, different chemical or biological substances often carry unique spectral signatures. These spectral signatures can be predetermined using a known chemical or biological substances and a sensor similar to the ones installed in the probe assemblies 410A-410I. The spectral signatures can be stored in a database 470. The spectral analyzer 465 can use the spectral signatures stored in the database 470 as reference to identify spectral signatures in the spectral data. A processor 475 can compute and determine substances captured by the plurality of probe assemblies 410A-410I at different times at different locations of the building 415. If a hazardous substance is identified from the spectral data obtained by one or more probe assemblies 410A-410I, the processor 470 can immediately send a report to an alert and response system 480. The hazardous substance can, for example, include explosives and flammable materials, poisonous gas and other harmful chemicals, and contagious virus and bacteria. The alert and response system 480 is configured to send warning notification signal to the wireless router 460, which can in turn transmit wireless signals to mobile devices 490 and other wireless devices to alert security and other responsible personnel to take proper response actions. The mobile device 490 can include a laptop personal computer, a personal digital assistant (PDA), a mobile internet device (MID), a cellular phone, a smart phone, or a wireless server or router. An application example is to remotely or stand-off monitor a vehicle passing a inspection station on a road, which the sensor in the station is electrically shielded in order not to trig any explosive materials in a nearby vehicle. The inspection action can include to wirelessly control a robotic arm with the probe to collect air phase sample in a vehicle to test, a analyzer can be connected with the probe with either wired (such as optic fibers and cables, etc.), or a wireless way.

Figure 4D:
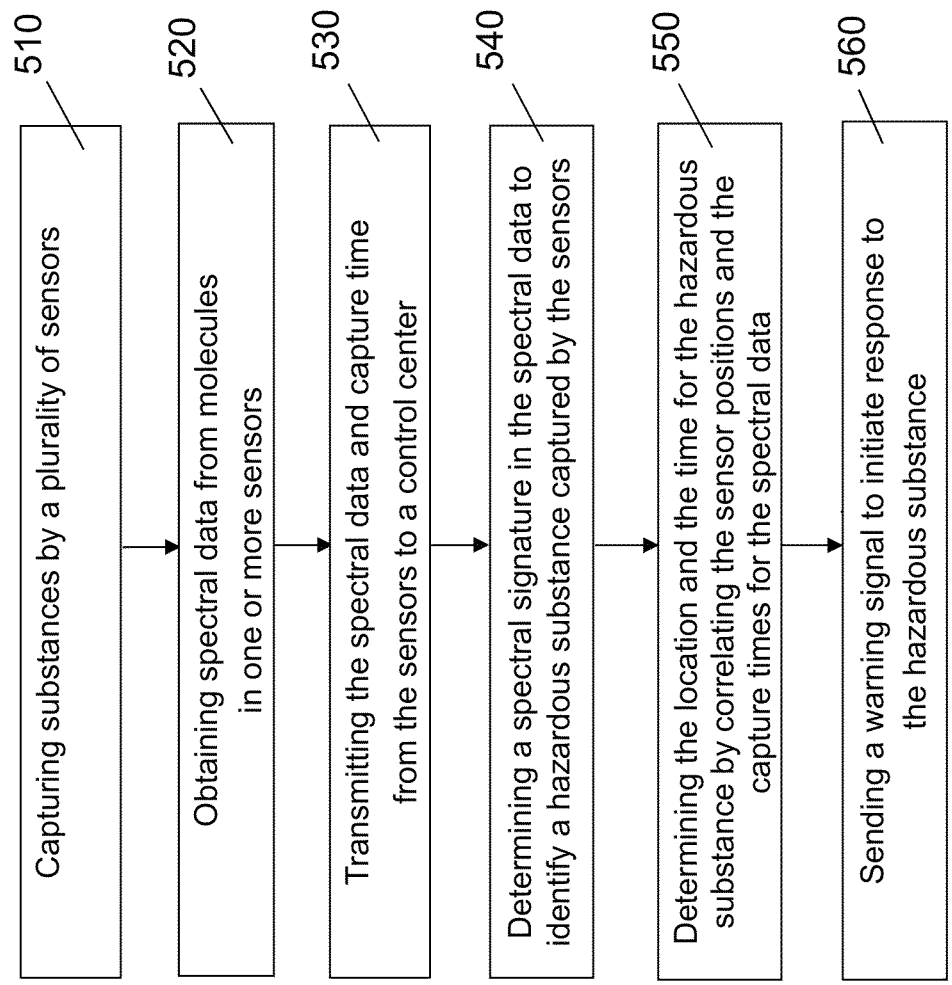
FIG. 4D is an exemplified flowchart for identifying the time and the location of the source of a hazardous substance.

In some embodiments, referring to FIG. 4D, a network of probe assemblies are installed at predetermined positions in a building, an airport, a custom, a conveyance system for cargo or luggage, a health advisor's office, a check station on a road, a harbor, in a vehicle, a ship, a submarine, an airplane, a train, a subway, a building, an industrial site, a resort area, a shopping mall, a research Lab, a school, or a water source, a people gathering place, etc., as described above in relation to FIGS. 3B-4C. Each probe assembly includes a sensor and a probe head configured to emit a laser beam and collect scattered light from the molecules in the sensor. The sensor can have a nano structured surface configured to adsorb the molecules. The probe assembly also includes a spectrometer for producing spectral data such as Raman spectrum from the scattered light. The network of sensors can periodically capture substances (step 510) from each sensor's environment. For sensors having nano-structured surfaces, molecules of the captured substance are adsorbed on the nano structured surfaces on the sensors. Spectral data are next obtained from the molecules adsorbed to the nano structured surfaces in one or more sensors (step 520). Alternately, the molecules to be detected can be captured in a sample solution, and/or adsorbed to nano particles suspended in the sample solution. As described above, a laser beam is emitted by a laser in the probe assembly to illuminate the molecules adsorbed on the nano structured surfaces on a sensor or in a sample solution. Light scattered by the molecules is collected by the probe assembly. The spectral data is obtained from the scattered light by a spectrometer in the probe assembly. An example for the spectral data is Raman spectrum. The nano structured surface on the sensor provides surface enhancement to the signal intensity in the Raman spectrum. The substance capture and associated spectral data can be periodically conducted, for example, at 1 min, 10 min, 15 min, or hours of intervals. In some embodiments, spectral data can be produced in response to a command received from a control center.

The spectral data is next transmitted from the sensors to a control center (step 530). The substance capture time can also be transmitted in conjunction with the spectral data. The spectral data transmission can be via a wired data lines (as shown in FIG. 4A) or a wireless communication network (as shown in FIGS. 4B and 4C). The data center can include a spectral analyzer and a data base storing spectral signatures of predetermined know hazardous substances. The spectral analyzer is used to determine if a spectral signature exists in the spectral data received from the sensors. A hazardous substance can be identified if a spectral signature for a known hazardous substance is found in the spectral data (step 540).

The hazardous substance may be identified by more than one sensor in the network of sensors. The identifications of the hazardous substance can occur at different times by different sensors. For example, as a passenger 200-2 walks through the passageway 210 (FIG. 3A), different sensors in the network may pick up the hazardous material at different times and at different location. A processor (475, FIG. 4B) at the control center can determine the location and time for the hazardous substance by correlating the sensor positions and the capture times for the spectral data (step 550). The location for a stationary hazardous material can be determined by interpolating the positions of the sensors. The location dependence of the hazardous substance detected at different sensors can be used as weighting factors to determine the exact location of the hazardous material, which can be expressed in a two-dimensional (2D) coordinate or a three-dimensional (3D) coordinate. The capture times of the hazardous substance by different sensors at different locations can be used by the processor at the control center to determine a spatial-time profile (that is locations as a function of time) for the hazardous material. The position of the future locations of the hazardous can therefore be predicted by the processor.

In some embodiments, the spectral data collected by the sensors can be used in conjunction with image data captured from the scene near the spectral sensors. For example, a video camera 405 at a location near the spectral sensor where the hazardous substance is identified can capture a suspected person or package. The image of the suspected person or package can be stored and reported in association of the location of the hazardous substance to prepare for an appropriate response.

A warning signal is next sent to an alert response system which can initiate response to the hazardous substance (step 560). The warning signal can be in the form of emails, text messages, and voice phone call, etc. The level of urgency can be categorized by different risk levels such as green (safe), blue, yellow, orange, red (the most risky). The warning signal can include the current and/or anticipated position of the hazardous substance as well as the suspected exterior appearance for the carrier or the package for the hazardous substance. Appropriate personnel can be alerted. Security personnel can be dispatched to the location of the hazardous substance. An evacuation can be initiated.

Figure 5:
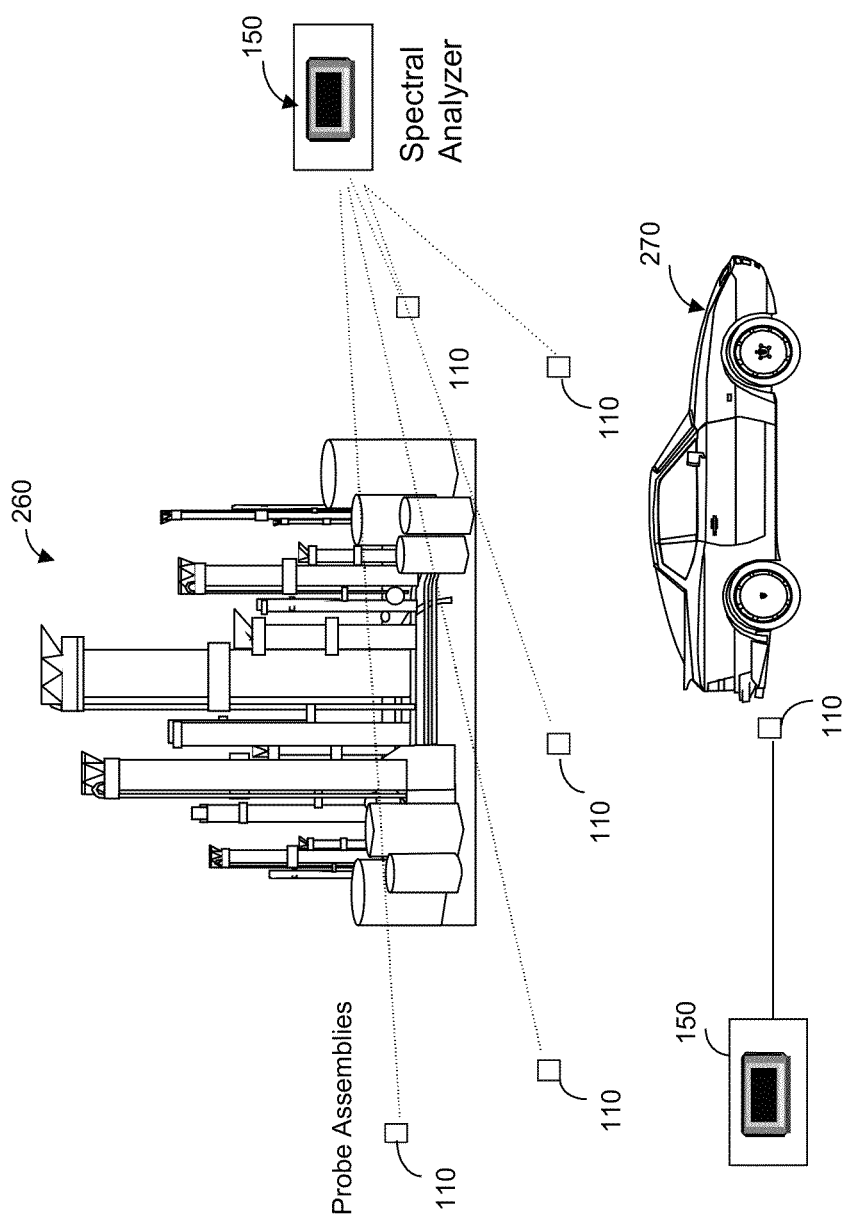
FIG. 5 is a schematic diagram showing environmental monitoring using a Raman scattering probe.

FIG. 5 is schematic diagram of applying the disclosed sensors to monitor harmful chemicals released into the environment. The probe assemblies 120 are distributed around potential pollution source, e.g., a factory 260 or around highway where great number of automobiles 270 pass through. The probes assemblies 120 can be distributed around the monitored areas and transmit scattered light to a central spectrum analyzer 150, which can determine the contents and concentration of substance released into the environment. The monitoring sample can be, but not limited, soil, water, lake, river, seashore, well, plants, air, aerosol, etc. This application can be extended to car exhausted gas detection and monitoring by placing the probe assembly at the outlet of a car exhaust.

Some Applications of Nano-Structure Based Spectral Sensing

In some embodiments, compact Raman sensor having wireless communication capability can be used inside human body. For example, a system-on-chip Raman system can include on-chip mini-laser source, semiconductor or MEMS device based mini-spectrometer, wireless module, mini-probe, etc. One exemplified application is disease diagnosis of digest system. For example, a patient can swallow a tablet sized Raman spectral sensing system after his/her digest system got cleaned. Raman spectral scans can be taken at predetermined time intervals. The spectral data is then transferred by a wireless module to a wireless receiver outside of the human body. A computer can analyze the spectral data by searching and matching existing data in a database, which can lead to identification of a disease. In another exemplified application, a needle-shaped minimally invasive probe head can bring mini-Raman sensor into diagnosis area inside a human body. Raman spectral data can be transferred through optic fiber, or wireless module. Such applications can include but not limit to diagnosis of cancers (such as breast cancer, colon cancer, esophageal cancer, lung cancer, liver cancer, bladder cancer, pancreas cancer, kidney cancer, ovarian cancer, oral cancer, neck and brain cancer, skin cancer, and stomach cancer), Alzheimer's disease, Parkinson disease, etc. An exemplified cancer marker for SERS is humane epidermal growth factor (HER2), CA-125, or CA-549. An example for a SERS marker for lung cancer is carcinoembryonic antigen (CEA), or A-549.

The disclosed Raman spectral sensing systems and methods are suitable for biotechnology and biomedical applications, such as biometric identity verification by testing samples of tissues or body fluids of a human or an animal, A549 cell of lung cancer, DNA, RNA and proteins, and biomarkers include CEA, CA-125, CA 19-9, CA-549, PSA, AFP, A549, DNA sequencing, DNA sorting, etc.

The disclosed Raman spectral sensing systems and methods are suitable for drug screening. The samples for drug screening can be obtained by human body fluid test, or/and breath test. The disclosed Raman spectral sensing systems and methods are also suitable for forensic applications. The samples can be in the forms of liquid phase, such as human body fluid or animal body fluid, for example, saliva, urine, blood, serum, or powders. Related applications also include false signature recognition; human identification and screening by DNA profiling; identify microscopic paint fragments, fiber identification, etc.

The disclosed Raman spectral sensing systems and methods are suitable for security applications such as detections of hazardous materials, chemical weapons, biological agents, explosive materials (in the forms of powders, solids, liquids, aerosol, or gases), flammable materials including liquids, solids and powders, narcotic drugs, and radioactive materials.

The disclosed Raman spectral sensing systems and methods are suitable for food safety inspection and environmental monitoring. Harmful chemicals and biological agents in the forms of gas, liquid, powder, gel, aerosol, or solid phases can be monitored in food, fruits, beverages and water. The harmful chemicals can include residue pesticides (e.g., methamidophos, cypermethrin, deltamethrin, malachite green, etc.), dioxins, illegal artificial additives (e.g., sudan I, sudan II, sudan III, sudan IV, melamine, Rhodanmine B, sulfide (e.g., NaS), art green, etc.), heavy metals in water including but not limited to Pd, Cd, Hg, As, Cr, or Cu metals and those metal containing compounds, cyanides (e.g., KCN, NaCN), chlorates, sulfates. Food and drug processing by-products (e.g., acrylamide formed from potato chips from processing temperature over 120° C., melamine form from biochemical drug manufacturing process, etc.) can be monitored to detect harmful chemicals such as acrylamide and melamine using the disclosed Raman spectral sensing techniques. Foods inspections include but not limit to potato chips, French fries, fried potato, potato crisps, cookies, crackers, cereal products, crisp bread, bread, coffee, prepared toast, roasted nuts, biscuits, chocolates, popcorn, and aquatic products including fish, etc. drug investigation include but not limit to biochemical drug raw materials, semi-finished products, or products containing NH2 group and/or aromatic group.

The disclosed Raman spectral sensing systems and methods are suitable for identifying and monitoring food packaging processing and preparation materials, which includes identifying and screening polyvinyl chloride (PVC), phthalate contained materials, and polystyrene (PS), used as the microwave food wrap, kitchen film, food packaging, food and liquid container, and processing and preparation materials.

The disclosed Raman spectral sensing systems and methods are suitable for identifying counterfeit merchandizes such as medicines, drugs, Chinese medicine, milk-based powders, edible oil, wines, tea, cigarette, gemstones, currency bills, false signature through inks, art pieces, gasoline, etc.

The disclosed Raman spectral sensing systems and methods are suitable for industrial quality control and production safety monitoring. Other areas of applications include process control for product quality, process and production safety at gas and wet chemical process lines, which can include petroleum refinery plant, chemical engineering manufacturing plant, semiconductor wet chemical process line in clean room, airline and space shuttle, boat, ship, submarine, a chemical related process line or application site, etc.

The disclosed Raman spectral sensing systems and sensor networks can be applied to medical clinic offices, surgery operation rooms, shopping centers, resort area, buildings, customs, road check station, harbors, airports, vehicles, boats, ship, submarine, airplanes, space shuttles, industrial process sites, R & D research labs, quality control offices, education institutes, labs offices, and water sources such as surface water, wells, ground waters, and so on.

Figure 6A:
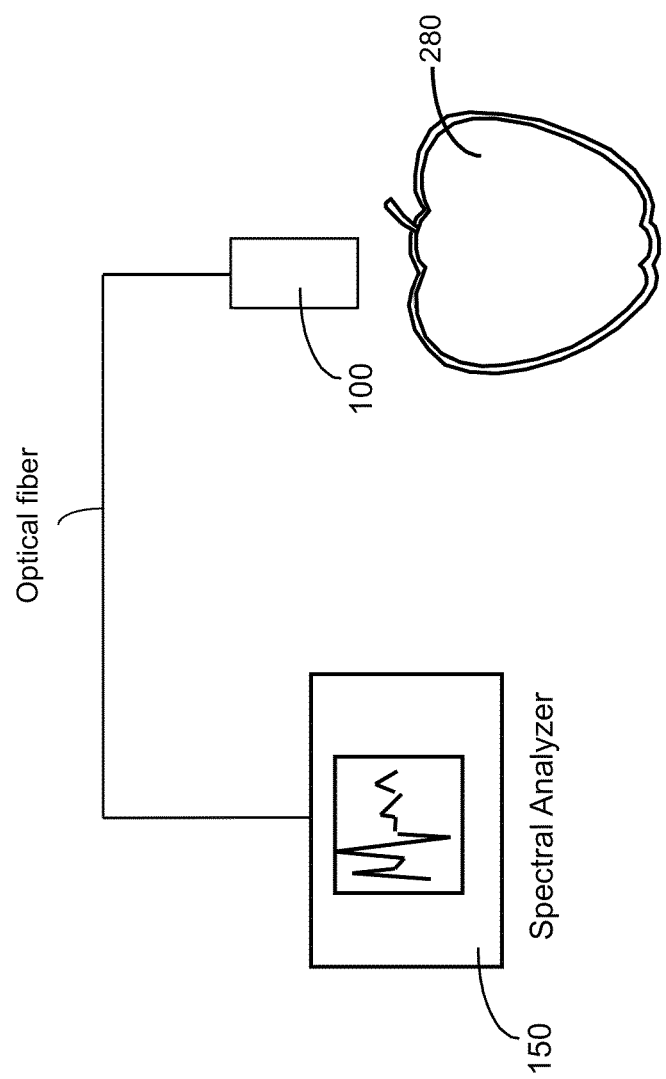
FIG. 6A is a schematic diagram for food safety inspection using a Raman scattering probe.

FIG. 6A is schematic diagram of applying the technology of Surface-Enhance Raman Scattering using a sensor to monitor substances for inspecting quality and safety of foods. A light scattering probe 100 is placed close to a food item 280, i.e., edible oil, an apple or different fruits, vegetables or other food items that could be contaminated through transportations, food processing, or even food growth process. The molecules of residue pesticide, veterinary drug, hormone, fertilizer, illegal food additive, migrated from or on a food packaging material, or other contaminations are drawn into the light scattering probe 100. The molecules of the harmful substances can be adsorbed to nano structured surfaces such as nano particles in a colloidal solution or a microchip containing a nano surface structure. As described in more detail below, the spectral sensing techniques can include Surface-Enhance Raman spectroscopy, normal Raman spectroscopy, Fluorescence spectroscopy, etc.

Figure 6B:
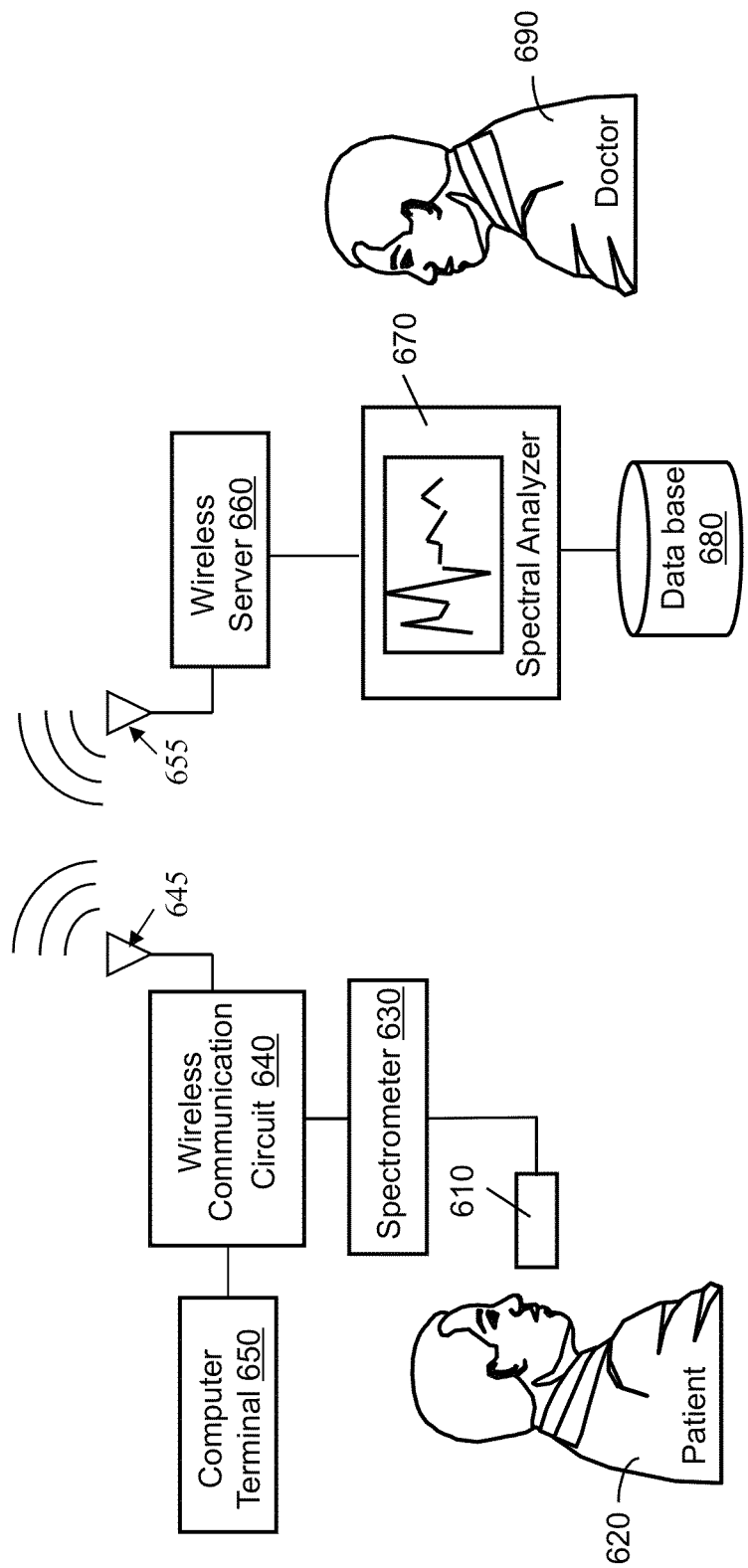
FIG. 6B illustrates an exemplified system for remote disease diagnosis and biomedical detection using a Raman scattering probe.

FIG. 6B shows an application of disclosed Raman spectral technique to monitor substances for early disease detection and diagnosis. A doctor can remotely monitor and diagnose a patient at home or hospital. The probe assembly 610 is placed near a patient 620 for carrying out a physical examination, a check-up from recuperation from a sickness, or for disease diagnosis. Human breathed air can carry special chemicals such as alkenes and benzene derivatives. If a person under screening has a disease such as cancers including but not limited to lung cancer, breast cancer, liver cancer, pancreas cancer, ovarian cancer, etc., the disclosed Raman sensing systems and methods can fingerprint those chemicals in breath test to identify some special diseases such as cancers. The patient blows the outpoured breath-air to the probe assembly 610. The sensor in probe assembly receives the inlet air for generating a scattered light corresponding to the molecules contained in the airflow from a patient or a breath air sample provider. Spectral data of the scattered light is produced by a spectrometer 630. A wireless communication circuit 640 can convert the spectral data into an RF signals which can be transmitted in a wireless signal by an antenna 645. The wireless signal can also include information (e.g., patient's name, identification, etc.) about the patient 620. A computer terminal 650 coupled to the wireless communication circuit 640 can display information received from a doctor's office and allows the patient to input information to be transmitted to the doctor's office. Similar application can be done by testing a person or animal's body fluid.

An antenna 655 at a doctor or a health advisor's office receives the wireless signal or wireless signal from a plurality of patients at a distance. A wireless server 660 can down convert the wireless signal and extract the spectral data and other information about the patient or input by the patient. The spectral data is analyzed by a spectral analyzer 670 using spectral signatures stored in a data base 680. The spectral signatures can indicate a plurality of predetermined diseases. The determination of a spectral signal in the spectral data may indicate the patient is carrying the associated disease or has not fully recovered from a previously diagnosed sickness. The signal strength can indicate the severity of the disease suffered by the patient. A doctor 690 can also make a determination about the nature and severity of the disease by visually inspecting the spectral data. The described systems and methods are suitable for early disease diagnosis which disease includes, but not limited to lung cancer, breast cancer, stomach cancer, Liver cirrhosis, failing kidney, ulcer cancer, etc. In case of testing human body fluids, the fluid is dropped on a sensor manually or automatically, or Raman sensing device can be designed to connect to toilet for easy sample collection as smart toilet to timely monitor abnormal signals for disease and drug detection. This application also includes identifying and sorting protein, DNA and RNA. All testing samples in above applications can be placed in contact with a sensor to enhance the sensitivity and intensity of Raman scattering detections. The disclosed trace chemical detection using Raman light scattering can also be applied to other areas, including but not limited to identify cancers, HIV, Alzheimer's disease, Parkinson disease, non-invasively test glucose to monitor diabetes, non-invasive test and evaluate level of carotenoids to monitor antioxidant status for early cancer screening purpose, illicit drug, and so on.

Figure 6C:
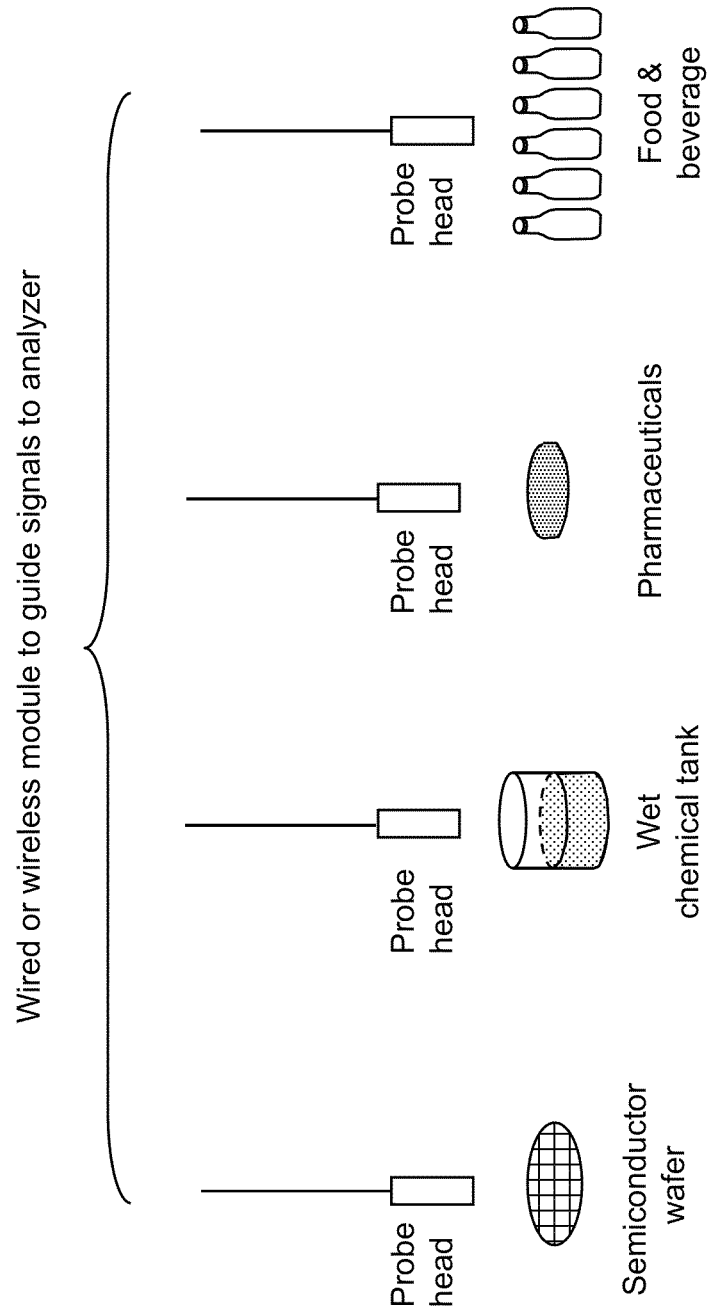
FIG. 6C is a schematic diagram showing quality control and food inspection using a plurality of Raman scattering probes in a multi-channel sensing system.

FIG. 6C is schematic diagram of Raman scattering application in industrial quality control, safety assurance, or food safety in distribution and retail channels. The applications can include in-line monitoring of chemical concentrations in a plurality of wet chemical process line, remotely or stand-alone monitoring of sealed chemical tanks, remote trace chemical detection, semiconductor wafer defect evaluation, and monitoring of the food, fruit and vegetable storage, etc. For example, the food products can include edible oil sampled at different locations. The spectral signals collected by probe heads at a plurality of locations can be fed by optical fibers in multiple channels to a spectral analyzer at a central office, wherein the spectral data are analyzed. The spectral signatures in the spectral data can lead to the identification of harmful substances in the food, drug, a chemical related product, etc.

Figure 6D:
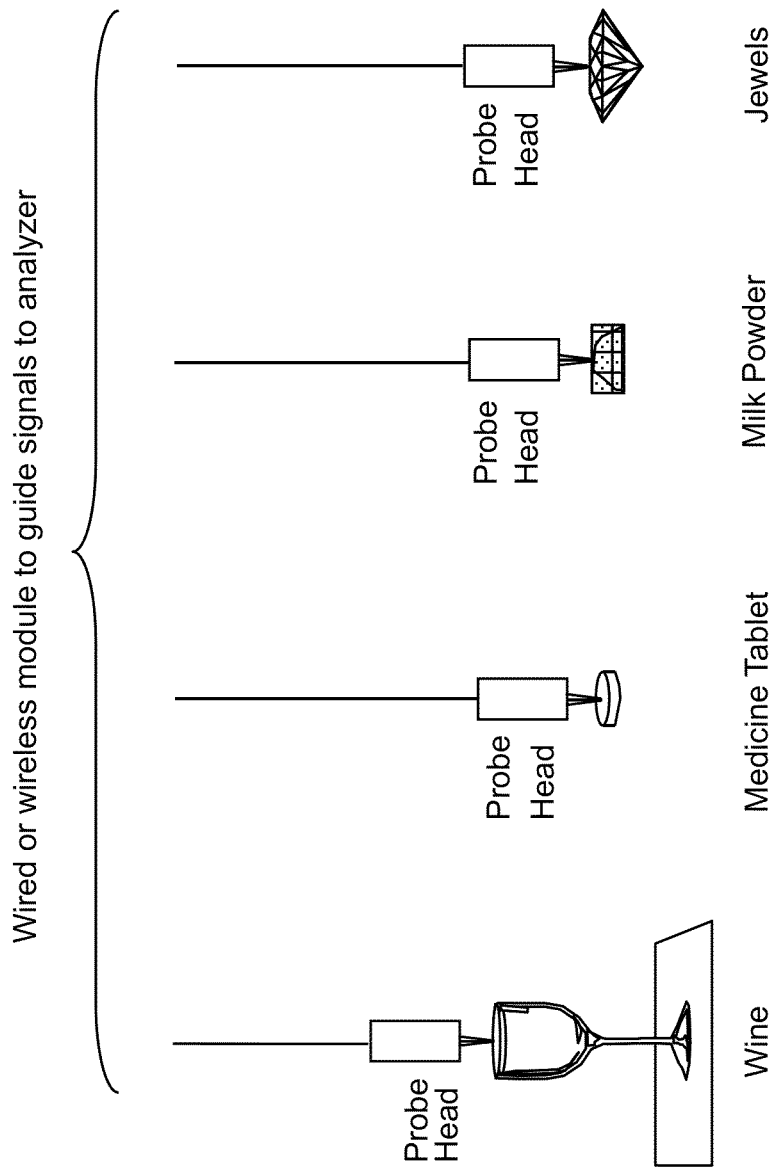
FIG. 6D is a schematic diagram showing detection of counterfeit merchandise, inspection of safety and quality for food and beverages, and drug authentication using a plurality of Raman scattering probes in a multi-channel sensing system.

FIG. 6D is schematic diagram of a multi-channel Raman scattering sensing system that can identify and screen materials for counterfeit merchandise and food safety screening. The applications may include operations such as food, drug and medicine screening, which may or may not involve a nano structured sensor module. The excitation laser beams in the probe heads can directly impinge on samples under test. The scattering light from the tested materials are collected by the probe heads. The Raman spectra of the scattered lights show spectral signatures that can provide indications whether there are illegal additives added to the commercial merchandises. The potential counterfeit merchandise such as milk-based powder, wine, and medical tablets may be placed under the Raman detector as materials under investigation and screen. The spectral signals can be collected from different samples and fed by optical fibers in multiple channels to a spectral analyzer at a central office, wherein the spectral data are analyzed. The applications can be extended to authenticated signatures and currency bills by detecting false signature and false bills by generating Raman scattering spectrum of the signature and dollar bills and compare these spectra with measurements obtained from authenticated signature and dollar bills.

Spectral Sensing Using Nano-Particles

Figure 7:
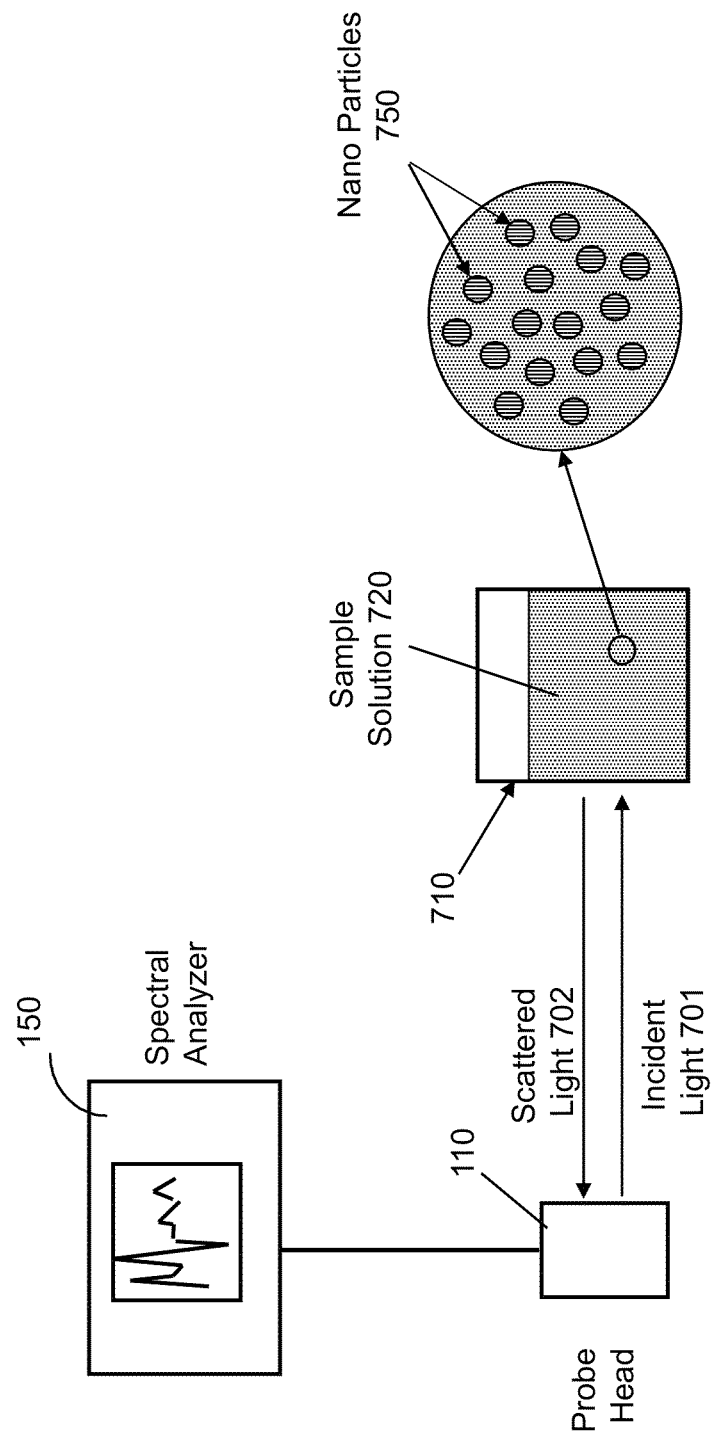
FIG. 7 is a schematic diagram showing the detection of trace chemical or biological substances using a solution containing nano particles and a light scattering probe in accordance to an embodiment of the present application.

In some embodiments, referring to FIGS. 7 and 8, a sample solution 720 is introduced into a container 710 such as an optical vial or a cuvette made by quartz, glass, or plastic materials (step 810). The container 710 can be an optical vial, a beaker, or a transparent test tube, etc. The sample solution 720 also contains nano particles 750. The nano particles 750 can exist in the form of a colloidal suspension in the sample solution 720. A reagent containing the chemical or biological substance is introduced into the sample solution 720 (step 820). The reagent can exist in a solid, a liquid, an aerosol, a sol gel, or a gas form. The reagent is dissolved in the sample solution 720 to allow molecules of the chemical or biological substance to be adsorbed on surfaces of the nano particles 750 (step 830). A probe head 110 (shown in FIG. 1A) emits an incident light 701 (such as a laser beam) to illuminate the nano particles 750 and the chemical or biological substance in the sample solution 720 (step 840). Scattered light 702 from the nano particles 750 and the chemical or biological substance is collected by the probe head 110 (shown in FIG. 1A) (step 850). The output signal from the probe assembly is analyzed by the spectral analyzer 150. As shown in more detail in the examples below, a Raman spectrum is obtained from the scattered light (step 860). Spectral signature(s) in the Raman spectrum can be used to determine the trace chemical or biological substance adsorbed to the nano particles (step 870).

In one aspect of the present disclosure, material compositions of the nano particles 750 in the sample solution 720 are prepared to enhance the intensity of the scattered light 702 and Raman spectral signal from the nano particles. For example, the nano particles 750 include metallic materials such as Al, Ag, Au, Cu, Fe, Co, Ni, Cr, Zn, Sn, Pd, Pt, and their alloys, oxide materials such as titanium oxide, silicon oxide, zinc oxide, etc, silicon, and polymeric materials. The nano particles 750 can be charged in the sample solution 720 to assist the separation between the nano particles and the formation of a colloidal suspension. The nano particles 750 can also include polymers tethered to the particle surfaces to help repel each other in the sample solution 720.

In some embodiments, the nano particles 750 can include a core made of a magnetic material such as $Fe_2O_3$, $Fe_3O_4$, CoMe, or Fe, Co, or Ni contained compound, and a shell of Au wrapped around the magnetic core. The core can have diameters in a range between 1 nm and 500 nm. After the Au shell is formed on the core, the diameter of the core/shell particles can be in a range from about 5 nm to about 50 μm. The magnetism in the cores of the nano particles allows more effective separation and collection of the particles using an external magnetic field. The Au shell can enhance the adsorption of the molecules of the substance to be detected. Furthermore, the magnetic field produced by the magnetic core can enhance resonance and increase signal strength in Raman scattering.

In some embodiments, the nano particles 750 can include a Ag or SiO$_2$ core and a Au shell. In some embodiments, the nano particles 750 can include a Ag or Au core, and SiO$_2$ shell.

In some embodiments, the nano particles 750 can include carbon nano tubes. The diameters of the carbon nano tubes are smaller than 1,000 nm. For example, the diameters of the carbon nano tubes can be from 0.3 nm to 100 nm. Their lengths can be from 5 nm to multiple millimeters. The length-to-diameter ratio of the carbon nano tubes can be as high as 50 million. The carbon nano tubes can have single-walls or multiple walls. The carbon nano tubes can be in the form of Fullerite, a torus, nanobuds, and nanoflowers.

In the presently disclosed systems and methods, when the carbon nano tubes can be placed into the sample solution 720 to form a suspension of nano particles in which the reagent is added. The carbon nano tubes can also be introduced on a substantially flat surface or a surface already formed with nano structures. A reagent is then introduced to such a surface containing the nano carbon tubes. In either case, a laser beam is directed to illuminate the nano carbon tubes and the reagent. Enhanced localized electro-magnetic field can assist charge transfer between molecules of the target chemical or biological substances, which results in enhanced Raman spectral signal.

In another aspect of the present disclosure, the nano particles 750 can be made of a magnetic or ferromagnetic material such as Iron (Fe), Cobalt (Co), and Nickel (Ni), or Fe, Co Ni containing compounds, such as alloy or oxide of Fe, Co, Ni, which can enhance the Raman spectral signal by applying an electrical field, a magnetic field, or an electro-magnetic field to the sample solution 720. The electrical field, the magnetic field, or the electro-magnetic field can be static or alternating.

In another aspect of the present disclosure, the sample solution 720 can include a mixture of nano particles of different material compositions. For example, the nano particles can include a mixture of silicon nano or micro-particles and metallic nano particles, or a mixture of silicon nano or micro-particles and polymeric nano particles, or a mixture of silicon nano or micro-particles, metallic nano particle, metallic oxide nano particles, and polymeric nano particles. Raman signal intensity can be enhanced by mixture compositions.

In another aspect of the present disclosure, the solvent in the sample solution 720 is also designed to enhance the light scattering intensity from the nano particles. It was found that ions and especially multi-valence ions can significantly enhance the signal intensity of the Raman signal. An ionic material can thus be added to the sample solution 720. Examples of ions that the ionic material carries to the sample solution 720 can include Na$^+$, K$^+$, Li$^+$, Ca$^{+2}$, Ba$^{+2}$, Sr$^{+2}$, Mg$^{+2}$, Mn$^{+2}$, Al$^{+3}$, Zn$^{+2}$, Sn$^{+2}$, Sn$^{+4}$, F$^-$, Cl$^-$, Br$^-$, and I$^-$, and so on. The ions can have mono charge or preferably double or high charges in the sample solution 720. The ions can have positive or negative charges. The sample solution 720 can have an ionic compound, including but not limited to LiF, NaF, LiCl, NaCl, KCl, KI, etc. The ionic concentration can be in a range from 10 µM to saturated level.

Figure 9A:
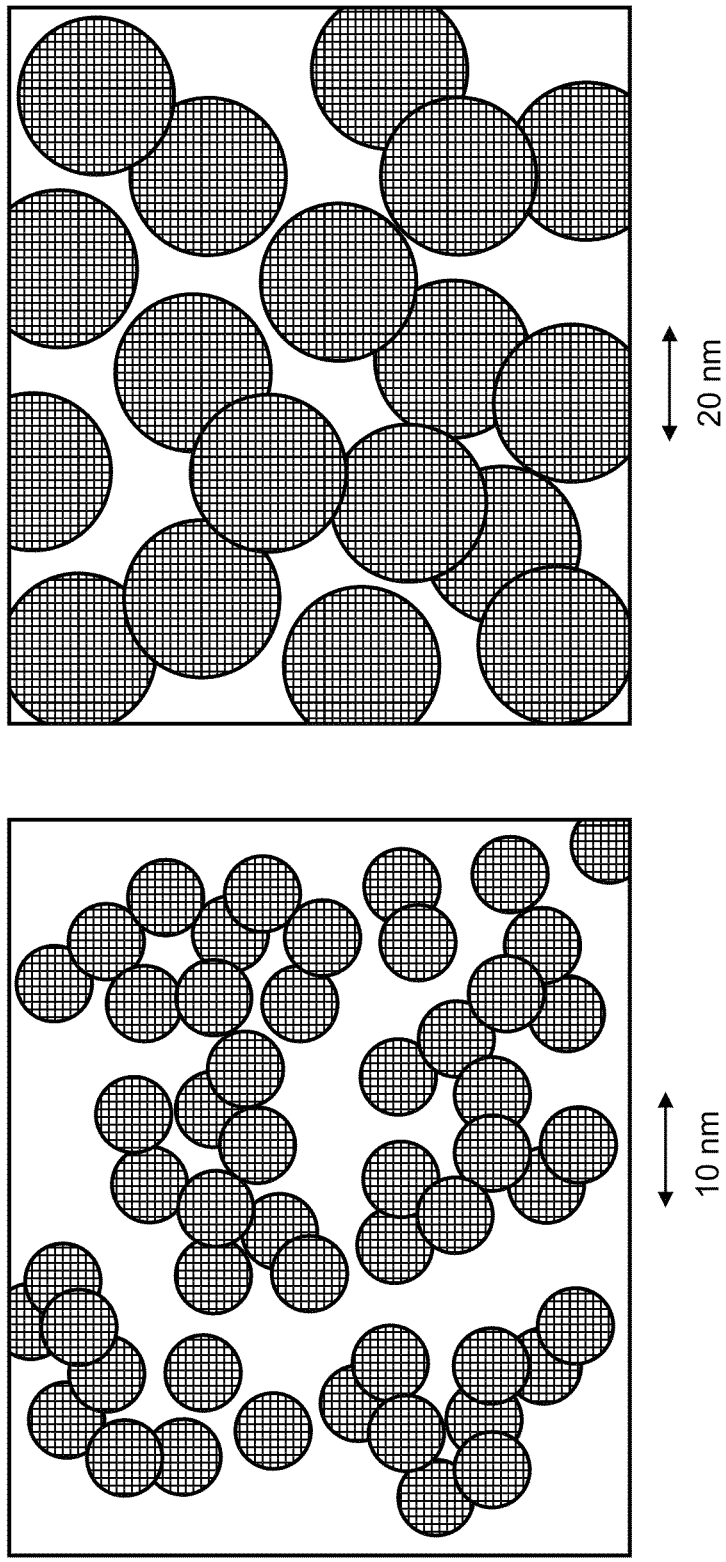
FIG. 9A illustrates exemplified nano particles as observed in micrographs obtained using a scanning electron microscope.
Figure 9B:
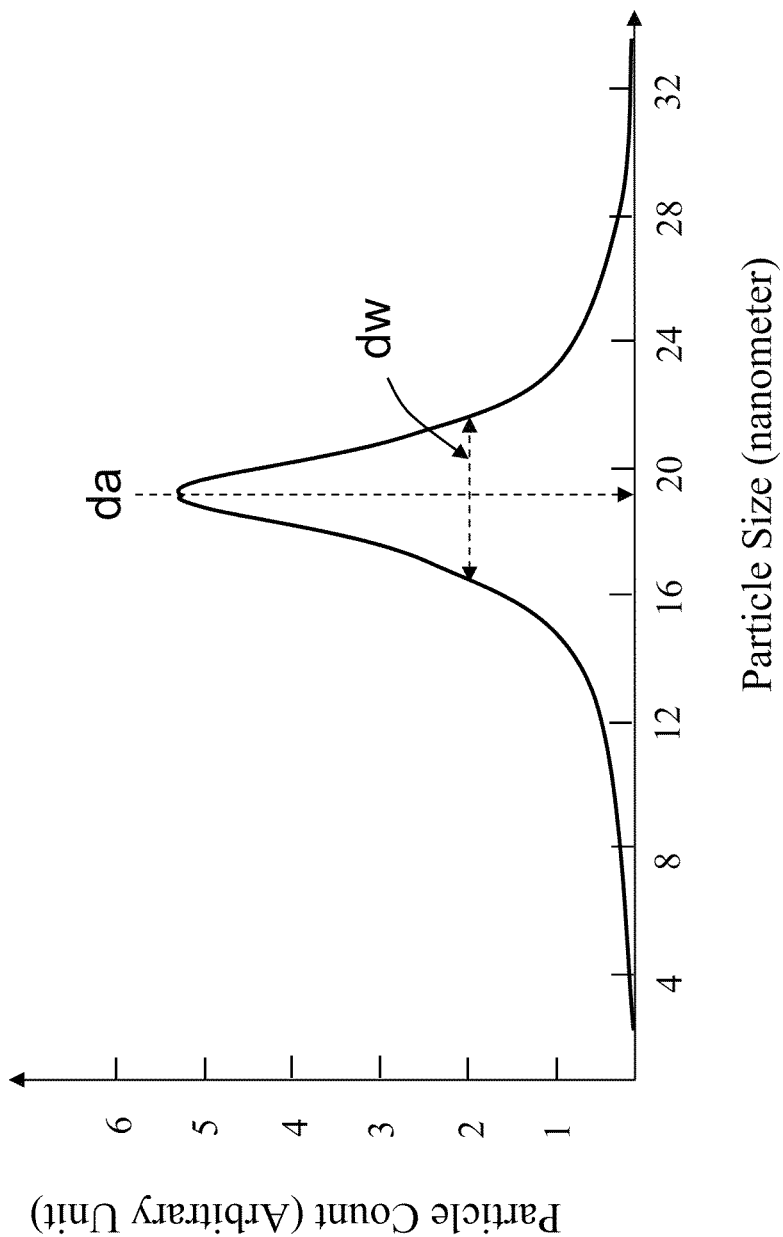
FIG. 9B is an exemplified size distribution of the nano particles in the solution shown in FIG. 7.
Figure 10:
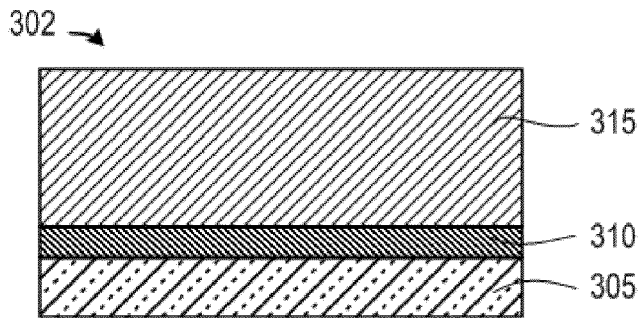
FIG. 10 is a cross-sectional view of a multi-layer layer structure to be used for fabricating a nano structure.
Figure 11B:
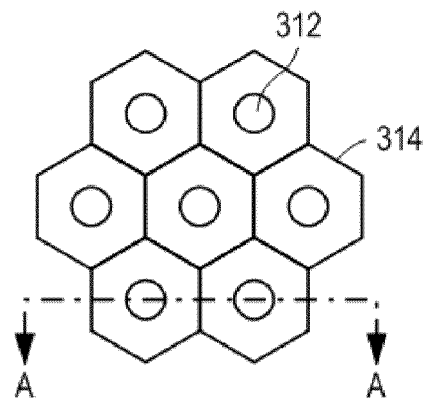
FIG. 11B is a top view of the multi-layer layer structure of FIG. 11A.
Figure 11A:
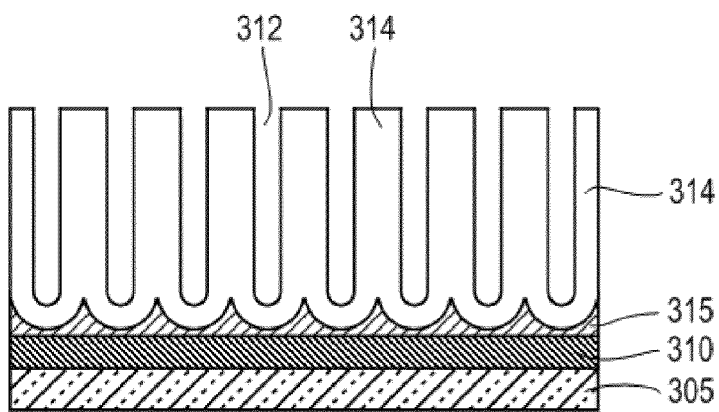
FIG. 11A is a cross-sectional view showing the formation of holes in the multi-layer layer structure of FIG. 10.
Figure 11C:
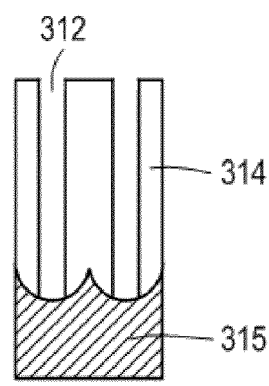
FIG. 11C is a cross-sectional view of the multi-layer layer structure along the line A-A in FIG. 11B.
Figure 12:
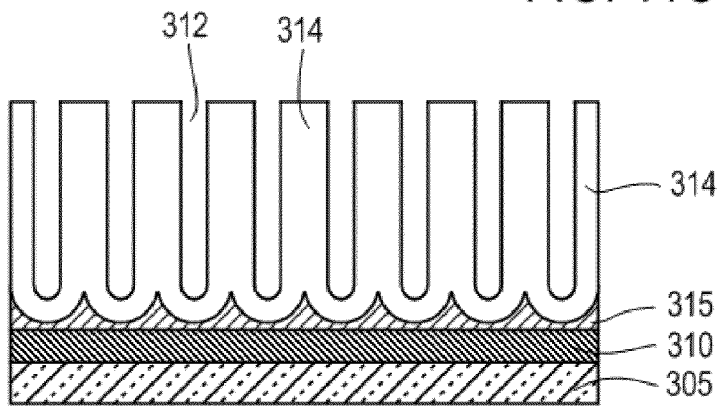
FIG. 12 is a cross-sectional view of the nano structure formed on the multi-layer layer structure after a wet chemical etch or chemical mechanical polishing.

The nano particles 750, as shown in FIG. 9A, can exist in round or irregular shapes. The nano particles can be individually separated and have also group in clusters in the sample solution 720. The nano particles 750 can have a size distribution, as shown in FIG. 9B, which is characterized by an average particle dimension d$_a$ and a particle-dimension distribution width d$_w$ for the particle size distribution. The average particle dimension d$_a$ can range from about 1 nm to about 10,000 nm, or from about 2 nm to about 500 nm. The ratio d$_w$/d$_a$ can range from about 0.01 to about 3, which defines a quite monodispersed distribution to a polydispersed particle distribution. The ratio d$_w$/d$_a$ can range from about 0.03 to about 1.

In some embodiments, a sample solution can include nano particles and micro-sliced tumor tissues as the reagent. The temperature of the sample solution can be controlled within a predetermined small range by a TE cooler and heater with temperature variation is smaller than 1° C. or 2° C. The temperature range can be from −20° C. to 60° C., or from 0° C. to 40° C. The sample solution is dried on a substrate surface leaving the nano particles and the reagent on the substrate surface. A laser beam is directed to illuminate on the nano particles and the reagent. The light scattered by the reagent containing the nano particles is collected. A Raman spectrum is obtained from the scattered light. Chemical or biological substance in the reagent can be identified using spectral signatures in the Raman spectrum.

Spectral Sensing Using Nano Surface Structures

In some embodiments, substance containing the trace chemical or biological substance can be introduced onto the surface of a chemical sensor, as shown in FIG. 1, from which an incident light can be scattered and a Raman spectrum can be obtained for material identification. FIGS. 10 to 15 show a series of processing steps for fabricating a nano-structured noble metal surface on the chemical sensor (or the sensor 105 in FIG. 1). A multi-layer structure 302 (FIG. 10) includes a substrate 305, a conductive layer 310, and an aluminum oxide layer 315. The substrate 305 can, for example, be n-type silicon flat wafer (3-8 Ω-cm) or oxidized (30-50 nm SiO$_2$) p-type silicon (5-10 mΩ-cm). The conductive layer 310 can include Ti or Ni and is deposited on the substrate 305 and can be electrically and thermally conductive. The thickness of the conductive layer 310 can be optimized to provide i) adhesion to a subsequently deposited noble metal film, such as Ag, Au, or Cu film, etc., ii) electrical conductive film to apply electrical bias to sensing surface in field application, iii) thermal conductive layer to apply lower temperature of sensing surface. The thickness of the conductive layer 310 can be generally controlled in the range of 10 Å-100,000 Å, typically in the range of 100 Å-1,000 Å.

A metal layer, for example, an aluminum layer 315, is deposited on the conductive layer 310. The aluminum layer 315 can have a purity of 99.99% and thickness in the range of 1.0-10.0 µm. The substrate 305, the conductive layer 310, and the aluminum oxide layer 315 are annealed at 400° C.-500° C. in a N$_2$ purged furnace for 2-5 hours to recrystallize the Al film. Anodization is then conducted to produce a porous structure in a form of porous aluminum oxide layer 315 as that shown in FIGS. 11A and 11B. A porous structure is formed on the aluminum oxide layer 315 wherein the porous structure includes a plurality of pores 312 surrounded by walls 314 with the cross section view along a horizontal line A-A shown in FIG. 11C. Then wet oxide etch process is carried out in FIG. 12 to remove both top porous Al$_2$O$_3$ layer and barrier layer. A second anodization is carried out to consume all Al metal so that the barrier layer and top porous Al$_2$O$_3$ layer are right above the conductive metal layer.

Figure 13:
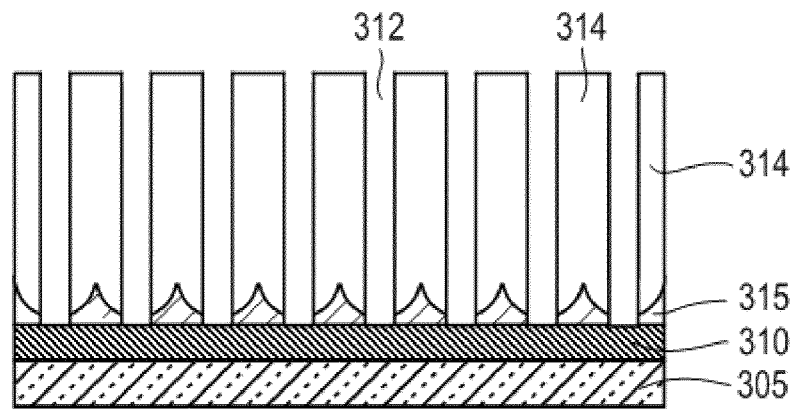
FIG. 13 is a cross-sectional view of the nano structure formed on the multi-layer layer structure after the removal of the barrier layer at the bottom of the holes and etching down to the conducting layer.

In FIG. 13, an oxide etching is carried out to remove the barrier layer at the bottom of the pores and to widen the pore diameter. The wet etch process allows the pores 312 to extend downward to reach the conductive layer. The thickness of the resulted porous oxide layer can be controlled by controlling the processing parameters of aluminum physical vapor deposition (PVD); anodization and the subsequent wet etch processes. The self-assembled pore structure is naturally formed with a hexagonal array. The pore diameter (d) and the inter-pore distance (D) can depend on applied anodization voltage (V), current density (i) and the properties of the electrolyte, and the subsequent pore widening wet etch process.

Figure 14A:
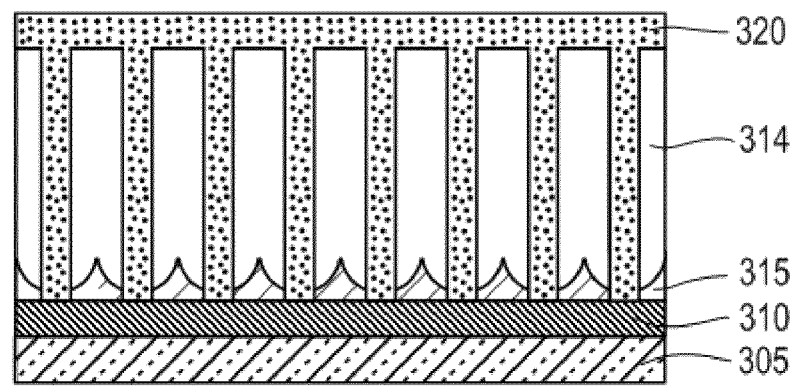
FIG. 14A is a cross-sectional view of the nano structure formed on the multi-layer layer structure after the deposition of a noble metal.
Figure 14B:
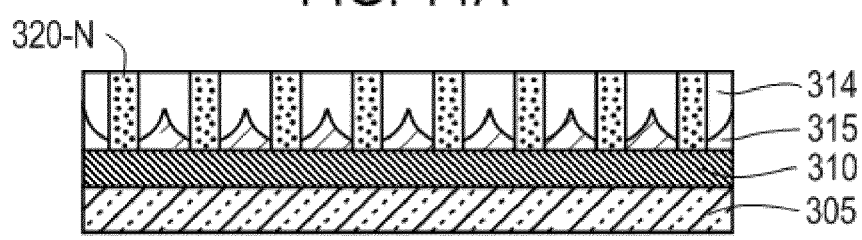
FIG. 14B is a cross-sectional view of the nano structure formed on the multi-layer layer structure after the removal of the noble metal on the top layer.
Figure 15:
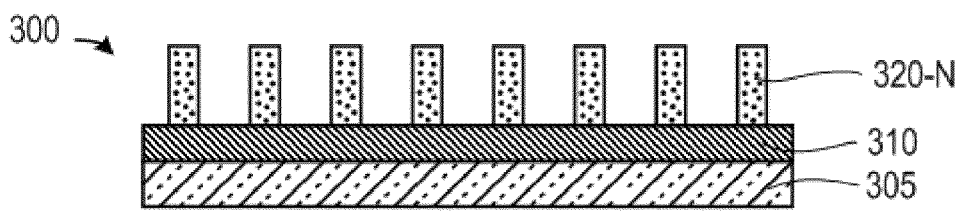
FIG. 15 is a cross-sectional view of the nano structure formed on the multi-layer layer structure after the oxide layer is removed.

Referring to FIG. 14A, a noble metal such as Ag is deposited on the porous layer 315 to fill the pores 312 and to form a layer 320. The layer 320 can be formed by PVD process or electroplating. In FIG. 14B, a layer of the noble metal 320 is removed while leaving the noble metal 320-N in the pores 312. Another wet metal etch or CMP process is applied further control height of the noble metal 320-N filling the pores. In FIG. 15, the aluminum oxide 315 and the residue aluminum film 315-AL at the bottom of the porous aluminum layer 315 are removed to form a nano-structured surface 300 comprising an array of nano rods 320-N.

The nano rods 320-N are substantially straight and are perpendicular to the substrate 305 and the conductive layer 310. The nano rods 320-N can have substantially the same or similar widths. The neighboring nano rods 320-N are separated by gaps that remain substantially constant or close to constant at different distances from the conductive layer 310.

The geometries of the photolithographic masks applied in the above-described fabrication processes are designed to match the expected size of the sensing chip and the area of the metal pad, which locates at the corner of the chip. For field applications, the chemical detection sensing chips are formed as packaged sensing chips by applying different semiconductor packaging technologies, e.g., wire-bonding, flip-chips, system-on chip (SOC), etc.

In some embodiments, nano-structures can be fabricated by a different process as shown in FIGS. 16A to 16F. A two-layer structure 362 includes a conductive layer 335 and a substrate 330. The conductive layer 335 can be made of titanium (Ti) or nickel (Ni), and can be electrically and thermally conductive. The substrate 330 can be an n-type silicon flat wafer (3-8 Ω-cm), or oxidized (30-50 nm $SiO_2$) p-type silicon flat wafers (5-10 mΩ-cm). The thickness of this conductive metal layer 335 can be controlled in the range of 100 Å-1,000 Å. An adhesion layer (which, for example, can be made of Ag) can be deposited to the metal layer 335. The thickness of the conductive layer 335 can be optimized for applying an electric bias to the sensing surface for trace chemical detection and further for applying a lower temperature to the sensing surface to enhance sensitivity of trace chemical detection, or higher temperature to clean the sensing surface.

Figure 16A:
FIGS. 16A-16D, 16G, and 16H are cross-sectional views of the nano structure formed on the multi-layer layer structure after the fabrication process.
Figure 16D:
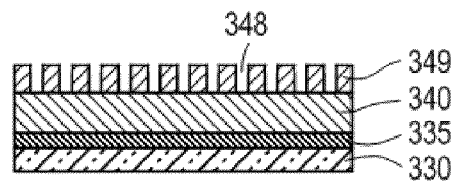
Figure 16B:
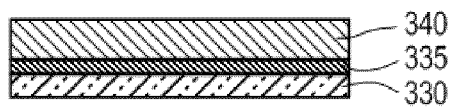

In FIG. 16B, a noble metal layer 340 is deposited on top of the conductive layer 335. The noble metal may be a silver layer, e.g., Ag layer having a thickness of 1 nm-200 nm. In FIG. 16C, a second metal layer 345 is deposited on top of the noble metal layer 340. The second metal layer 345 can include aluminum with a purity level of approximately 99.999% and a thickness in the range of 1.0-10.0 μm. The aluminum layer 345 is then annealed at 400° C.-500° C. in a $N_2$ purged furnace for 2-5 hours to recrystallize the Al film.

In FIG. 16D, an anodization process is carried out to produce a porous structure in a form of porous aluminum oxide 345'. A top view is shown in FIG. 16E where the porous structure is formed with naturally self-assembled hexagon-shaped nano pore-array that includes a plurality of pores 348 surrounded by hexagon-shaped pore wall 349. Neighboring pores 348 have a center-to-center distance D. After removing top anodized layer and the barrier layer by a wet chemical process, a second anodization process is carried out to consume all Al metal so that the barrier layer and top porous $Al_2O_3$ layer 345' are right above the noble metal layer 340.

Then a wet etch process is performed to widen the pores 348 and to remove the barrier layer at the bottom of the pores 348. As the wet etch process proceeds, as shown in FIG. 16F, the pores 348 are widened and the walls 349 surrounding the pore become thinner. The etch process can be controlled to form a plurality of nano-sized pores 348 surrounded by wall 349. Alternatively, the etching of the pores 348 can widen the pores 348 so much such they touch each other, which can produce a hexagonal array of quasi-triangle nano rods 349'.

Figure 16G:
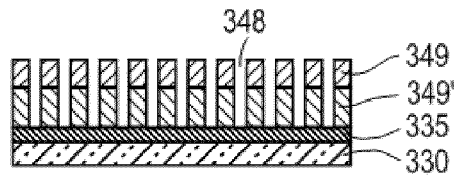
Figure 16C:
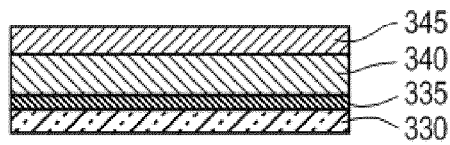
Figure 16H:
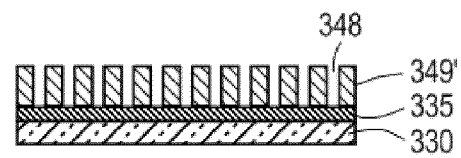
Figure 16F:
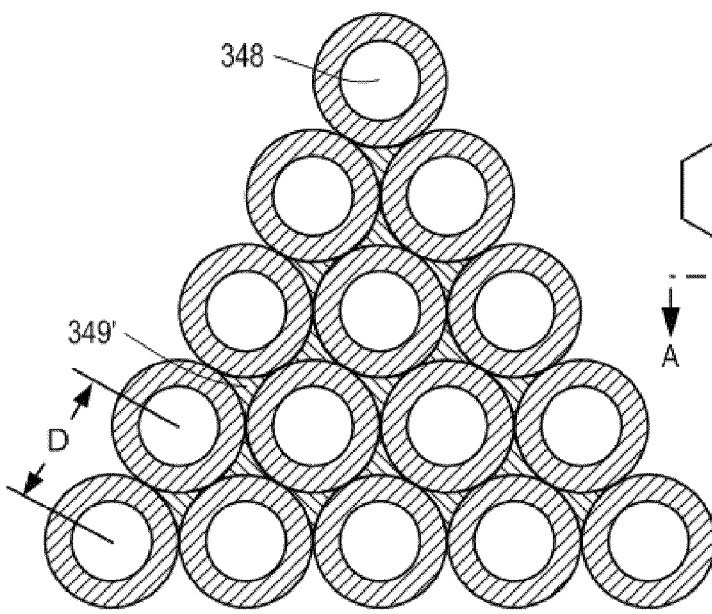
FIGS. 16E and 16F are top views of the nano structure formed on the multi-layer layer structure after the fabrication process.
Figure 16E:
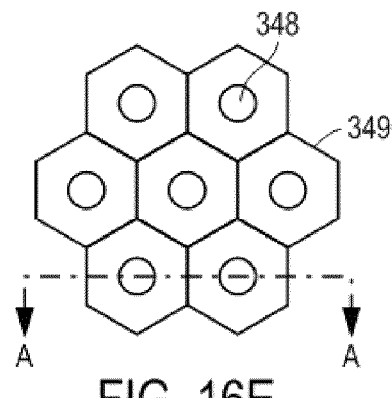

In FIG. 16G, the noble metal layer 340 is etched down and the pores 348 are extended downward to reach the conductive titanium layer 335. In FIG. 16H, a wet oxide etch is performed to remove the aluminum oxide followed by a wet metal etch to remove the aluminum residue at the bottom of the pores 348. The aluminum oxide 315 and the residue aluminum film 315 at the bottom of the porous aluminum layer 315 are removed to form an array of nano rods 349' having controlled heights, diameters and well-defined inter-rod distances. The array can have quasi-triangle periodic cells.

The nano rods are substantially straight and are substantially perpendicular to the substrate 330 and the conductive layer 335. The nano rods can have substantially the same or similar widths. Neighboring nano rods are separated by gaps that remain substantially constant at different distances from the conductive layer 335.

In some embodiments, a sensor compatible with FIGS. 1A and 1C can be prepared by introducing nano particles as described above on a structured or substantially unstructured (i.e. flat) substrate, or a sample solution. The trace chemical or biological substance can first be mixed with the nano particles in a solution to allow molecules of the trace chemical or biological substance to be adsorbed onto the nano particles. The sample solution containing the nano particles are then introduced onto the structured or unstructured surface of the chemical sensor. In other words, nano surface structures can be prepared by coating the surface of the sensor 105 by a solution containing a colloidal suspension of nano particles. The nano particles can be formed by a metallic materials (such as Al, Ag, Au, Cu, Fe, Co, Ni, Cr, Zn, Sn, Pd, Pt, and their alloys), oxide material (such as titanium oxide, silicon oxide, zinc oxide, etc), or a polymeric material. Oxide or polymeric particles can be doped with metal ions or coated with a conductive material. The colloidal suspension can include single nano particles or clusters of nano particles. A nano surface structure is formed after the solution applied to the sensor surface. The solution can evaporate, leaving the nano particles adsorbed with the target molecules on the sensor surface.

Healthcare Applications of Nano-Structure Based Spectral Sensing

In some embodiments, diseases can be identified by analyzing Raman spectra obtained from body fluids from a patient using the light scattering probe 100 as described above in relation to FIGS. 1A-2, 6B, 7-9B. A body fluid obtained from an individual person can be directly introduced onto a sensor (e.g., 105 in FIG. 1A) or mixed in a sample solution (e.g., 720 in FIG. 7) containing nano particles. Light scattering and Raman spectral analyses can be conducted as shown in FIGS. 1A-1C or in FIG. 7. Alternatively, the sample solution containing the nano particles can be introduced on a structured or unstructured surface of a sensor, as described above, which is used in subsequent light scattering and Raman spectral analysis.

Figure 17:
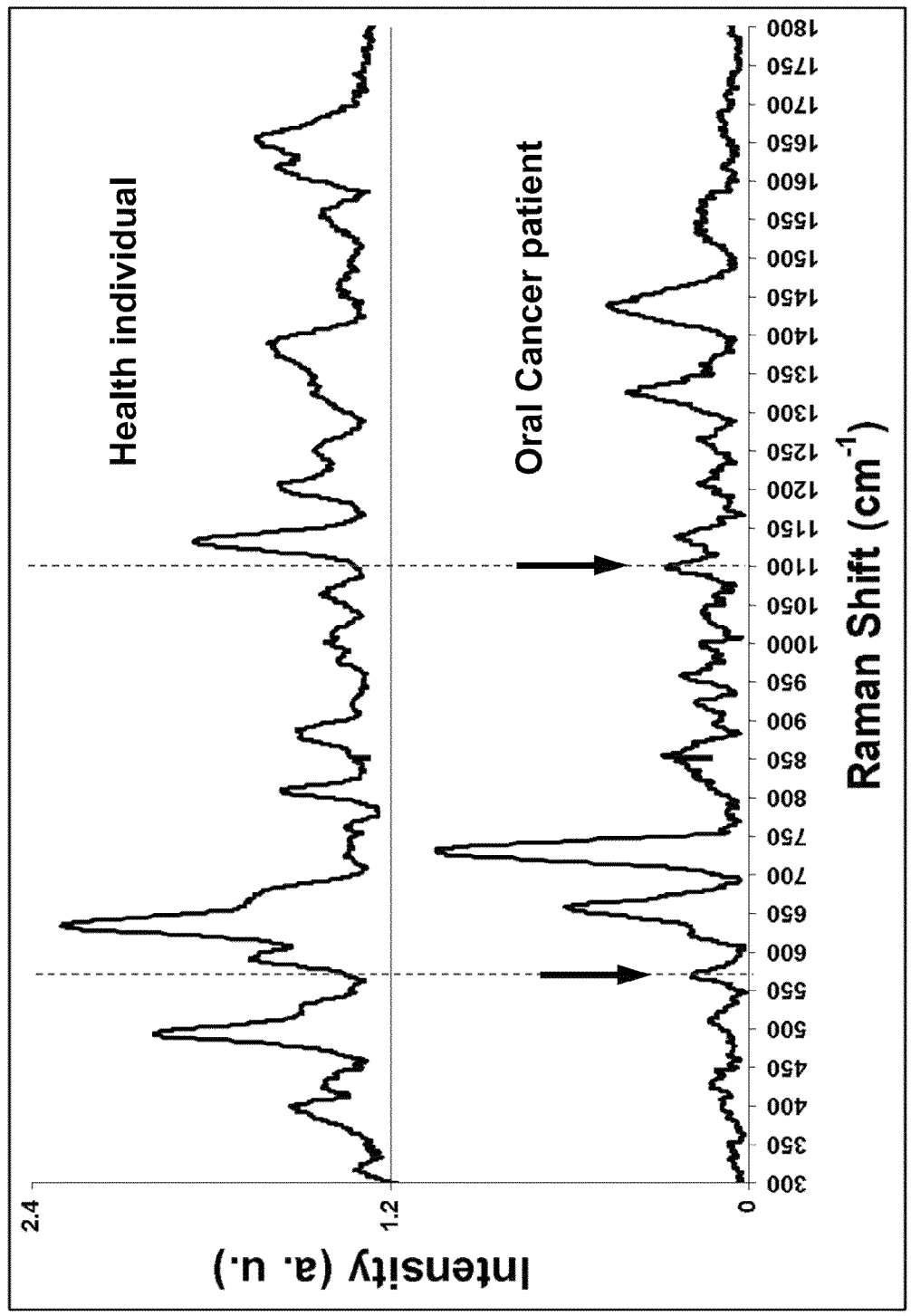
FIG. 17 illustrates an exemplified Raman spectral signature for oral cancer detected in the saliva of an oral cancer patient by the disclosed Raman scattering probe.

Referring to FIG. 17, the Raman spectrum obtained from a saliva sample from an oral cancer patient shows two signature spectral peaks respectively around, for example, 560 cm$^{-1}$ (in the region from 520 cm$^{-1}$ to 580 cm$^{-1}$) and 1100 cm$^{-1}$ (in the region from 1080 cm$^{-1}$ to 1110 cm$^{-1}$) which are absent in a healthy individual without the oral cancer. The signature spectral peaks around 560 cm$^{-1}$ and 1100 cm$^{-1}$ are associated with molecular vibrations for C—S, S—S, O—P—O (PO$_2$), C—N, or C—C bonds in, for example, cysteine, ATP, ADP, DNA, RNA, proteins, and other phosphate containing biological compounds. The identification of these spectral signatures can include the steps: a spectral band is first selected at Raman peaks with Raman shift in unit of cm$^{-1}$ (wavenumber) of each spectral signature. A background scattering intensity level is determined. The peak intensity level, relative intensity or integrated area of the peak, is calculated. A signal-to-noise ratio is calculated using the peak intensity and the background level. If the signal-to-noise ratio is higher than a predetermined threshold (e.g., 3 or higher), the spectral signature of a Raman peak is positively identified. The identification of spectral signatures for detecting diseases and drug use can be assigned by statistical analysis and several computation algorithms such as dendrograph classification and Principal Component Analysis. A patient can be diagnosed with oral cancer or at an early stage of an oral cancer if spectral signatures around 560 cm$^{-1}$ and 1100 cm$^{-1}$ are both identified. Appropriate doctors and patients themselves may be alerted for further testing using the same or other types of diagnosis techniques.

Figure 18:
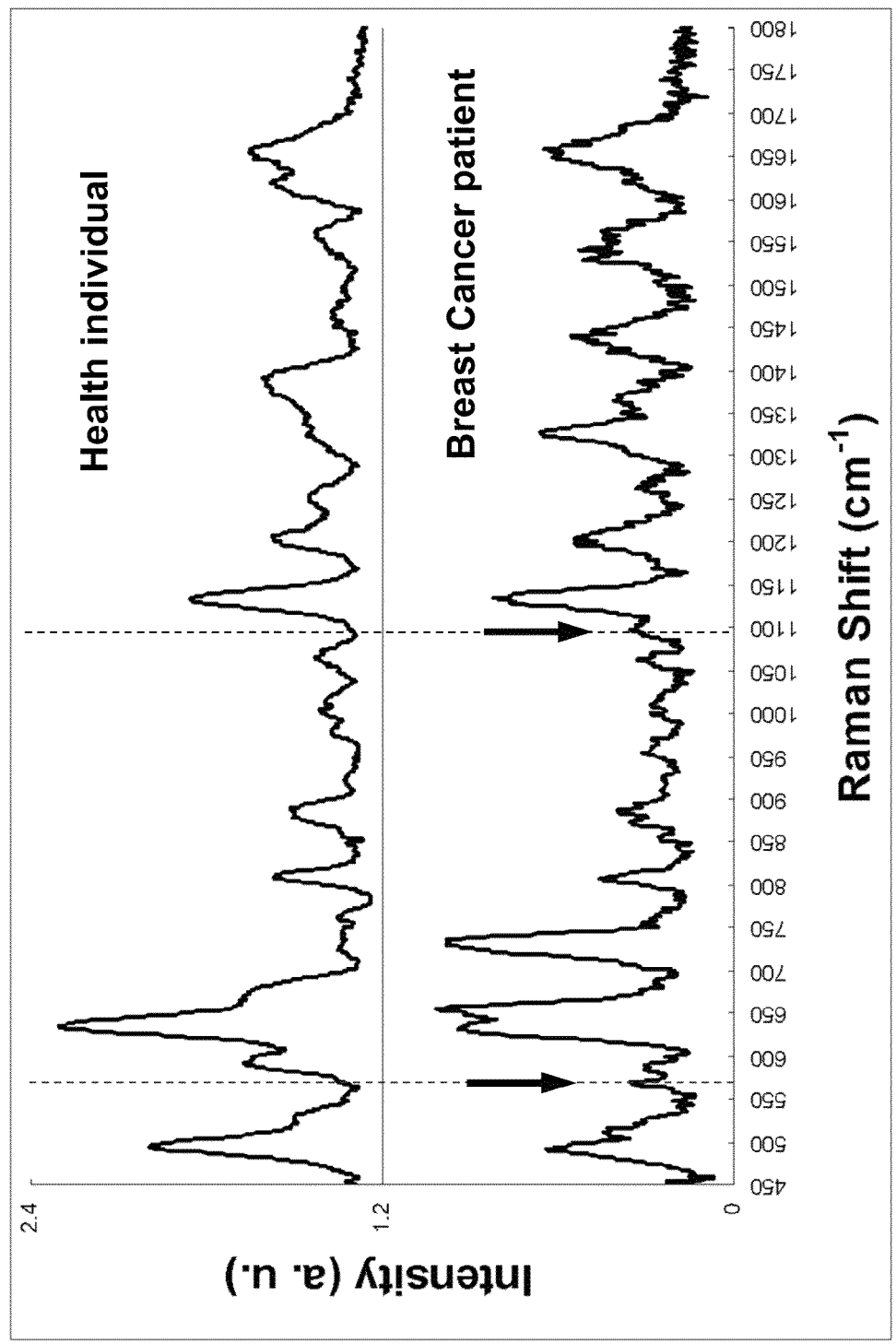
FIG. 18 illustrates an exemplified Raman spectral signature for breast cancer detected in the saliva of a breast cancer patient by the disclosed Raman scattering probe.
Figure 19A:
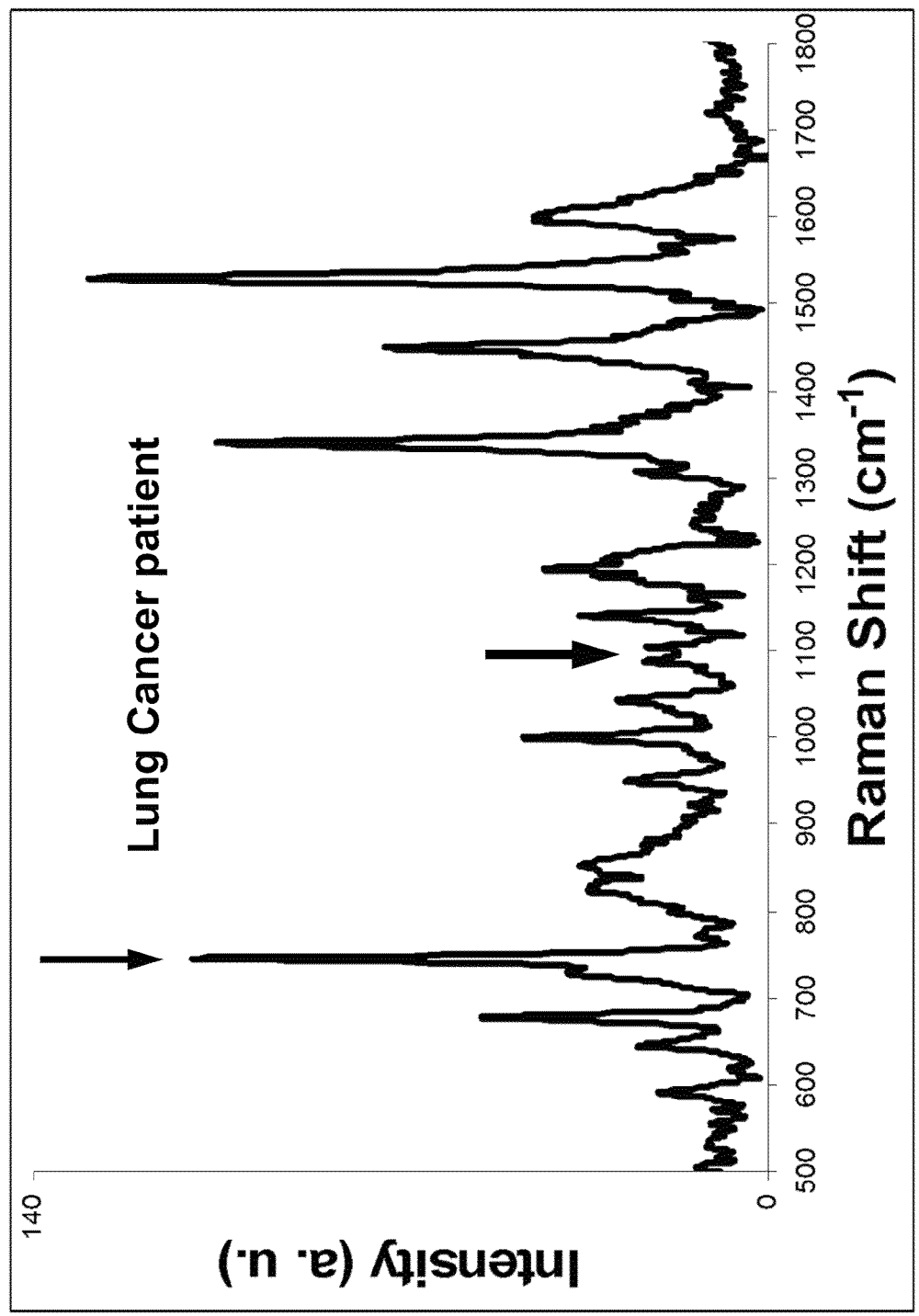
FIGS. 19A and 19B illustrate an exemplified Raman spectral signature for lung cancer detected in both the saliva and the serum of a lung cancer patient using the disclosed Raman scattering probe.
Figure 19B:
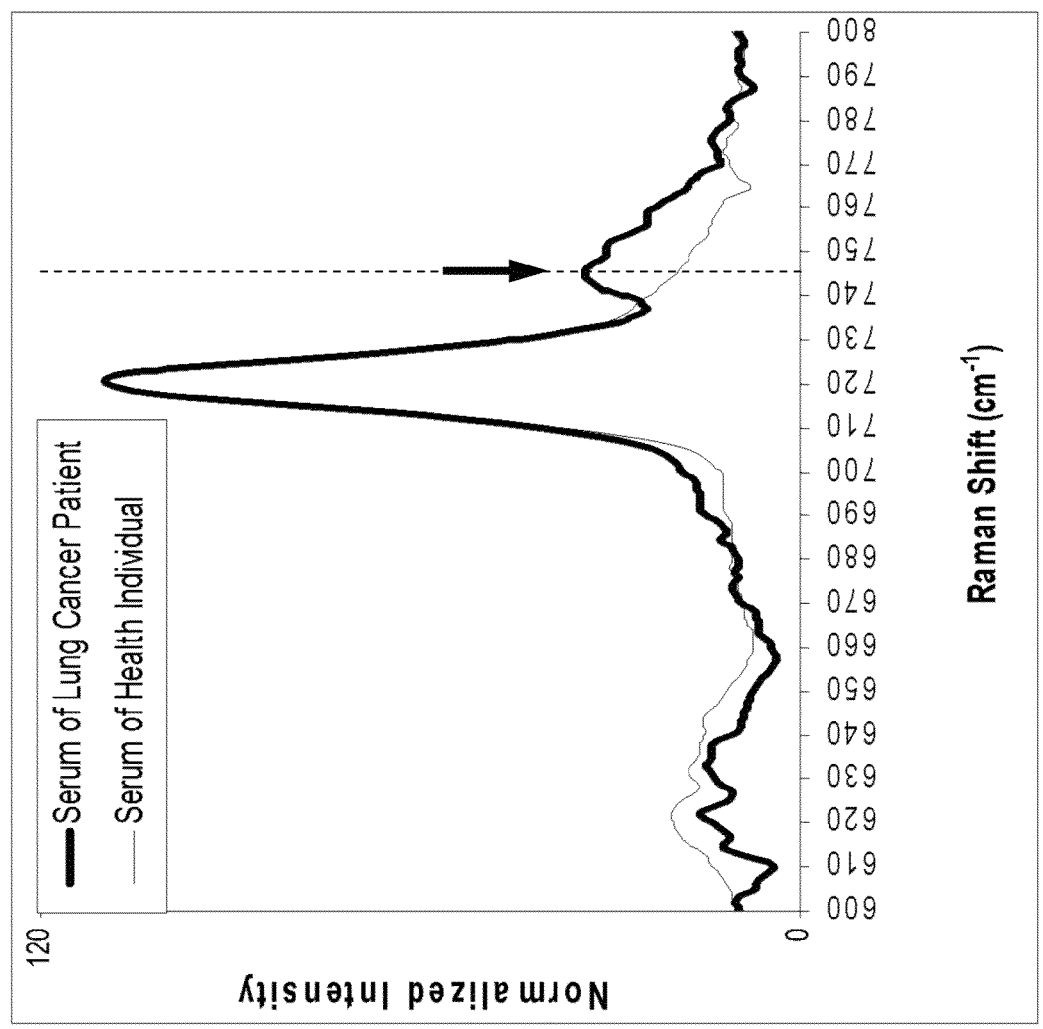
Figure 20:
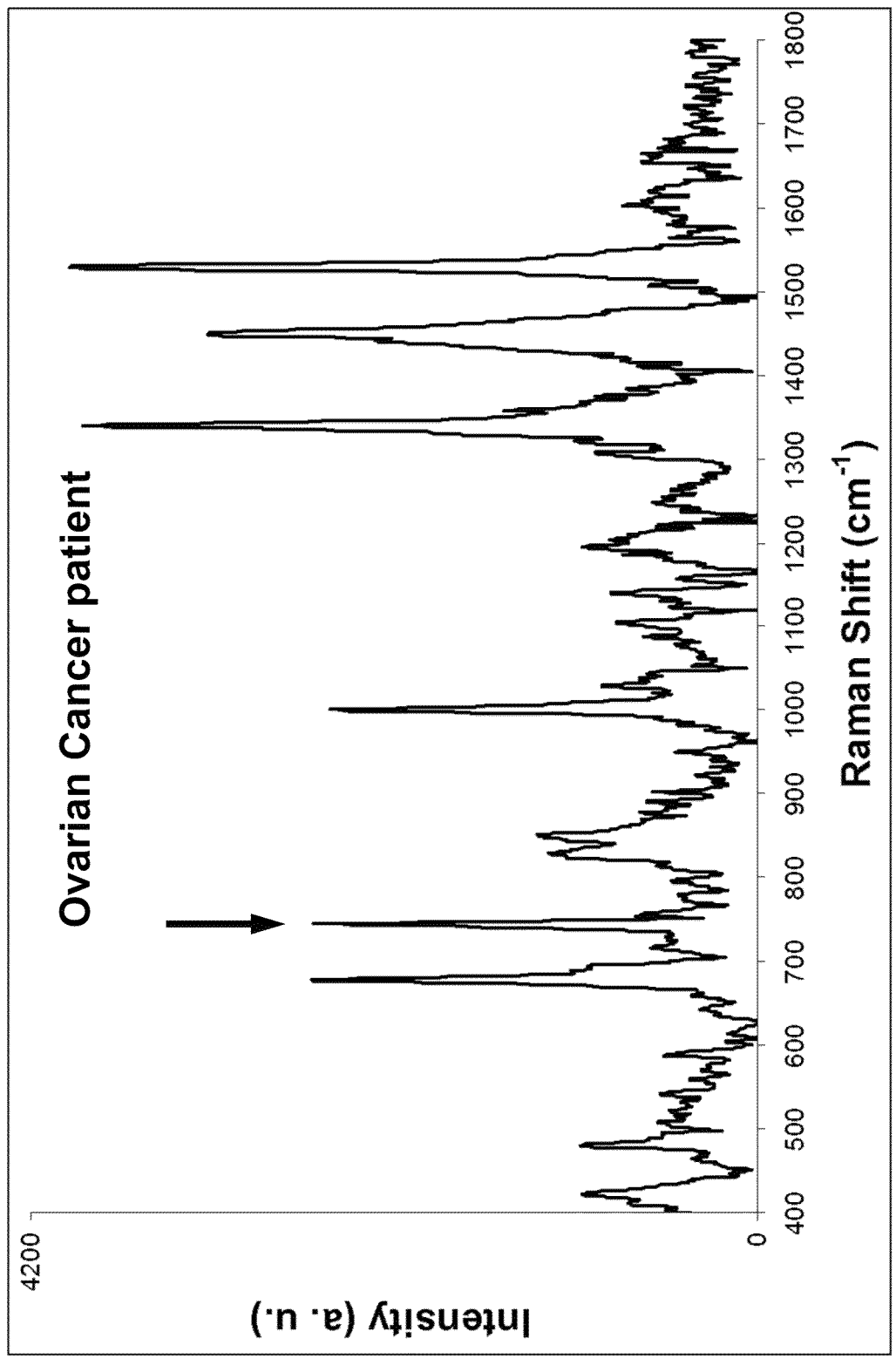
FIG. 20 illustrates an exemplified Raman spectral signature for ovarian cancer detected in the serum of an ovarian cancer patient by the disclosed Raman scattering probe.
Figure 21:
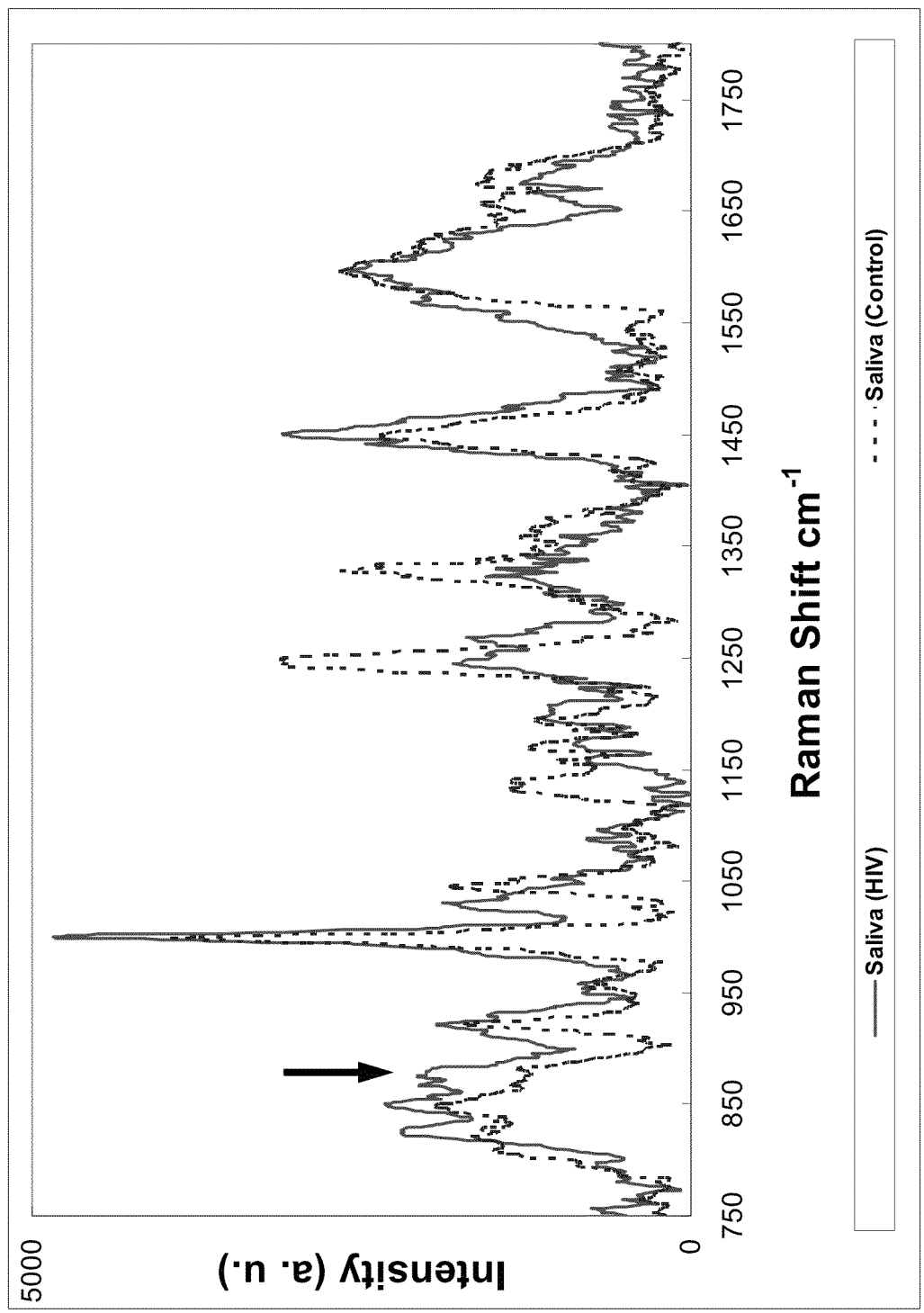
FIG. 21 illustrates an exemplified Raman spectral signature for HIV detected in the saliva of an HIV patient by the disclosed Raman scattering probe.
Figure 22:
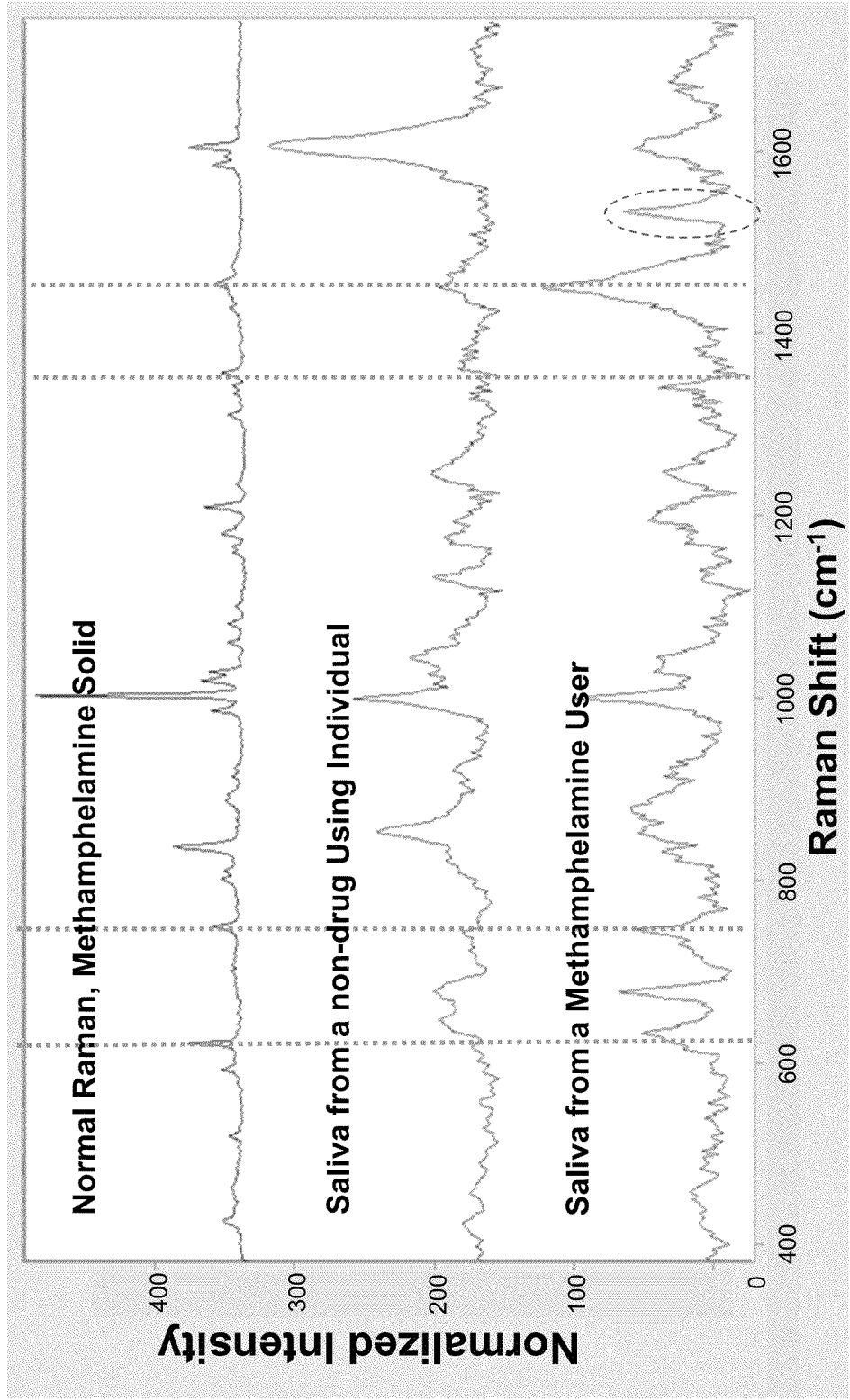
FIG. 22 illustrates an exemplified Raman spectral signature for illicit drug use detected in the saliva of an illicit drug user by the disclosed Raman scattering probe.

The disclosed systems and methods can also be used to estimate glucose level so that to evaluate diabetes status. A signature spectral peak in the region from 1115 cm$^{-1}$ to 1135 cm$^{-1}$, for example, around 1124 cm$^{-1}$, which is associated with molecular vibration of glucose, in a Raman spectrum obtained from a saliva sample from a diabetes patient can provide key evidence for diagnosing diabetes. The intensity, relative intensity or integrated area of this Raman peak, can be used to evaluate glucose concentration of a body fluid from a patient to score potential diabetes level. Similarly, referring to FIGS. 18-20, breast cancer can also show spectral signatures in Raman spectrum obtained from saliva around 560 cm$^{-1}$ and 1100 cm$^{-1}$ (FIG. 18). Saliva and serum samples obtained from lung cancer and ovarian cancer patients can have a Raman spectral signature at around 745 cm$^{-1}$ (in the range from about 740 cm$^{-1}$ to about 760 cm$^{-1}$) (FIGS. 19 and 20). The signature spectral peak around 745 cm$^{-1}$ is associated with molecular vibrations for C—S bonds in phosphate, O—P—O vibration in Z-DNA, T-DNA, or S, N or P contained atomic or molecular groups. HIV can have a spectral signature in Raman spectrum obtained from a serum sample in the region of 865 cm$^{-1}$-885 cm$^{-1}$, for example, around 870 cm$^{-1}$ (FIG. 21). The disclosed systems and methods can also be used to identify illicit drug such as heroin, methamphetamine cocaine, caffeine, morphine, codeine, amphetamine, ephedrine, papaverine, narcotine, acetyl codeine, methamphetamine HCl, ketamine HCl, codeine H$_3$PO$_4$, meperidine HCl (pethidine), triazolam, secobarbital, hypaconitine, MDMA, etc. FIG. 22 shows Raman spectra from a methamphetamine solid (a type of illicit drug), a saliva sample of a non-drug using individual, and a methamphetamine drug user. The Raman spectrum from a drug-user's saliva sample shows a characteristic peak at around 1030 cm$^{-1}$ and 1535 cm$^{-1}$, which can be used to indicate illicit drug use. The disclosed methods and systems can also be used to detect doping (e.g., hormone) in athletes during international sports competitions such as the Olympic Games.

Figure 23:
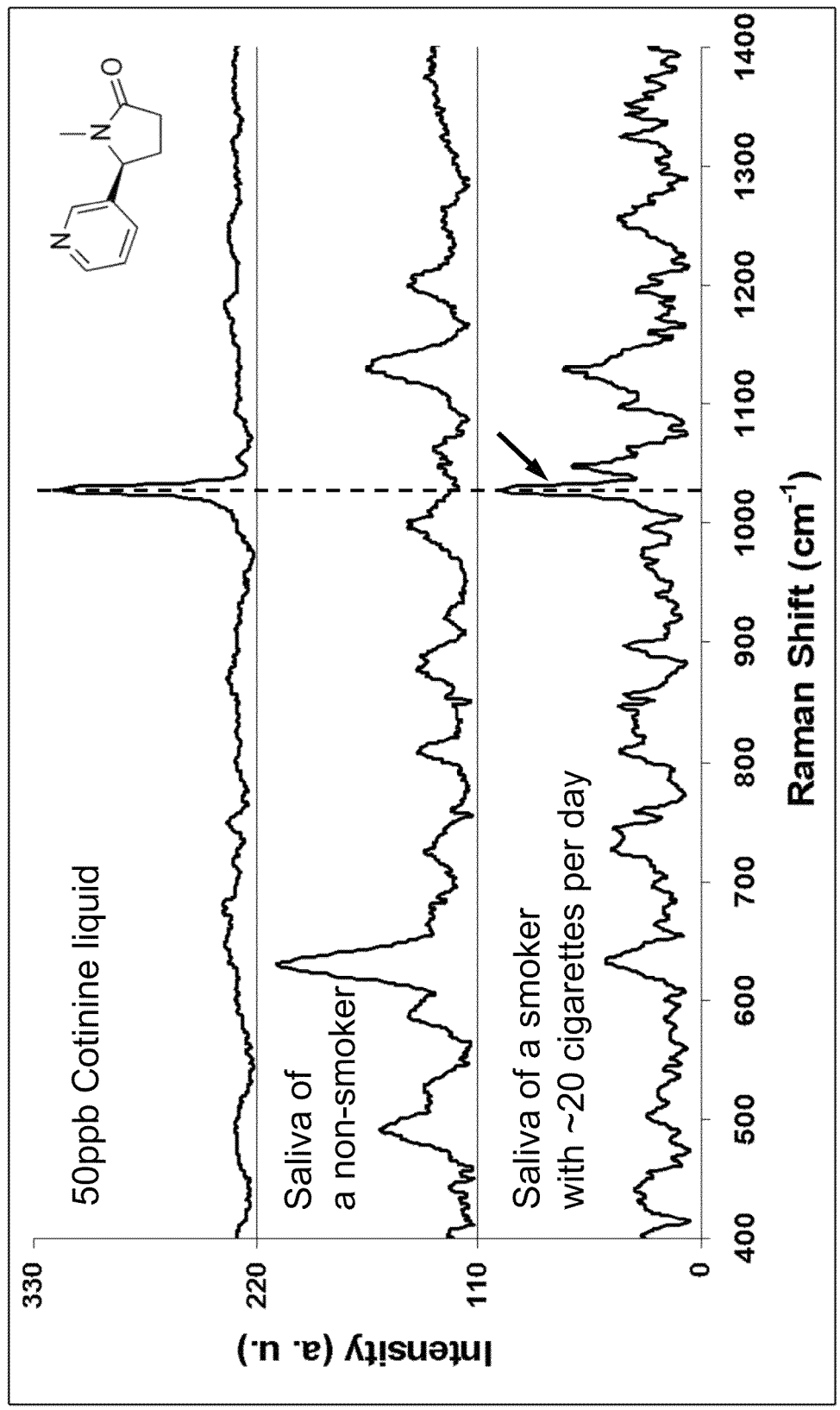
FIG. 23 illustrates an exemplified Raman spectral signature for the smoking status detected in the saliva of a smoker by the disclosed Raman scattering probe, with a comparison of a Raman spectral signature of the cotinine which is the metabolite of nicotine.

Similarly, referring to FIG. 23, smoking status or secondary smoking status can also show spectral signature at around 1029 cm$^{-1}$ in a Raman spectrum obtained from a saliva sample of a smoker, which is absent in a non-smoking healthy individual. The signature spectral peaks around 1029 cm$^{-1}$ is associated with molecular vibration mode of cotinine which is metabolite of nicotine.

Figure 24:
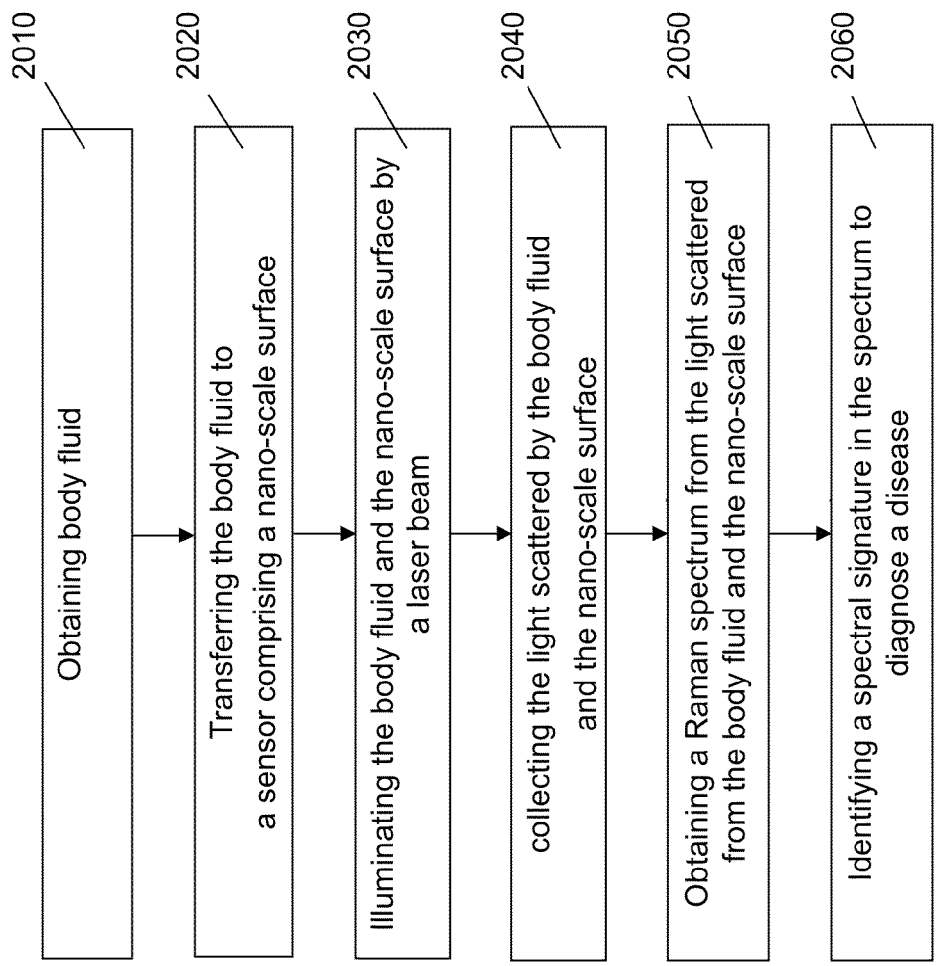
FIG. 24 is a flowchart for non-invasive disease diagnosis using the disclosed Raman scattering probe.

The non-invasive disease detection and diagnosis using the disclosed Raman scattering probe can include one of more of the following steps: referring to FIG. 24, a body fluid is first obtained from a patient or an illicit drug user (step 2010). Due to the high sensitivity of the disclosed Raman scattering sensors, the amount body fluid can be rather small. For example, the volume of the body fluid obtained from the patient can be in a range from about 100 pl to 4 ml. Examples of the body fluid can include blood, saliva, urine, serum, tear, sweat, stomach fluid, hydrothorax, ascites, CSF, sperm, and a secrete body fluid. After centrifuge, the body fluid is next introduced to a nano-scale surface (step 2020). For example, the nano-scale surface can include nano-scale structures on the surface of a sensor. The body fluid can be transferred to the nano-scale surface on the sensor. The body fluid can be left to dry up and remain a dried layer on the sensor surface. In another example, the nano-scale surfaces are provided by the surfaces of nano particles suspended in a solution. The body fluid can be introduced to the solution comprising the nano particles. Molecules in the body fluid are adsorbed to the nano-scale surface. A laser beam is applied to illuminate the nano-scale surface and the molecules adsorbed onto the nano-scale surface (step 2030). Light scattered by the nano-scale surface and the adsorbed molecules is collected (step 2040).

A Raman spectrum is obtained from the scattered light (step 2050). One or more spectral signatures are identified in the spectrum to diagnose a disease (step 2060). Examples of the diseases that can be detected include cancers including but not limited to lung cancer, breast cancer, stomach cancer, esophageal cancer, thyroid cancer, larynx cancer, ulcer cancer, ovarian cancer, liver cancer, head and neck cancers, uterus cancer, cervix cancer, oral cancer, leukemia, colon cancer, bladder cancer, prostate cancer, skin cancer, bronchus cancer, and liver cirrhosis, a failing kidney, HIV, and drug addiction. As previously described, the one or more spectral signatures are at predetermined Raman shift in the Raman spectrum. The Raman shifts and the characteristics of the spectral signatures are specific to the disease to be detected. For example, spectral signatures for oral and breast cancers in a saliva sample can be at around 560 cm$^{-1}$ or 1100 cm$^{-1}$. A spectral signature for lung cancer in a serum sample can be at around 745 cm$^{-1}$ in the Raman spectrum. A spectral signature can include a spectral peak. The spectral signature can be identified when the spectral peak is above certain threshold. For example, a signal-to-noise ratio of the spectral peak relative to the noise background can be above 3 for the spectral signature to be positively identified.

It should be noted that the steps illustrated in FIG. 24 is compatible with and can incorporate one or more steps shown in FIG. 8, which involves using a sample solution containing nano particles.

Nano-Structure Based Spectral Sensing in Biological Immunoassay

In some embodiments, the disclosed light scattering probe and substance detection methods are applicable to biological immunoassay. Specifically, nano-structure enhanced Raman spectral analysis can be applied to detect an antibody or an antigen as an analyte using immunoassays such as enzyme-linked immunosorbent assay (ELISA) or enzyme immunoassay (EIA).

Figure 25:
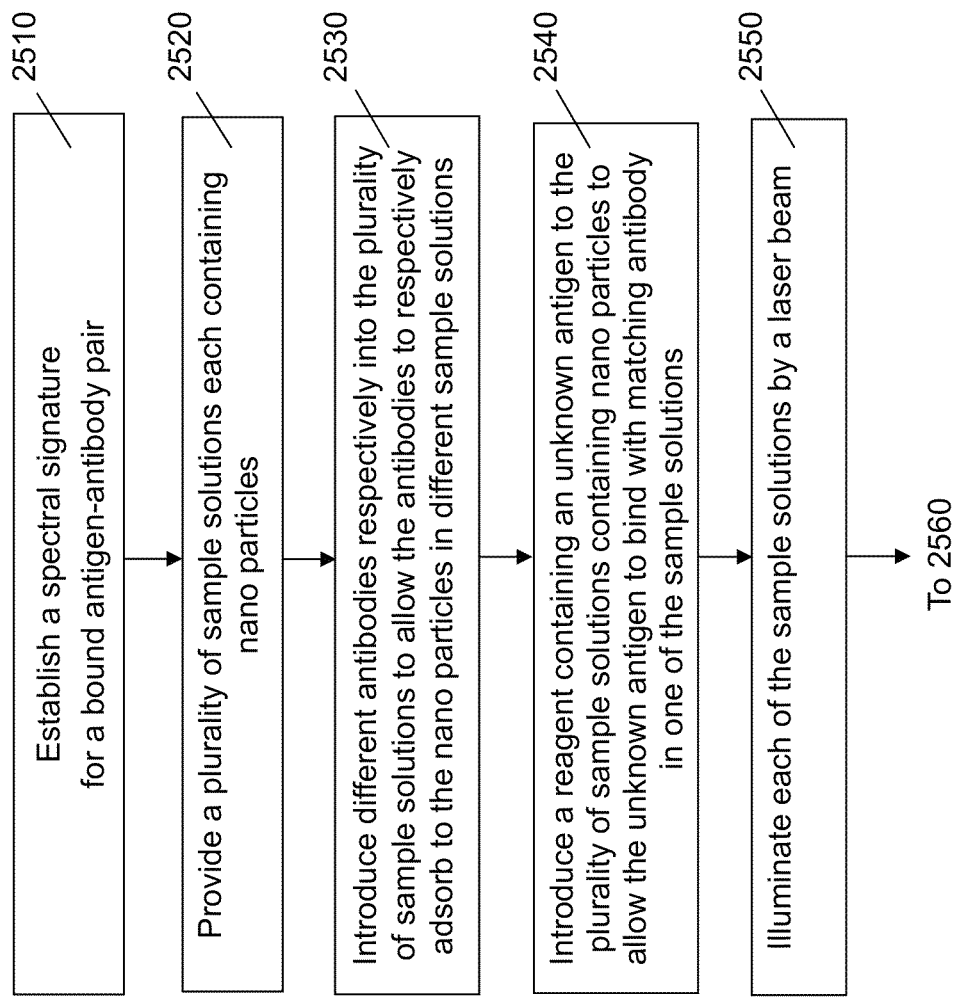
FIG. 25 is a flowchart for a process for detecting an unknown antigen using immunoassay utilizing nano-structure based spectral sensing in accordance to the present invention.
Figure 25:
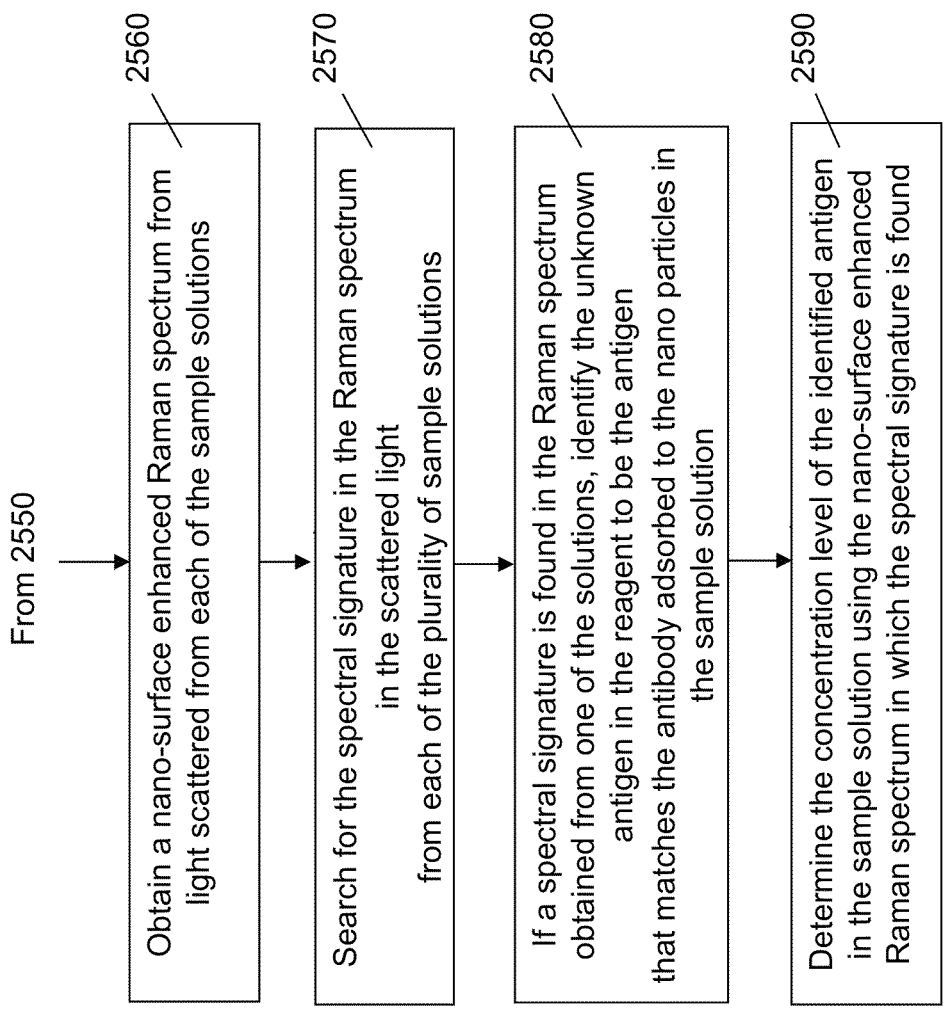

Referring to FIG. 25, a method for substance identification can include the follow steps: a known antigen is bound with different antibodies adsorbed to nano surface structures to form different antigen-antibody pairs on the nano surface structures. Spectral signatures are established in Raman spectra obtained from the different antigen-antibody pairs on each of the nano surface structures (step 2510). In some embodiments, spectral markers (e.g. Raman markers) such as MBA are introduced to bind with the antigen or antibody before analyte detection to provide signatures in Raman spectra. For example, main NERS signatures for MBA are located at 520 $cm^{-1}$, 1072 $cm^{-1}$, and 1588 $cm^{-1}$. The spectral signatures are determined in similar manners to spectral signatures described above in FIGS. 17-23 related to diseases. A spectral signature can include one or more spectral peaks, one or more spectral valleys, and other spectral shapes such as relative peak height, peak line width, and peak shape which can be used to characterize one or more molecular bonds in a biological, medical, or chemical substance. The biological, medical, or chemical substance can include antigen that can trigger the production of antibodies by human immune systems.

Antibodies, also known as immunoglobulins, are gamma globulin proteins found in blood or other bodily fluids of vertebrates. They are used by the immune system to identify and neutralize foreign objects, such as bacteria and viruses. They are typically made of basic structural units—each with two large heavy chains and two small light chains—to form, for example, monomers with one unit, dimers with two units or pentamers with five units. Antibodies are produced by a type of white blood cell called a plasma cell. There are several different types of antibody heavy chains, and several different kinds of antibodies, which are grouped into different isotypes based on which heavy chain they possess. Five different antibody isotypes are known in mammals, which perform different roles, and help direct the appropriate immune response for each different type of foreign object they encounter.

Though the general structure of all antibodies is very similar, a small region at the tip of the protein is extremely variable, allowing millions of antibodies with slightly different tip structures, or antigen binding sites, to exist. This region is known as the hypervariable region. Each of these variants can bind to a different target, known as an antigen. A huge diversity of antibodies allows the immune system to recognize an equally wide variety of antigens. The unique part of the antigen recognized by an antibody is called the epitope. These epitopes bind with their antibody in a highly specific interaction, called induced fit, which allows antibodies to identify and bind only their unique antigen in the midst of the millions of different molecules that make up an organism. Recognition of an antigen by an antibody tags it for attack by other parts of the immune system. Antibodies can also neutralize targets directly by, for example, binding to a part of a pathogen that it needs to cause an infection.

Examples of antigens compatible with the presently disclosed methods and systems includes clenbuterol, nitrofurans, organic phosphorus, organochlorine, pro terephthalate, a pesticide, a rodenticide, a substance in a veterinary drug, an arsenic compound, or a cyanide.

The target molecules can include, small molecules and metallic elements such as illicit drugs (heroin, methamphetamine, cocaine, caffeine, morphine, codeine, amphetamine, ephedrine, papaverine, narcotine, and MDMA. etc.), nitrofuran, clenbuterol, chloramphenicol, olaquindox and the heavy metals harmful substances mercury, lead, cadmium.

It should be noted that although the process below describes an unknown antigen as an analyte and a known antibody is previously bound to a nano structured surface for detecting the antigen, the reverse process is applicable to the systems and processes described below: unknown antibody can be an analyte and a known antigen is prepared to be bound to a nano structured surface for detecting the unknown antibody.

Figure 26A:
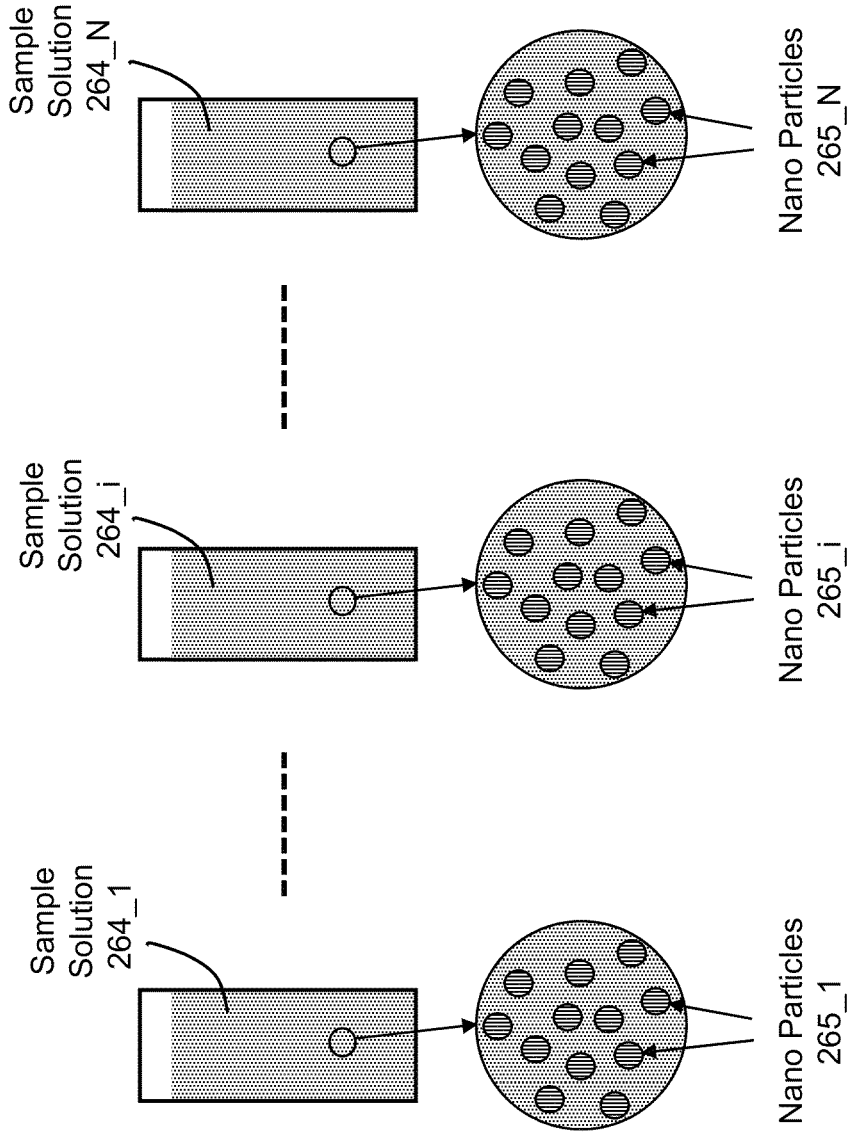
FIG. 26A illustrates sample preparations for immunoassay utilizing nano particles based spectral sensing as described by the process in FIG. 25.

In order to detect and identify an unknown antigen, a plurality of sample solutions 264_1 . . . 264_i, . . . 264_N are provided, as shown in FIG. 26A. Each of the solutions 264_1 . . . 264_i, . . . 264_N contains suspension of nano particles 265_1 . . . 265_i, . . . 265_N (step 2520). The nano particles 265_1 . . . 265_i, . . . 265_N can have in round or irregular shapes. The average dimension of the nano particles 265_1 . . . 265_i, . . . 265_N can be in a range from about 1 nm to about 1000 nm. As described above in relation to FIGS. 9A and 9B, the size distribution of the nano particles 265_1 . . . 265_i, . . . 265_N can be characterized by average particle dimension and particle-dimension distribution width. The nano particles 265_1 . . . 265_i, . . . 265_N can include a material selected from a group consisting of a metal, a metal alloy, an oxide material, silicon, a polymeric material, and a combination thereof. The nano particles 265_1 . . . 265_i, . . . 265_N can include a material selected from a group consisting of Al, Ag, Au, Cu, Fe, Co, Ni, Cr, Zn, Sn, Pd, Pt, and a combination thereof. The nano particles 265_1 . . . 265_i, . . . 265_N can include a material selected from a group consisting of titanium oxide, silicon oxide, and zinc oxide. The nano particles 265_1 . . . 265_i, . . . 265_N can also include carbon nano tubes. To enhance spectral strength of Raman scattering, the sample solution can include multivalence ions. The nano particles 265_1 . . . 265_i, . . . 265_N can include a magnetic or ferromagnetic material.

Figure 26B:
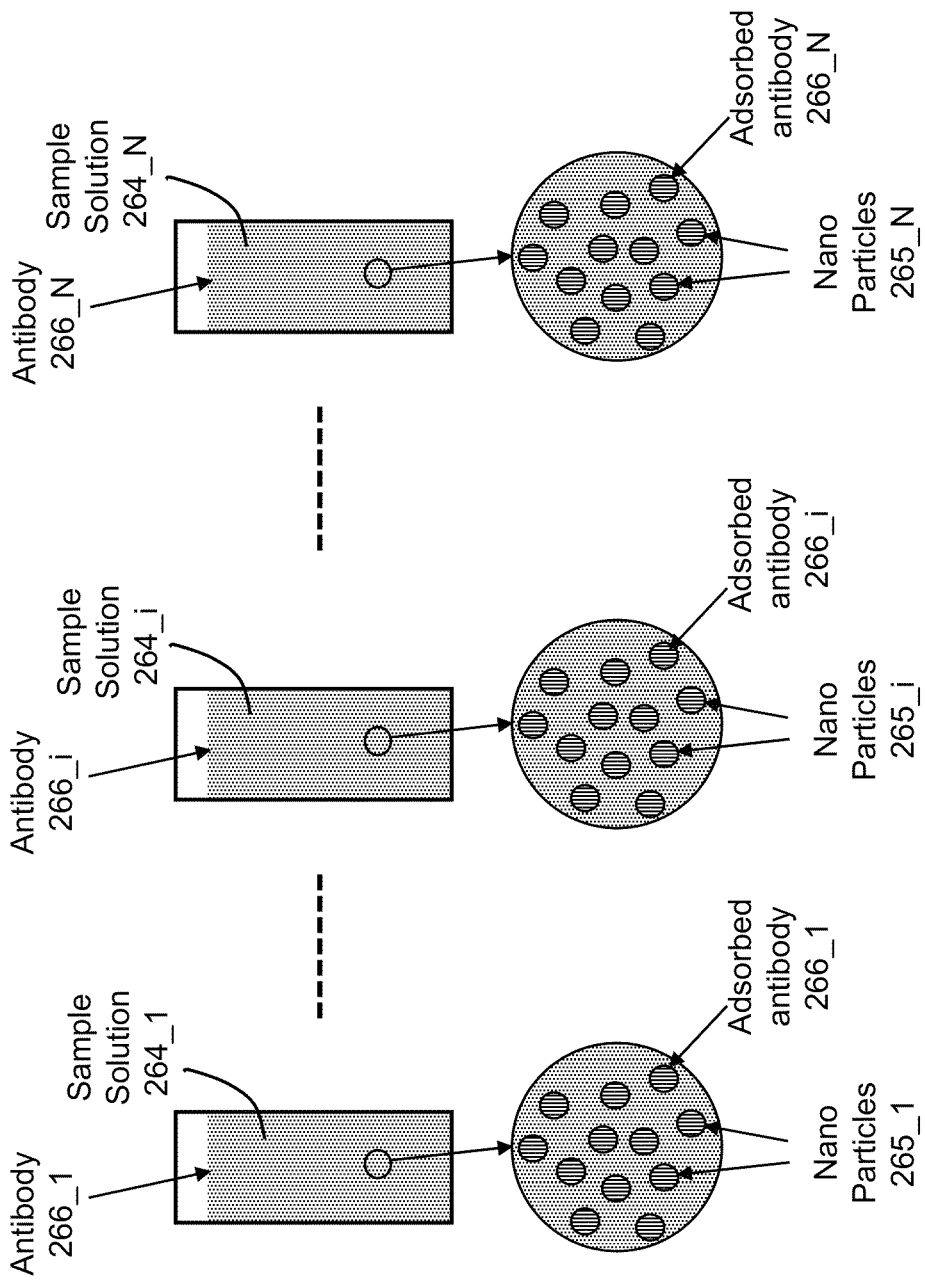
FIG. 26B illustrates spectral measurements from the samples comprising nano particles adsorbed with antibodies as described by the process in FIG. 25.

Referring to FIGS. 25 and 26B, different unknown antibodies 266_1 . . . 266_i, . . . 266_N are separately introduced to the sample solutions 264_1 . . . 264_i, . . . 264_N to allow the different antibodies 266_1 . . . 266_i, . . . 266_N to respectively adsorb to the nano particles 265_1 . . . 265_i, . . . 265_N in different sample solutions 264_1 . . . 264_i, . . . 264_N (step 2530). The different antibodies 266_1 . . . 266_i, . . . 266_N can be selected according to the types of antigens that are to be detected. For example, the unknown antigen can belong to the group of clenbuterol, nitrofurans, organic phosphorus, organochlorine, pro terephthalate, a pesticide, a rodenticide, a substance in a veterinary drug, an arsenic compound, or a cyanide. The antibodies of these antigens are respectively introduced into the sample solutions 264_1 . . . 264_i, . . . 264_N with each sample solution 264_i receiving a different type of antibody 266_i.

Figure 26C:
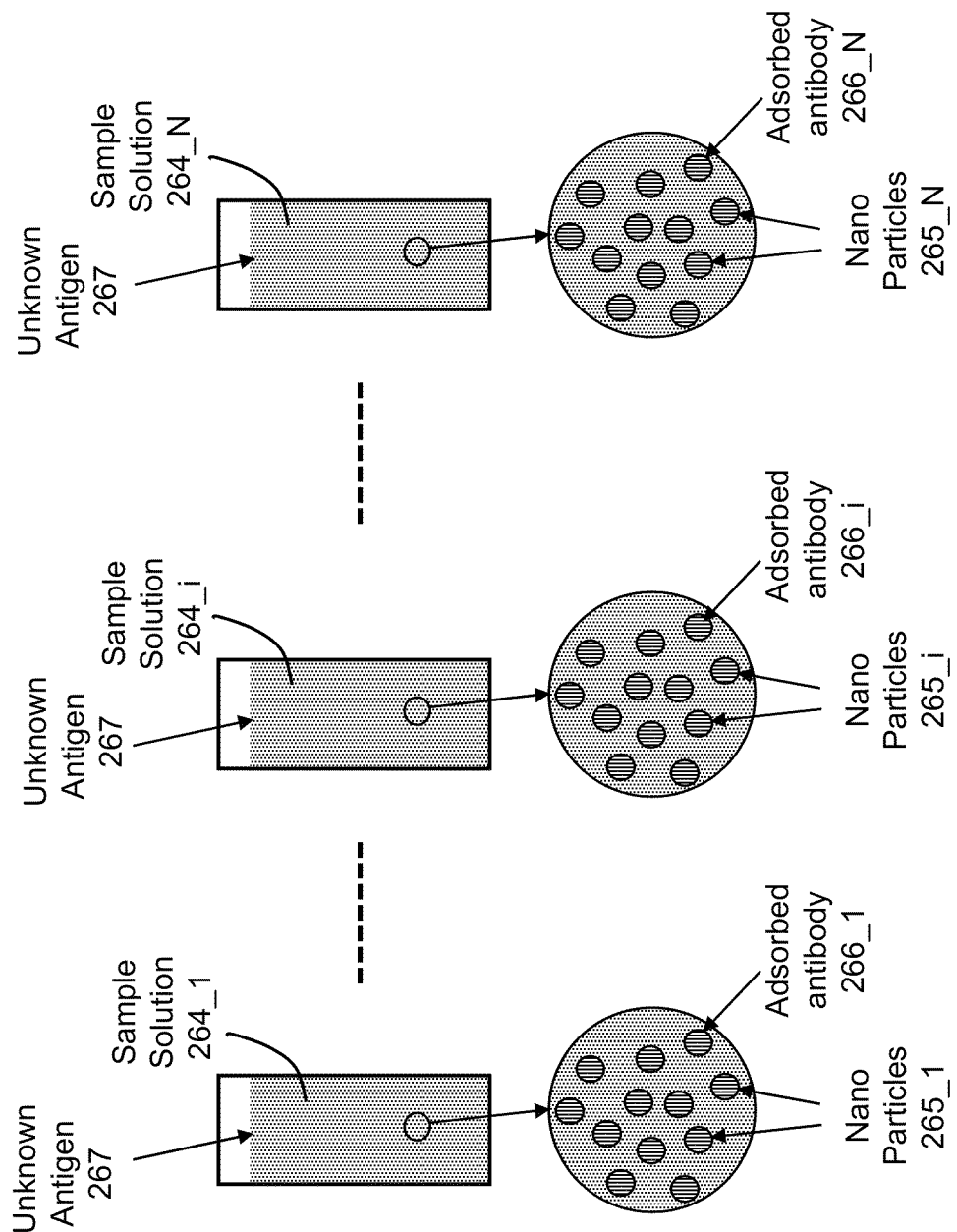
FIG. 26C shows to-be-detected unknown antigens being introduced into the samples comprising nano particles adsorbed with antibodies as described by the process in FIG. 25.

Next, referring to FIGS. 25 and 26C, a reagent containing an unknown antigen 267 (i.e. the analyte) is introduced to the sample solutions 264_1 . . . 264_i, . . . 264_N containing nano particles 265_1 . . . 265_i, . . . 265_N to allow the unknown antigen 267 to bind with matching antibody 266_i in one of the solutions (step 2540). The antigen 267 can be one of the exemplified substrate as described above. Other examples for the antigen 267 can include melamine, sodium cyclamate, sodium cyclohexylsulfamate, cane sugar, starch, nitrite, nitrate, Sudan I, II, III and IV, malachite green, methomidophos, acephate, DDT, DDV, malathion, fenitrothion, deltamethrin, cypermethrin, methyl parathion, phosmet, phorate, dimethoate, nitrofuran, furanzolidole, AOZ, heavy metal, lead (Pb), cadmium (Cd), mercury (Hg), chromium (Cr), arsenic (As), chloramphenicol, chlortetracycline, chloromycetin, ciprofloxacin, enorfloxacin, clenbuterol, ractopamine, salbutamol, penicillin, bisphenol A, DEHP, 6-benzylaminopurine, or olaquindox, which can be a regulated substance in food product.

The reagent can be extracted from a food product. The food product can include dairy products, candies, cookies, drinks, alcohol, meat, seafood, tea, fresh or canned vegetables, fruits, grain products, cereals, corn chips, potato chips, or protein containing food. Examples of the dairy products include milk, milk powders, cheese, cheese-containing cakes, yogurts, ice creams, milk containing candies, or cookies. The reagent can also be extracted from an illicit drug substance selected from a group consisting of heroin, methamphetamine, cocaine, caffeine, morphine, codeine, amphetamine, ephedrine, papaverine, narcotine, and MDMA.

Figure 26D:
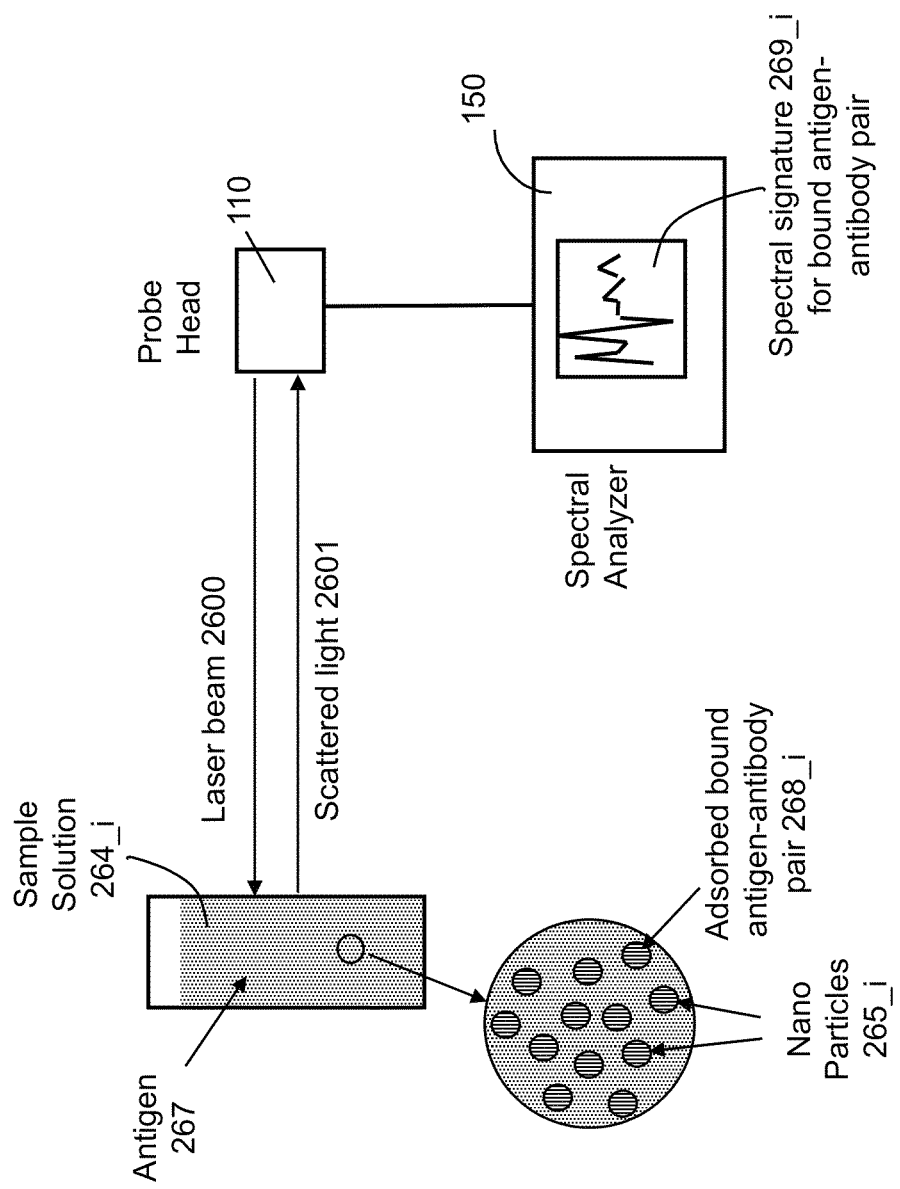
FIG. 26D shows detection of the unknown antigens bound to the antibodies adsorbed to the nano particles as described by the process in FIG. 25.

Referring to FIGS. 25 and 26D, each of the sample solutions $264\_1 \ldots 264\_i, \ldots 264\_N$ containing the unknown antigen 267 and the nano particles $265\_1 \ldots 265\_i, \ldots 265\_N$ adsorbed with the different antibodies $266\_1 \ldots 266\_i, \ldots 266\_N$ is respectively illuminated by a laser beam 2600 (step 2550). The laser beam 2600 can be emitted by a laser device in a probe head 110. The scattered light 2601 from each of the sample solutions $264\_1 \ldots 264\_i, \ldots 264\_N$ can be respectively collected by the probe head 110. A nano-surface enhanced Raman spectrum is obtained from light scattered 2601 by a spectral analyzer 150 for each of the sample solutions $264\_1 \ldots 264\_i, \ldots 264\_N$ (step 2560).

The spectral signature for bound antigen-antibody pair is searched in each of the Raman spectra obtained from the sample solutions $264\_1 \ldots 264\_i, \ldots 264\_N$ (step 2570). Similar to the description above in relation to FIG. 17, the identification of a spectral signature for a bound antigen-antibody pair can include the steps: a spectral band is first selected around a Raman spectral peak(s) for the spectral signature. A background scattering intensity level is determined. The peak intensity level, relative intensity or integrated area of the peak, is calculated. A signal-to-noise ratio is calculated using the peak intensity and the background level. If the signal-to-noise ratio is higher than a predetermined threshold (e.g., 3 or higher), the spectral signature of a Raman peak can be positively identified.

If a spectral signature for an antigen-antibody pair $268\_i$ (or the associated Raman marker molecule as described above) is found in the Raman spectrum obtained from one of the sample solutions $264\_i$, the unknown antigen 267 in the reagent can be identified to be the antigen that matches the antibody $266\_i$ adsorbed to the nano particles $265\_i$ in the sample solution $264\_i$ (step 2580). Due to the key-lock nature between antigens and antibodies, the Raman spectra obtained from other sample solutions would not exhibit spectral signatures for their respective antigen-antibody pairs. To increase confidence and reduce the interference in the spectral background noise, the spectral signature can be verified by obtaining nano-structure enhanced Raman scattering in a plurality of the sample solutions $264\_i$ having nano particles adsorbed with the antibody $266\_i$ and applied with the reagent containing the unknown antigen 267.

In some embodiments, an electrical field, a magnetic field, or an electro-magnetic field can be applied to the sample solutions containing the nano surface structures (i.e. nano particles) when the scattered light is collected. The electrical field and the magnetic field can be DC or alternating field. These fields have been observed to increase the signal strength of the nano surface enhanced Raman signals.

Moreover, the concentration level of the antigen 267 identified in the sample solution ($264\_i$) can be determined using the nano-surface enhanced Raman spectrum in which the spectral signature is found (step 2590). The concentration level of the antigen 267 in the sample solution can for example be determined using the intensity, the relative intensity, or the integrated area of the spectral signature such as a spectral peak.

The identification of antigens using biological immunoassay and Raman spectral analysis can be enhanced using other nano surface structures than nano particles. For example, the nano surface structures can include nano structures constructed or formed on a substrate. The nano structures can include protrusions or columns formed on an upper surface of the substrate, and recesses or holes formed in an upper surface of the substrate. The neighboring protrusions or columns can have average distances in a range from 10 nanometers to 1000 nanometers. The neighboring recesses or holes have average distances in a range from 10 nanometers to 1000 nanometers. The protrusions can also be formed by nano particles introduced or deposited on a surface of a substrate. The nano particles can have widths in the range from 1 nm to 1000 nm.

Figure 27:
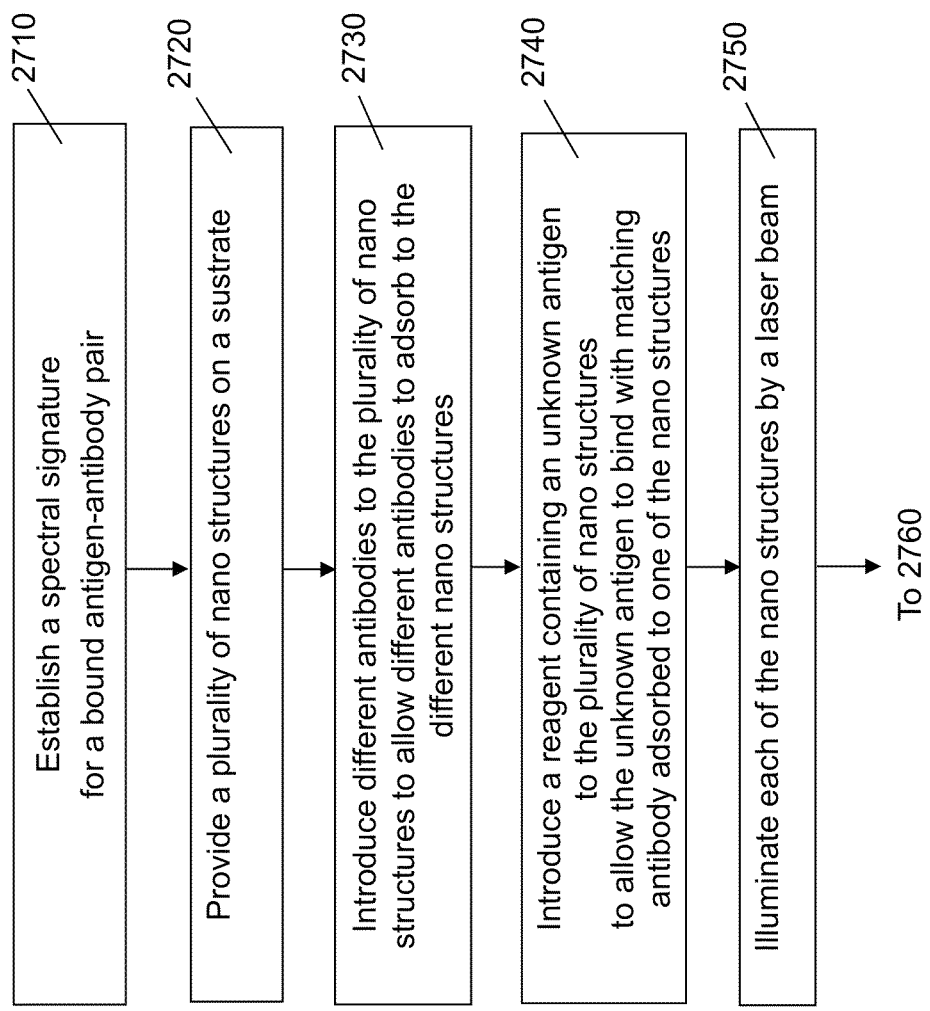
FIG. 27 is a flowchart for another process for detecting an unknown antigen using immunoassay utilizing nano-structure based spectral sensing in accordance to the present invention.
Figure 27:
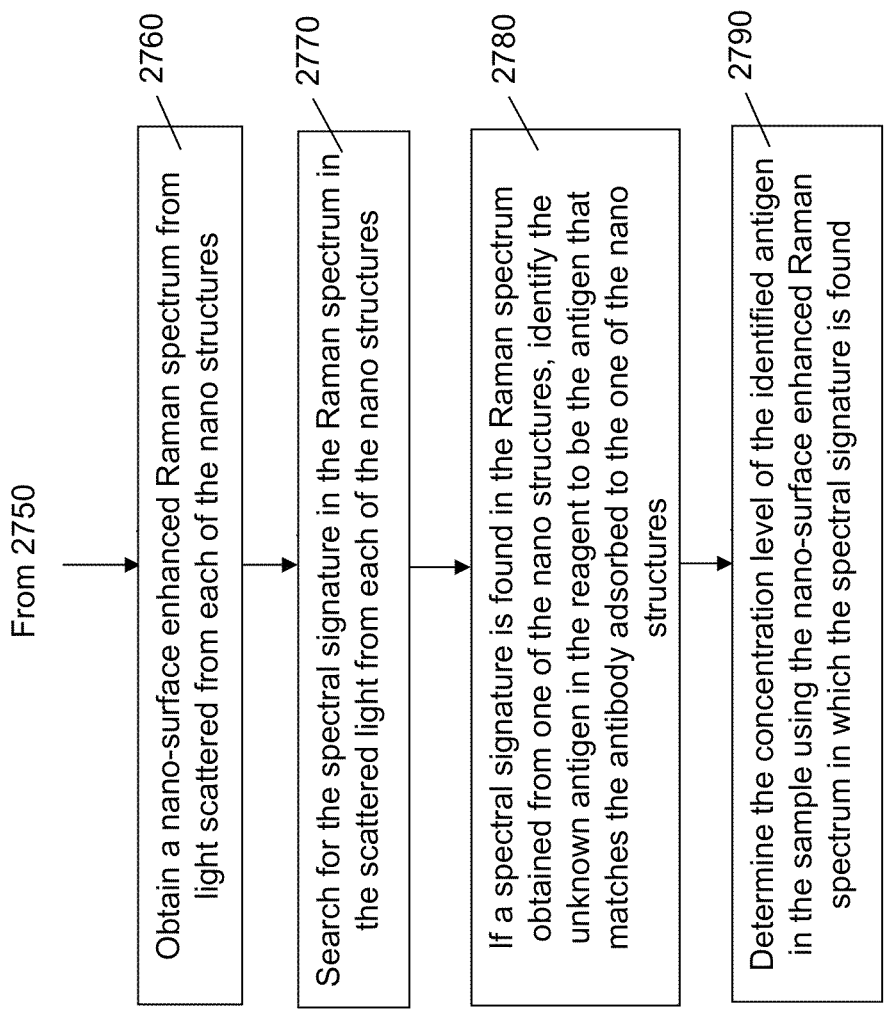

Referring to FIG. 27, spectral signatures are first established in Raman spectra obtained from different antigen-antibody pairs adsorbed to nano surface structures (step 2710). The antigen-antibody pairs are formed by binding a known antigen with antibodies adsorbed to nano surface structures. Examples of antigens compatible with the presently disclosed methods and systems includes clenbuterol, nitrofurans, organic phosphorus, organochlorine, pro terephthalate, a pesticide, a rodenticide, a substance in a veterinary drug, an arsenic compound, or a cyanide.

Figure 28A:
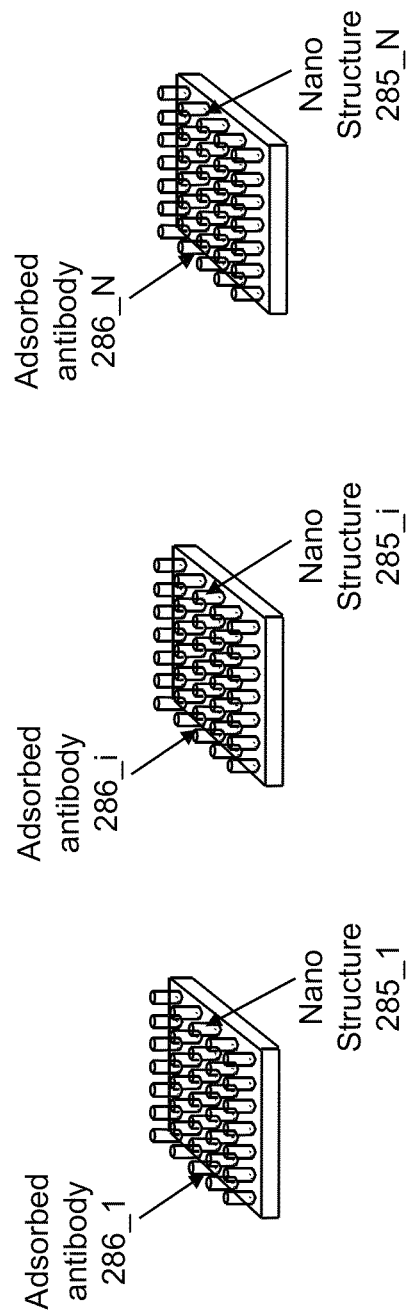
FIG. 28A illustrates the configuration of sample preparation for immunoassay utilizing nano-structure based spectral sensing as described by the process in FIG. 27.
Figure 28B:
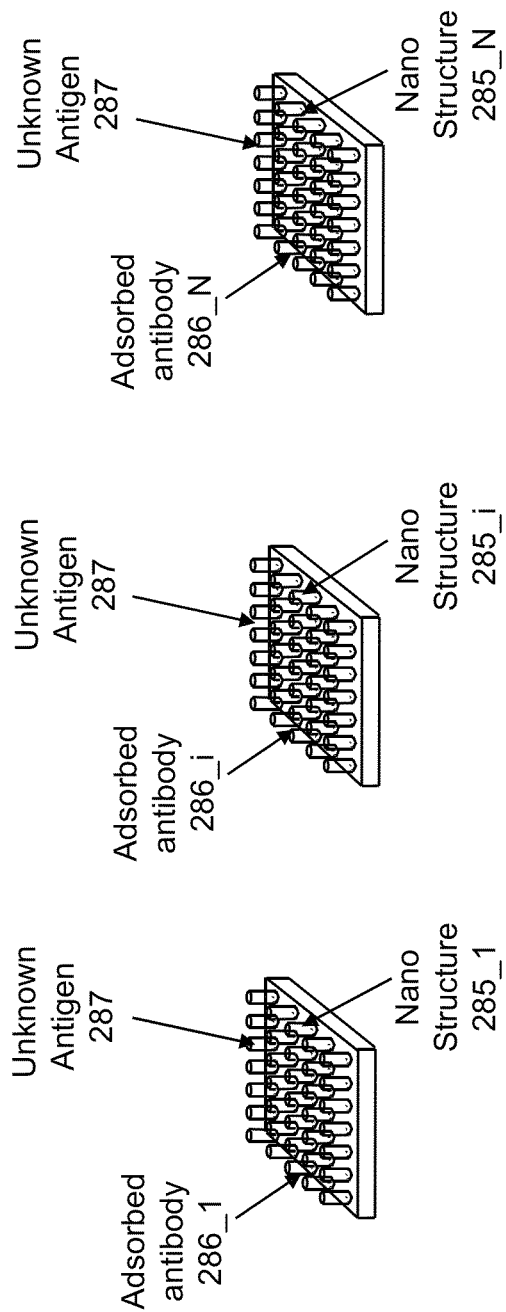
FIG. 28B illustrates the configuration of spectral measurement from the samples comprising nano-structure adsorbed with antibodies as described by the process in FIG. 27.

In order to detect and identify an unknown antigen, a plurality of nano structures $285\_1 \ldots 285\_i, \ldots 285\_N$ are provided on substrates, as shown in FIG. 28A (step 2720). Next, as shown in FIG. 28B, different antibodies $286\_1 \ldots 286\_i, \ldots 286\_N$ are separately introduced to the nano structures $285\_1 \ldots 285\_i, \ldots 285\_N$ to allow the different antibodies $286\_1 \ldots 286\_i, \ldots 286\_N$ to respectively adsorb to the surfaces of the nano structures $285\_1 \ldots 285\_i, \ldots 285\_N$ (step 2730). The adsorption can be assisted by first applying a wetting solution prior to the introductions of the antibodies $286\_1 \ldots 286\_i, \ldots 286\_N$ to the nano structures $285\_1 \ldots 285\_i, \ldots 285\_N$. The different antibodies $286\_1 \ldots 286\_i, \ldots 286\_N$ can be selected according to the types of antigens to be detected. For example, the unknown antigen can belong to the group of clenbuterol, nitrofurans, organic phosphorus, organochlorine, pro terephthalate, a pesticide, a rodenticide, a substance in a veterinary drug, an arsenic compound, or cyanide.

Next, referring to FIGS. 27 and 28B, a reagent containing an unknown antigen 287 is introduced to the nano structures $285\_1 \ldots 285\_i, \ldots 285\_N$ to allow the unknown antigen 287 to bind with matching antibody $266\_i$ on one of the nano structures $285\_1 \ldots 285\_i, \ldots 285\_N$ (step 2740). The antigen 287 can be one of the exemplified substrate as described above. The reagent can be extracted from a food product. The food product can include dairy products, candies, cookies, drinks, alcohol, meat, seafood, tea, fresh or canned vegetables, fruits, grain products, cereals, corn chips, potato chips, or protein containing food. Examples of the dairy products include milk, milk powders, cheese, cheese-containing cakes, yogurts, ice creams, milk containing candies, or cookies. Other examples for the antigen can 287 include melamine, sodium cyclamate, sodium cyclohexylsulfamate, cane sugar, starch, nitrite, nitrate, Sudan I, II, III and IV, malachite green, methomidophos, acephate, DDT, DDV, malathion, fenitrothion, deltamethrin, cypermethrin, methyl parathion, phosmet, phorate, dimethoate, nitrofuran, furanzolidole, chloramphenicol, chlortetracycline, chloromycetin, ciprofloxacin, enorfloxacin, clenbuterol, or 6-benzylaminopurine, which can include regulated substances in food products.

The reagent can also be extracted from an illicit drug substance selected from a group consisting of heroin, methamphetamine, cocaine, caffeine, morphine, codeine, amphetamine, ephedrine, papaverine, narcotine, and MDMA.

Another exemplified controlled substance compatible with the present methods is ketamine. Ketamine is a human and veterinary medicine that has applications in anesthesia, asthmatics, antidepressant, treatment of addiction, and treatment of complex pain syndrome. Ketamine is also the main substance in a widely spread illicit drug called "K powder" (ketamine hydrochloride), which can cause hallucinations and other psychological effects. Ketamine is a small molecule that cannot directly trigger immunological reactions and the production of associated antibodies. Ketamine, however, can be chemically modified to produce p-NH2-Ketamine, which allows them to bind to a protein carrier such as Hemocyanin (KLH), Bovine serum albumin (BSA), Ovalbumin, and γ-Globulin etc. These protein carriers bound with Ketamine have antigen functions and can trigger immunological reactions and production of antibodies in human or animal bodies. The detection of these protein carriers using the antigen-antibody pairing and the nano structure enhanced Raman scattering can therefore lead to the identification of Ketamine.

Figure 28C:
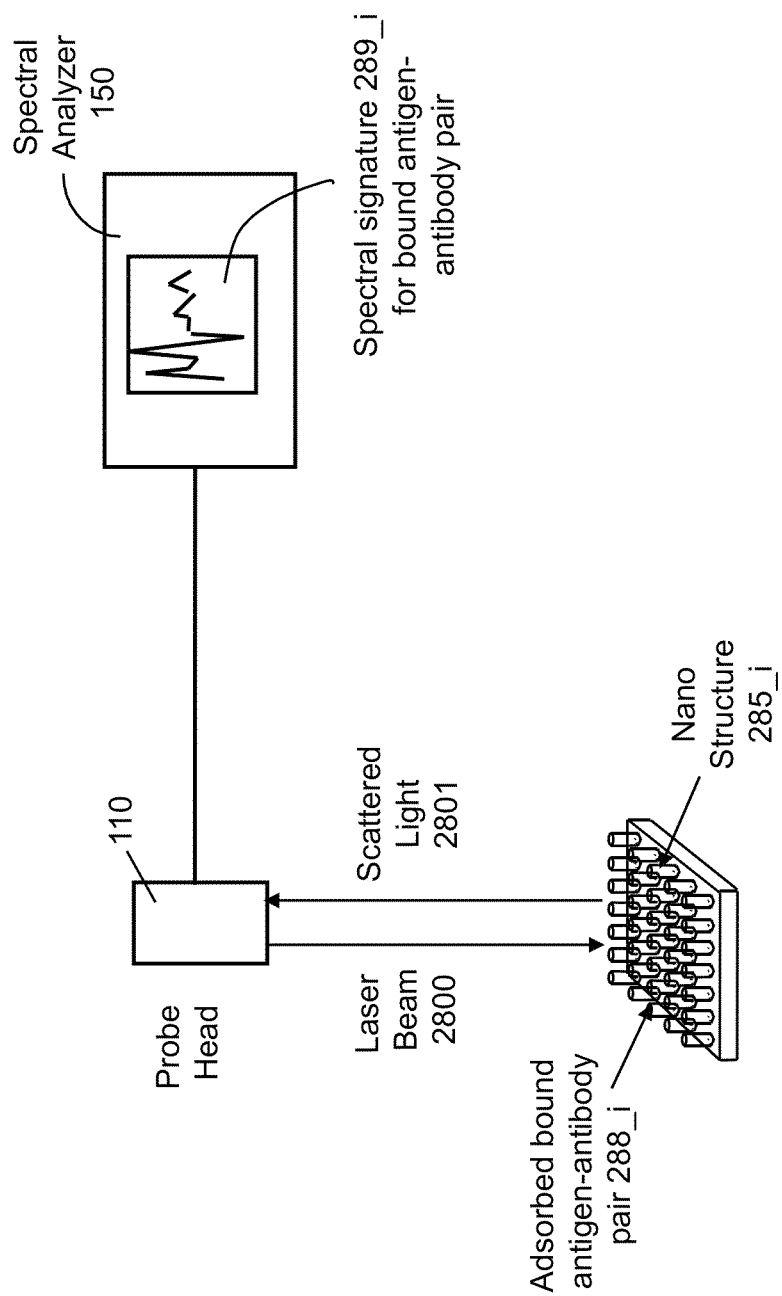
FIG. 28C shows detection of the unknown antigens bound to the antibodies adsorbed to the nano particles as described by the process in FIG. 27.

Referring to FIGS. 27 and 28C, each of the nano structures 285_1 ... 285_i, ... 285_N containing the unknown antigen 287 and adsorbed with the different antibodies 286_1 ... 286_i, ... 286_N is respectively illuminated by a laser beam 2800 (step 2750). The laser beam 2800 can be emitted by a laser device in a probe head 110. The scattered light 2801 from each of the nano structures 285_1 ... 285_i, ... 285_N can be respectively collected by the probe head 110. A nano-surface enhanced Raman spectrum is obtained from light scattered 2801 by a spectral analyzer 150 for each of the nano structures 285_1 ... 285_i, ... 285_N (step 2760).

The spectral signature for a bound antigen-antibody pair is searched in each of the Raman spectra obtained from the nano structures 285_1 ... 285_i, ... 285_N (step 2770) similar to the descriptions above in relation to FIG. 17 and the step 2570 (FIG. 25). If a spectral signature for an antigen-antibody pair 288_i (or the associated Raman marker molecule as described above) is found in the Raman spectrum obtained from one of the nano structures 285_i, the unknown antigen 287 in the reagent can be identified to be the antigen that matches the antibody 286_i adsorbed to the nano structures 285_i (step 2780). Due to the key-lock nature between antigens and antibodies, the Raman spectra obtained from other sample solutions would not exhibit spectral signatures for their respective antigen-antibody pairs. The spectral signature can be verified by obtaining nano-structure enhanced Raman scattering in a plurality of nano structures 284_i adsorbed with the antibody 286_i applied with the reagent containing the unknown antigen 287.

Moreover, the concentration level of the antigen 287 identified in the reagent can be determined using the nano-surface enhanced Raman spectrum in which the spectral signature is found (step 2790). The concentration level of the antigen 287 in the sample solution can be determined for example using the intensity, the relative intensity, or the integrated area of the spectral signature such as a spectral peak.

In some embodiments, the above described biological immunoassay using nano-structure based spectral sensing can be applied to diagnose a disease. The reagent can be extracted as a body fluid or breath from a person that is suspected having a disease. The body fluid can include blood, saliva, urine, serum, tear, sweat, stomach fluid, sperm, or a secrete body fluid. The unknown antigen in the reagent is associated with the disease of concern. The disease can be selected from the group consisting of cancer, asthma, allergy, liver cirrhosis, a failing kidney, leukemia, immunodeficiency virus (HIV), Alzheimer's disease, Parkinson disease, diabetes, smoking addiction, arthritis, a cardiovascular disease, SARS, and flu. The cancer can include different types such as lung cancer, breast, stomach cancer, ulcer cancer, ovarian cancer, uterus cancer, cervix cancer, oral cancer, esophageal cancer, thyroid cancer, larynx cancer, colon cancer, bladder cancer, prostate cancer, bronchus cancer, pancreas cancer, leukemia cancer, lymphoma cancer, thyroid cancer, myeloma cancer, larynx cancer, head cancer, neck cancer, and skin cancer.

The proximity of the unknown substance to the nano structured surface is a significant factor in determining the signal strength of the nano-surface enhanced Raman scattering. In some embodiments, the nano surface structures used in the nano surface enhanced Raman scattering are pretreated by chemicals or biological materials to assist the adsorption of the substance to be detected to the nano surface structures. The above described antibodies serve as one example for such chemicals or biological materials, which can assist the adsorption or binding of an unknown antigen to the nano structure surfaces. Another example for such chemicals or biological materials is an antigen, which can assist the adsorption or binding of an unknown antibody to the nano structure surfaces. In general, the nano structures on a substrate or the nano particles can be treated by other chemicals or biological materials to assist adsorption of the unknown substance. These chemicals or biological materials can be adsorbed to the nano surfaces, like the antibodies, or modify the binding properties on the nano surfaces to assist molecular adsorption of the unknown substance to the nano surface. The chemicals or biological materials can be selected specific to the unknown substance intended to be detected.

An advantage of the presently disclosed methods and systems is that unknown antigens can be detected and identified at extremely high sensitivity. The enhancement of Raman spectral analysis by nano surface structures can significantly lower the detectable concentration level required for antigen identification in biological immunoassay.

In some embodiments, the disclosed systems and methods is compatible with multiplex labeled-immunoassay. Reporter molecules such as thiophenol, bipyridine derivatives, and cyanopyridine derivatives are attached to different immune-gold colloid particles. A labeled colloid and an antigen are covalently bound to sensor substrates specifically coated with different antibodies. After washing off the solvent, surface enhanced Raman scattering is conducted to detect the reporter molecules. The presence of the Raman signatures of the reporter molecules off a specific antibody substrate can indicate binding of specific antibody-antigen pair at the surface of the substrate, thereby identifying the antigen.

In some embodiments, a sandwich structure can include antibodies absorbed to a substrate and an unknown antigen bound to the antibody on the substrate. Colloidal particles having bound antibody and label molecules are further bound to the antigen by anti-boy/antigen binding to form the sandwich structure. The label molecules have specific Raman signatures that can be easily identified by surface enhanced Raman scattering from the sandwich structure.

Sandwich methods are usually used for the detection of large molecules. Small molecule compounds are known to bind only with one antibody, and therefore cannot be detected by sandwich structure. In the present invention, competition testing methods (instead of the sandwich methods) are used to detect the small molecule compounds.

Figure 29:
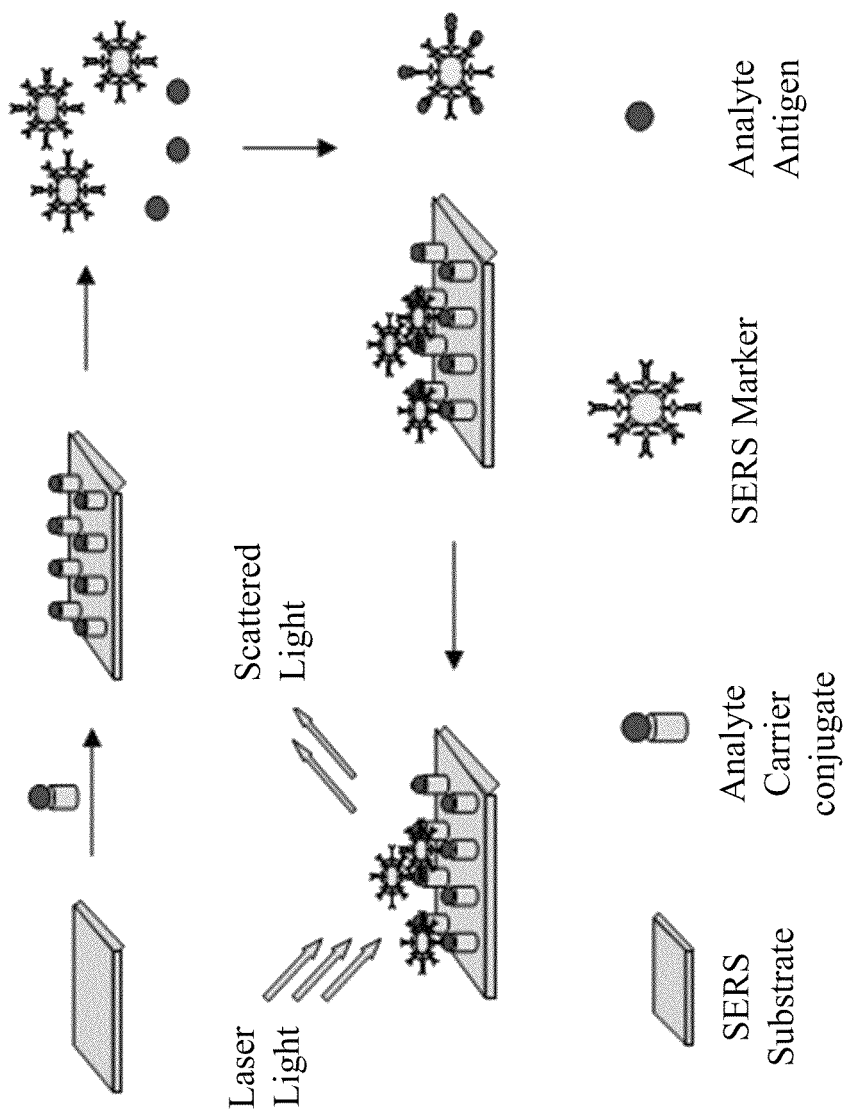
FIG. 29 shows the process of competitive determination of small molecule compounds using immunoassay utilizing nano-structure based spectral sensing in accordance to the present invention.

There are a lot of small molecular compounds such as veterinary drugs, microtoxins, pesticides, PCBs, PAHs, and even heavy metals, etc. observed in food, environmental, pharmaceutical and biological samples. Competitive SERS immunoassay (SERSIA) determination of small molecule compounds and the principle of the process are shown in FIG. 29. First, the coating antigen (i.e. analyte-carrier protein conjugate) is fixed to the SERS substrate by adsorption or cross-linking to form solid-phase antigen. The solid-phase antigen and the tested antigen in standard or sample solution compete for the limited antibodies in the SERS marker (the nanoparticles on which both SERS actives and antibody are immobilized). After the substrate is washed, laser light is directed to illuminate the sample substrate and scattered light is collected to produce Raman spectra. The strength of the SERS signal is inversely proportional to the amount of antigen with the test.

Two studies have been conducted: flat solid-phase antigen SERSIA, and liquid solid-phase antigen SERSIA based on nanoparticles.

The process involves preparation and characterization of solid-phase antigen, including SERS substrate selection and assessment; preparation of coating antigen; immobilization of coating antigen on the substrate; characterization of the solid-phase antigen; selecting the blocking conditions to reduce non-specific adsorption.

Preparation and characterization of SERS marker include preparation and characterization of colloidal gold nanoparticles; cross-linked form of SERS active material and colloidal gold nanoparticles; cross-linked form of antibody and colloidal gold nanoparticles; SERS marker characterization.

The conditions to be optimized for the detection of small molecule compounds by competitively SERSIA includes: the selection of solid-phase antigen and the amount of SERS marker; the selection of temperature, humidity and time for immuno-reaction; the choice of buffer liquid composition, concentration, ionic strength and pH; the selection of washing liquid composition, concentration, ionic strength and pH.

Condition selection of SERS signal determination includes the choice of a variety of testing conditions for portable surface-enhanced Raman stimulated spectroscopy; collecting SERS signal from SERS substrate to determine.

Characterization of SERSIA method includes establishing standard curve to determine the sensitivity of SERSIA; cross-reaction experiments to determine the specification of SERSIA; the spiked sample experiments to determine the accuracy and precision of SERSIA; the stability experiments to determine the stability of SERSIA.

Analysis of real samples includes collection, pretreatment, target separation, extraction; taking SERSIA to measure the real samples, in order to determine recovery rate.

Nano-Structure Based Chromatography and Spectral Sensing in Biological Immunoassay In some embodiments, the above disclosed nano-structured based light scattering probe and substance detection methods are applicable to an integrated chromatography-immunoassay system.

Referring to FIG. 30A-31B, an integrated chromatography-immunoassay system 3100 includes a base 3110, a chromatographic pad 3120, a test membrane 3130, and an absorption pad 3140. Coating antigens 3150 are coated along a test line 3155 on the test membrane 3130. Examples of antigens include clenbuterol, nitrofurans, organic phosphorus, organochlorine, pro terephthalate, a pesticide, a rodenticide, a substance in a veterinary drug, microtoxin, PCBs, PAHs, etc.

Figure 33:
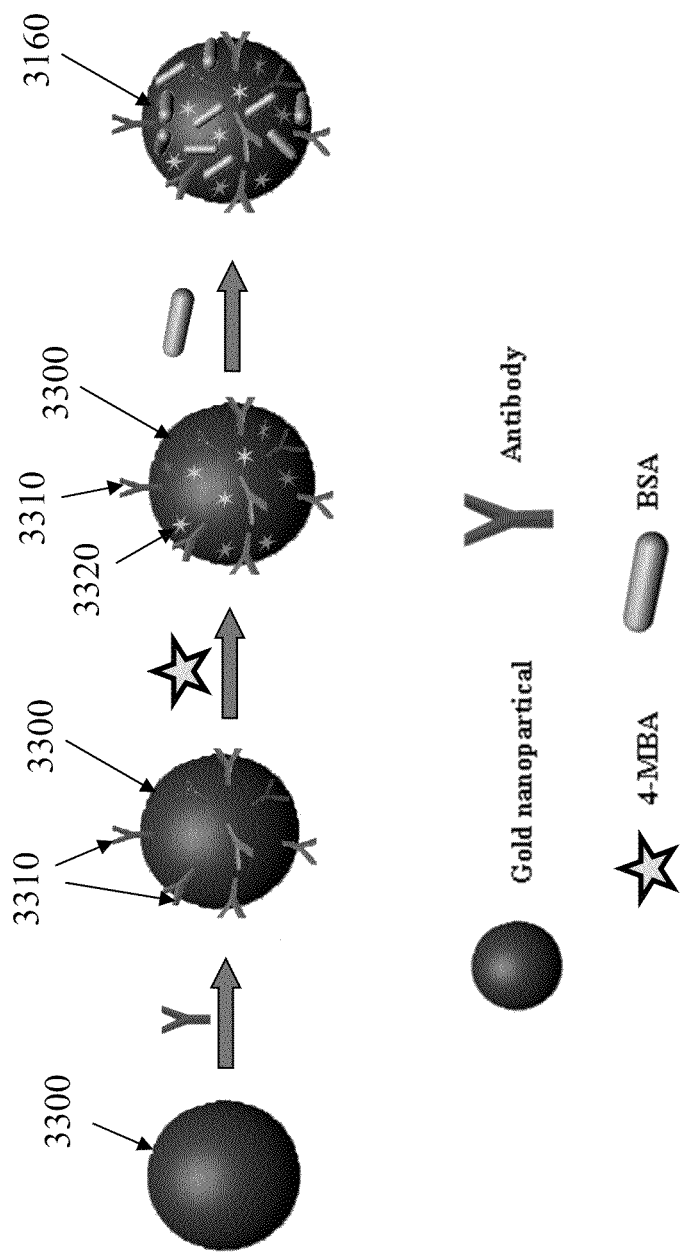
FIG. 33 illustrates preparation of nano-structured probes suitable for the integrated chromatography-immunoassay system.

Referring to FIGS. 30A and 30B, labeled nano-structured probes 3160 and competitive antigens 3170 are introduced onto the chromatographic pad 3120. As shown in FIG. 33, the labeled nano-structured probes 3160 are prepared by immobilizing Raman marker 4-MBA and antibody 3310 on the surfaces of nano particles 3300. The labeled nano-structured probes 3160 were in the form of MBA-nanoparticles-Ab conjugate, which were then treated with bovine serum albumin (BSA), a blocking protein to eliminate the nonspecific binding sites on the nano particles. Materials suitable for the nano particles can include colloidal Au, colloidal Ag, Au—Ag alloy, Au nano rods, hollow Au nano spheres, etc.

Referring to FIGS. 30B-31B, the labeled nano-structured probes 3160 and the competitive antigens 3170 placed on the chromatographic pad 3120 diffuse toward and then into the test membrane 3130. If there is no competitive antigen in the standard or sample solution, the antibodies carried on the labeled nano-structured probes 3160 will be mostly captured by the coating antigen 3150 fixed to the test membrane 3130 at the test line 3155. In contrast, for standard or sample solution containing analyte, the binding sites on the specific antibody molecules are occupied firstly by analyte, leaving fewer binding sites for coating antigen 3150. Consequently, less labeled nano-structured probes will remain at the test line 3155 near the coating antigens 3150. Thus, the concentration of the labeled nano-structured probes 3160 at the test line 3155 is inversely related to the concentration of competitive antigen 3170.

FIG. 32 illustrates symbols of nano-structured probe and exemplified antigen and coating antigen used in FIGS. 30A-31B.

Figure 34:
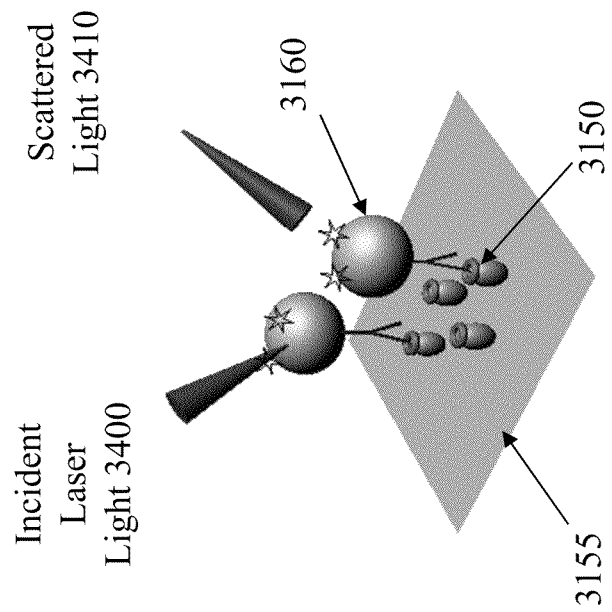
FIG. 34 shows a detailed view of light scattering off the nano-structured probes applied in the integrated chromatography-immunoassay system.

After the labeled nano-structured probes 3160 bind with the coating antigen 3150 coated on the membrane 3130 at the test line 3155, referring to FIG. 34, a laser light 3400 is directed to illuminate the labeled nano-structured probes 3160 bound to the coating antigen 3150 along the test line 3155. Scattered light 3410 is collected and analyzed using the systems and methods as described above for nano-structured based Raman scattering substance detection.

Figure 35:
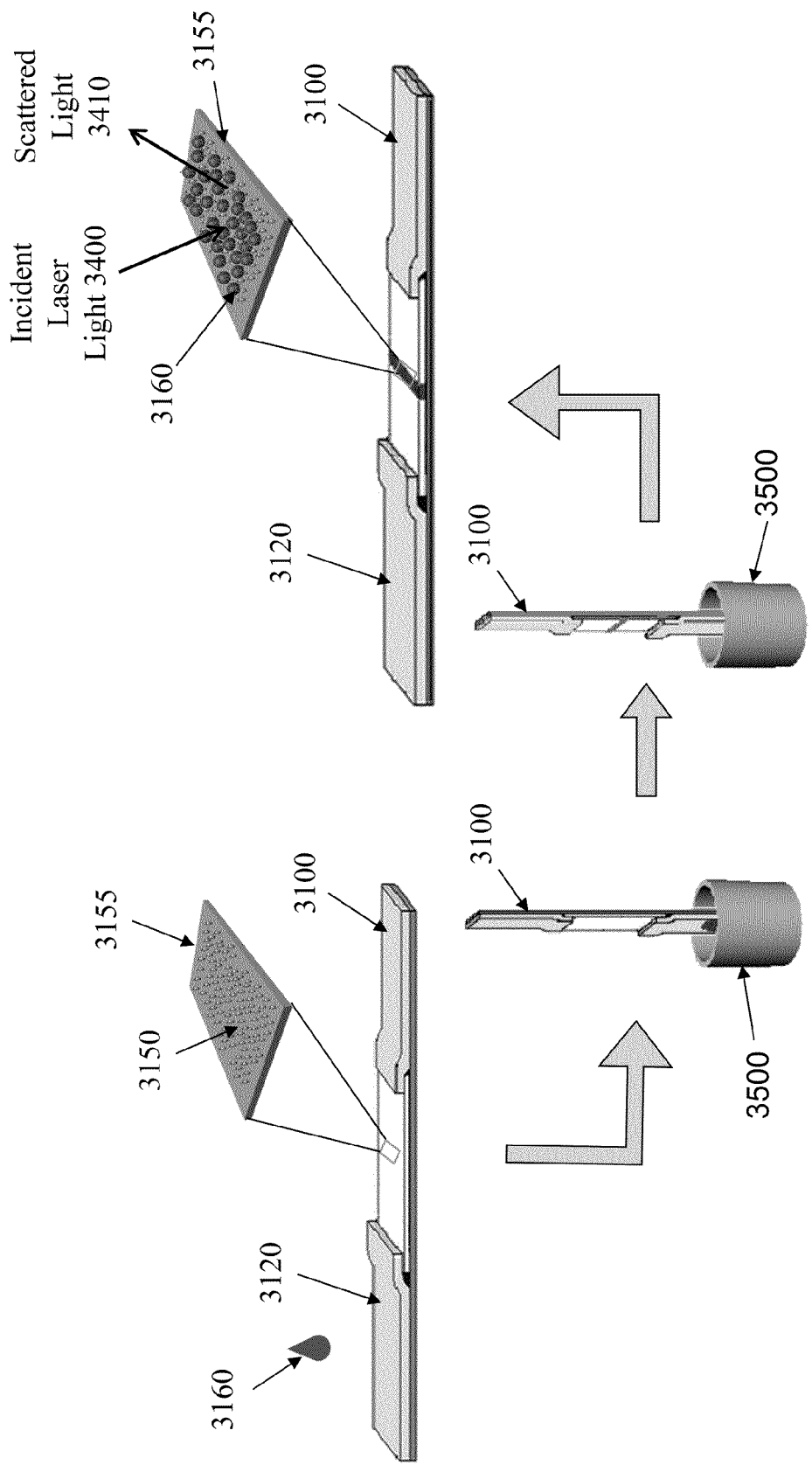
FIG. 35 illustrate operation steps of nano-structured based light scattering and substance detection using the integrated chromatography-immunoassay system shown in FIGS. 30A-31B.

FIG. 35 illustrate operation steps of nano-structured based light scattering and substance detection using the disclosed integrated chromatography-immunoassay system. An integrated chromatography-immunoassay system 3100 is provided (as shown in FIG. 31A). Labeled nano-structured probes 3160 are introduced onto the chromatographic pad 3120 (as shown in FIG. 31B). The chromatographic pad 3120 of the integrated chromatography-immunoassay system 3100 is then dipped into a plastic well 3500 containing the solution of the competitive antigen 3170 to draw the competitive antigens 3170 into the chromatographic pad 3120. The labeled nano-structured probes 3160 and the competitive antigens 3170 placed on the chromatographic pad 3120 diffuse toward and then into the test membrane 3130. If the concentration of competitive antigen in the plastic well 3500 is zero, most antibodies carried on the labeled nano-structured probes 3160 would be captured by the coating antigen 3150 at the test line 3155; On the other hand, higher concentration of the competitive antigen in the plastic well 3500 will make the lesser of the labeled nano-structured probe be captured on the test membrane 3130 at the test line 3155. The labeled nano-structured probes 3160 bound to the coating antigen 3150 along the test line 3155 is illuminated by a laser light 3400. The scattered light 3410 is collected and analyzed using the systems and methods as described above for nano-structured based Raman scattering substance detection and described in detail below.

Figure 36:
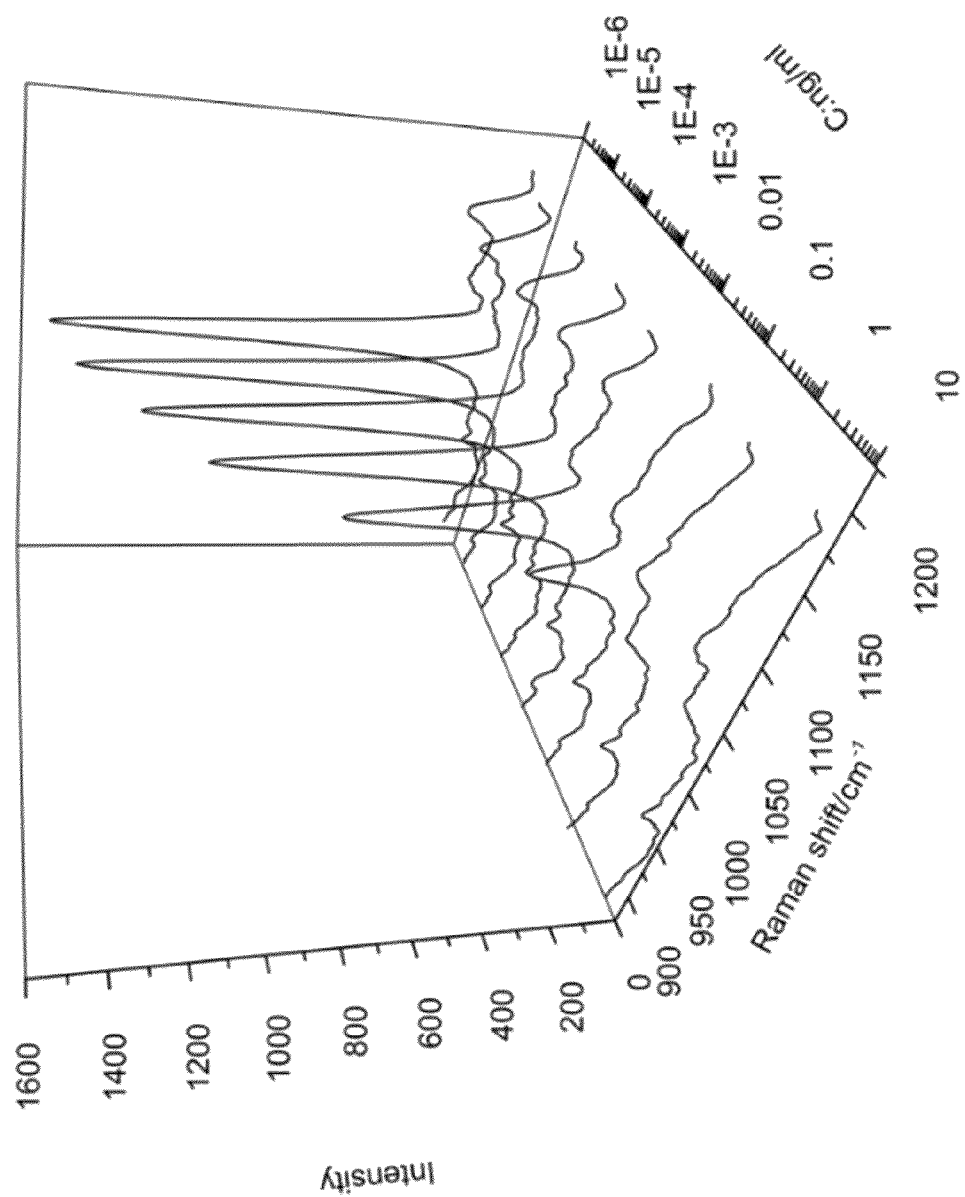
FIG. 36 shows Raman scattering intensities as a function of competitive-antigen concentration in the integrated chromatography-immunoassay system.

FIG. 36 shows a Raman scattering intensities obtained from the integrated chromatography-immunoassay system 3100 at competitive antigen concentrations ranging from 10 to $10^{-6}$ ng/ml. The Raman scattering intensities show speaks at 1074 $cm^{-1}$ (the Raman signature for MBA), which decreases as the clenbuterol concentration (C in ng/ml) increases because the competitive antigen compete with test antigens for limited antibody binding sites on the labeled nano-structured probes. The higher concentration of the competitive antigen in the plastic well 3500, the less labeled nano-structured probes 3160 are to be captured on the test line 3155.

Figure 38:
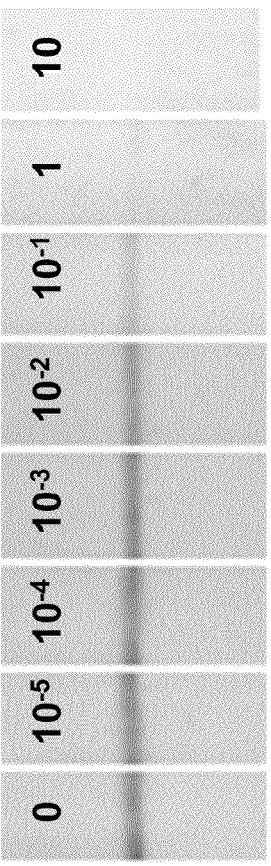
FIG. 38 shows photographs of a test line in a test membrane obtained by the integrated chromatography-immunoassay system.
Figure 37:
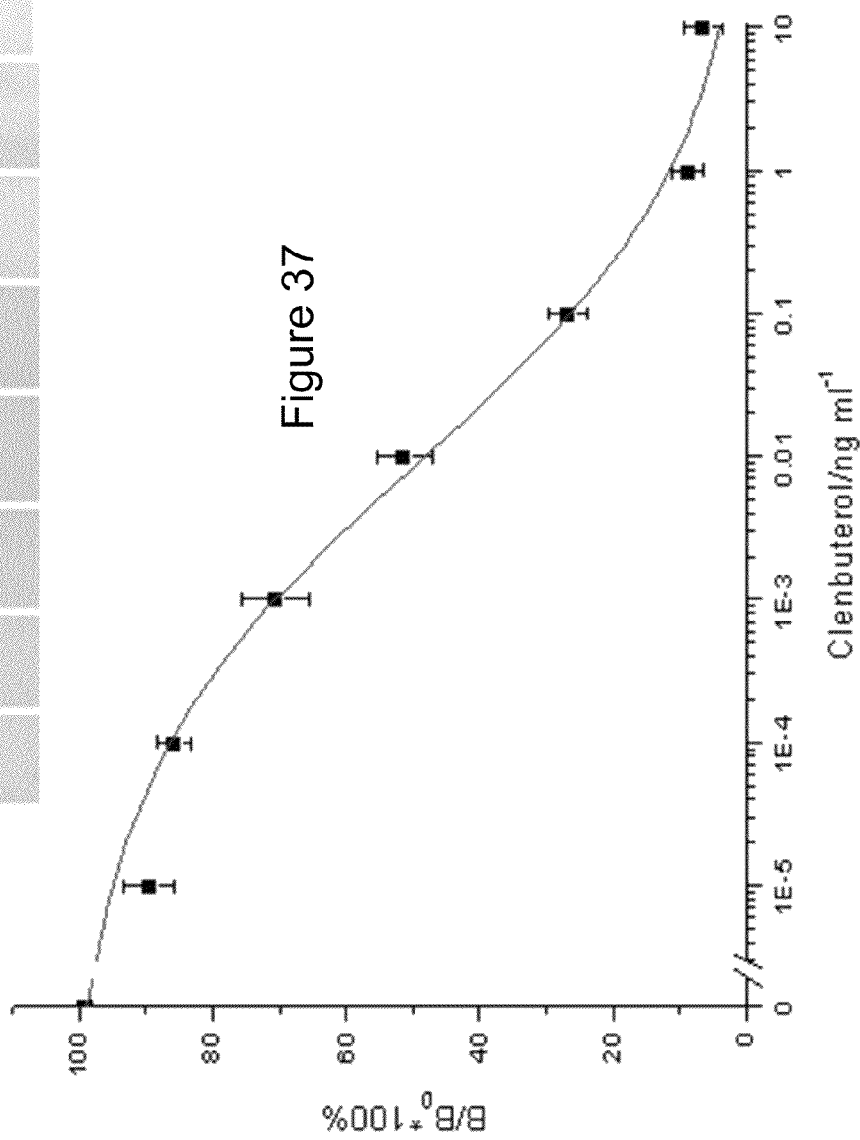
FIG. 37 shows a standard Raman scattering curve by the integrated chromatography-immunoassay system.

FIG. 37 shows a standard curve for target analyte, i.e. the peak Raman scattering intensities at 1074 $cm^{-1}$ as a function of the competitive antigen (e.g. clenbuterol) concentration after the baseline correction. $B_0$ is the Raman scattering signal intensity at zero competitive-antigen concentration. B is the Raman scattering signal intensity at other concentrations. Similar to FIG. 36, the peak intensity decreases as a function of the competitive antigen concentration. FIG. 38 shows photographs of the test line area in the test membranes at different clenbuterol concentrations.

Figure 39:
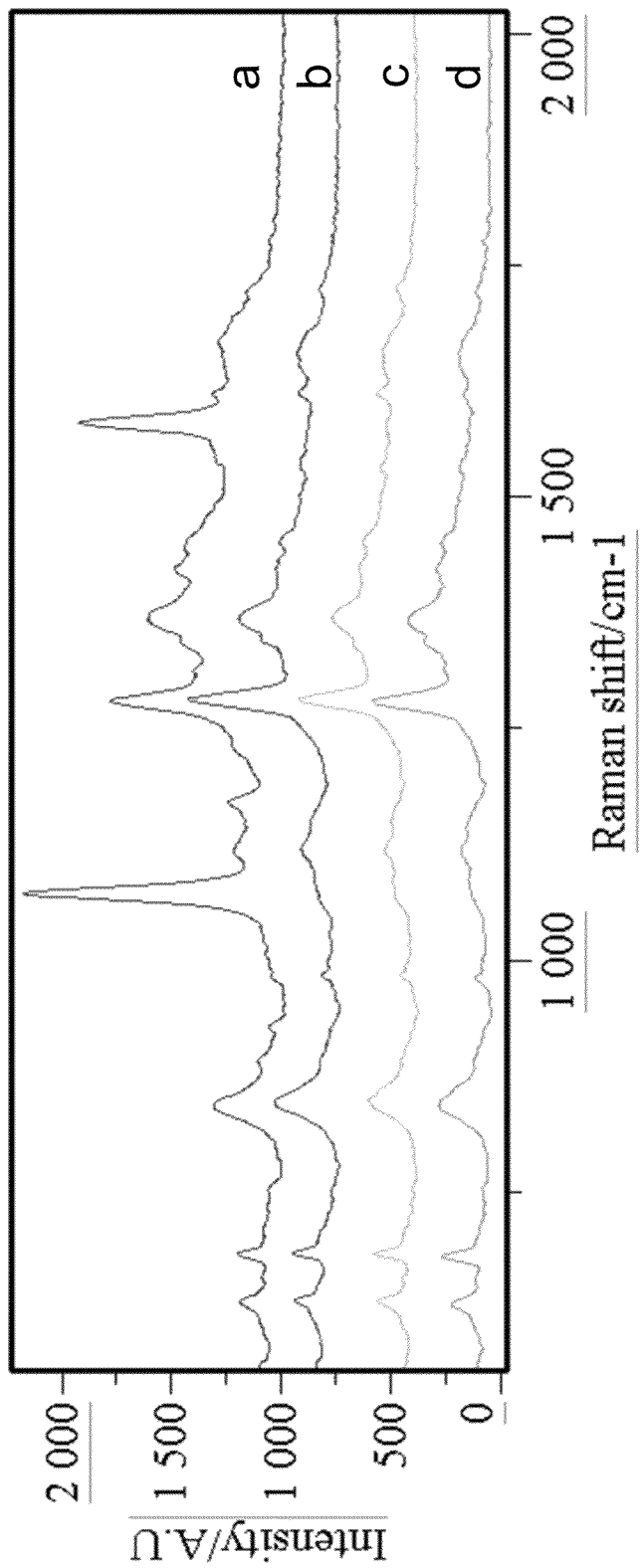
FIG. 39 illustrates Raman scattering spectra at different preparation conditions.

FIG. 39 illustrates Raman spectra at different preparation conditions: a) with MBA labeled immunoGNPs and control experiment; b) immunoGNP without MBA; c) MBA labeled GNPs without Antibody; and d) NC membrane without any treatment. It is observed that the peak Raman intensity values at 1074 $cm^{-1}$ only existed with MBA labeled nano-structured probes. The spectral peak is absent at 1074 $cm^{-1}$ without MBA labeling or antibody binding. FIG. 39 clearly demonstrates that the observed SERS signal is only came from the Raman marker MBA which, together with antibody, were immobilized on the labeled nano-structured probes and captured by the coating antigen 3150 on the test line 3155.

Figure 40:
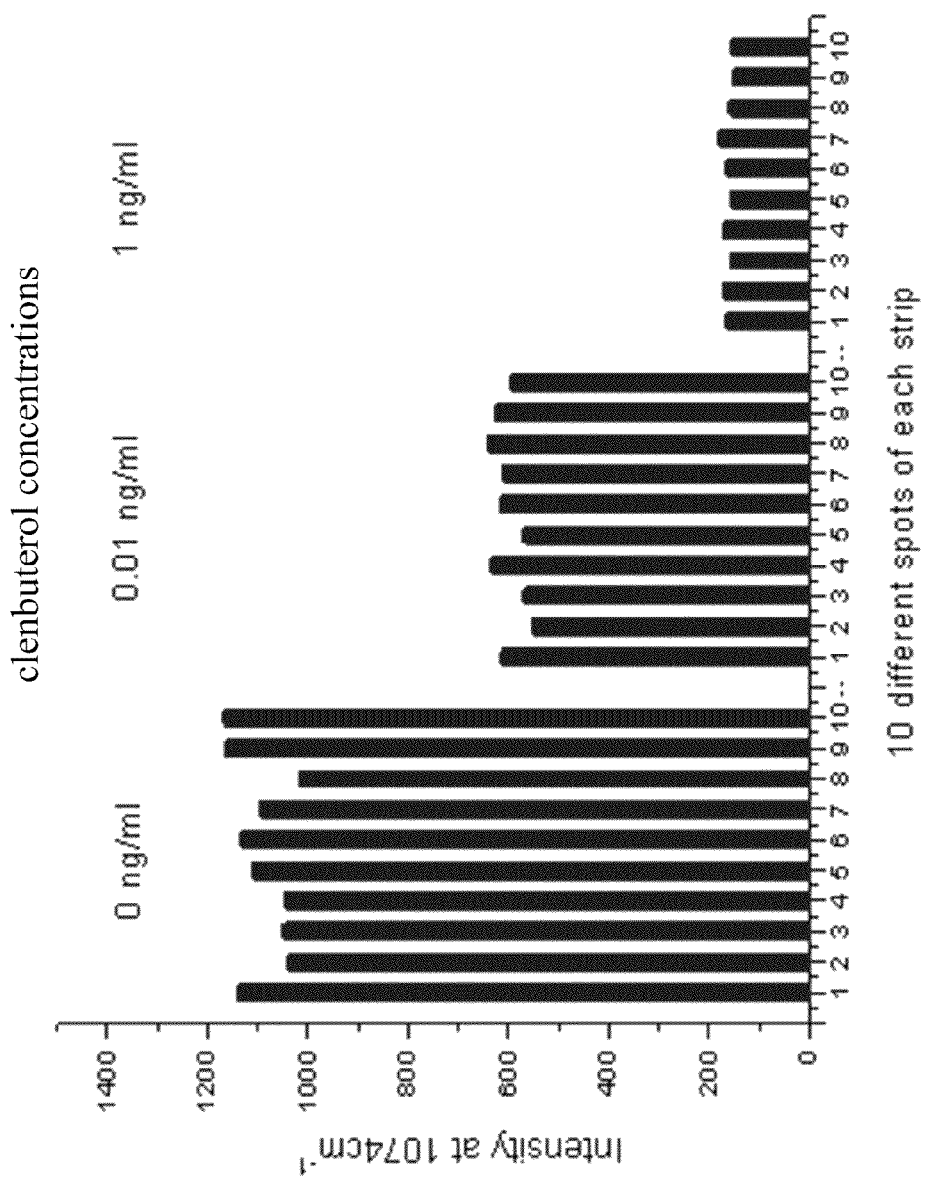
FIG. 40 shows repeatability in peak Raman scattering intensities obtained from ten different points along the middle of the test lines by the integrated chromatography-immunoassay system.

FIG. 40 shows repeatability in peak Raman scattering intensities by the integrated chromatography-immunoassay system. Raman peak intensities are measured at ten sampling areas along a test line 3155 (FIGS. 30A-31B) at each of clenbuterol concentrations of 0, 0.01 and 1 ng/ml. The standard deviation is between 5.0%-5.6%, indicating high detection repeatability by the disclosed integrated chromatography-immunoassay system.

Figure 41:
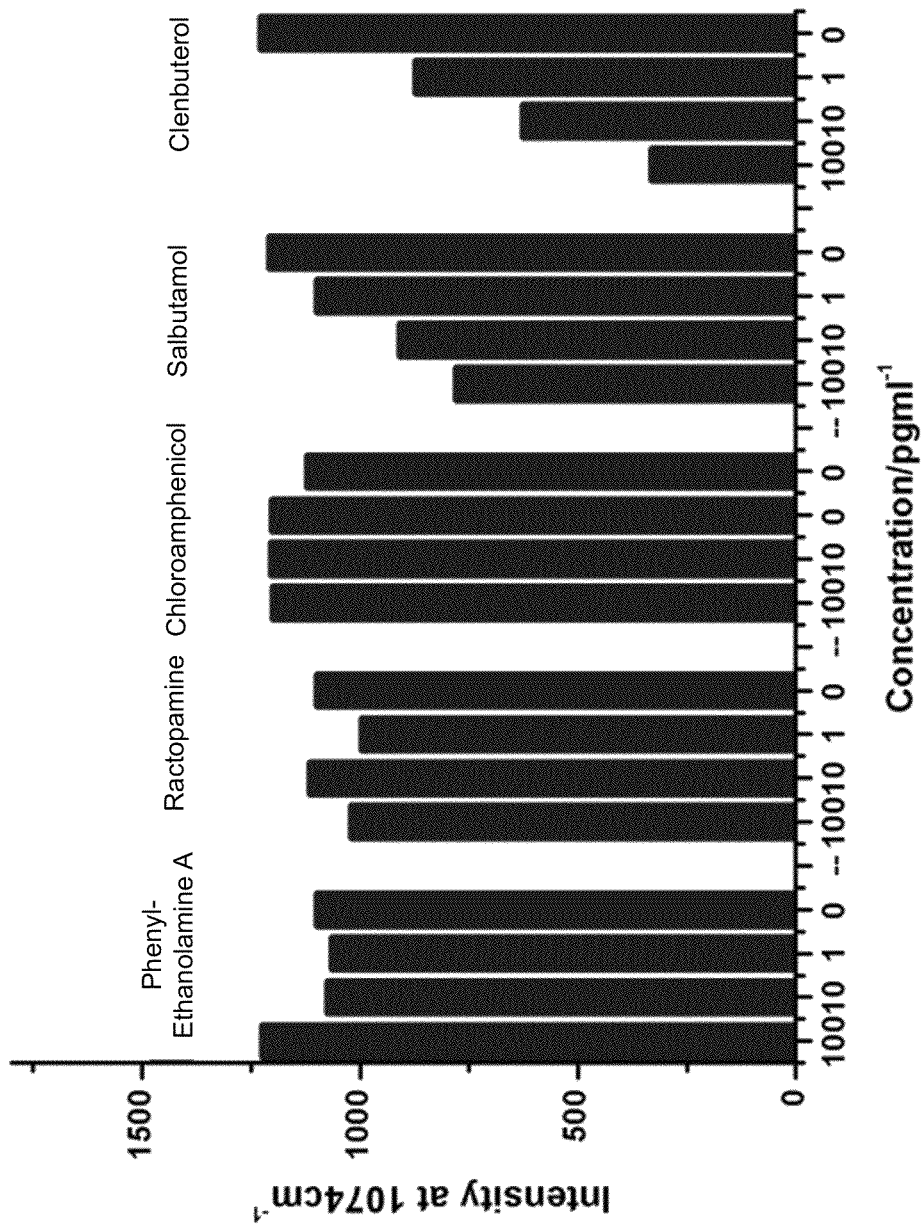
FIG. 41 shows specificity of the integrated chromatography-immunoassay system.

FIG. 41 shows specificity of the Raman scattering signals in the integrated chromatography-immunoassay system under different preparation conditions. It was observed that there was almost no cross reactivity with phenylethanolamine A, ractopamine, and chloroamphenicol due to the fact that when they are used as competitive antigens at the concentration 1.0, 10 and 100 pg/mL, the SERS intensity are almost constant. The competition suppression is only apparent in salbutamol and clenbuterol, with latter more effective than the former.

Antigens suitable for the integrated chromatography-immunoassay system and related methods include various small molecular compounds such as clenbuterol, nitrofurans, organic phosphorus, organochlorine, pro terephthalate, a pesticide, a rodenticide and a substance in a veterinary drug provided that the corresponding antibodies are available.

Other examples for the antigen include melamine, sodium cyclamate, sodium cyclohexylsulfamate, cane sugar, starch, nitrite, nitrate, Sudan I, II, III and IV, malachite green, methomidophos, acephate, DDT, DDV, malathion, fenitrothion, deltamethrin, cypermethrin, methyl parathion, phosmet, phorate, dimethoate, nitrofuran, furanzolidole, chloramphenicol, chlortetracycline, chloromycetin, ciprofloxacin, enorfloxacin, AOZ, heavy metal, lead (Pb), cadmium (Cd), mercury (Hg), chromium (Cr), ractopamine, salbutamol, penicillin, bisphenol A, DEHP, 6-benzylaminopurine, or olaquindox, which can include regulated substances in food products.

Ketamine can be chemically modified to produce p-NH2-Ketamine, which allows them to bind to a protein carrier such as Hemocyanin (KLH), Bovine serum albumin (BSA), Ovalbumin, and γ-Globulin etc. These protein carriers bound with Ketamine have antigen functions and can trigger immunological reactions and production of antibodies in human or animal bodies, which are suitable for test antigen in the disclosed system and methods.

It should be noted that the above described systems and methods can be compatible with other variations without deviating from the spirit of the present invention. The systems and methods are compatible with competitive immunoassays and noncompetitive immunoassays (i.e. sandwich assay). In the noncompetitive immunoassays, the unknown antigen is bound to the antibody site on the sensor substrate. Then labeled antibody is bound to the antigen to form a "sandwich" structure. Surface enhanced Raman scattering is conducted on the sandwich structure to detect enhanced spectral signature of the antibody/antigen pair, thus identifying the unknown antigen.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention. For example, the identification of "bad oils" and "good oil" can be made at Raman shift adjacent to or different from those spectral signatures described above.

What is claimed is:

1. A method for identifying an antibody using an integrated chromatography-immunoassay system, comprising:
   receiving, by a chromatographic unit, labeled nano-structured probes comprising nano particles, and Raman markers and antibodies attached to the nano particles;
   allowing the labeled nano-structured probes comprising the nano particles and the associated Raman markers and the antibodies to diffuse through a test membrane comprising coating antigens;
   allowing the antibodies on the associated nano particles with the associated Raman markers to bind to the coating antigens on the test membrane;
   illuminating the labeled nano-structured probes having the Raman markers, and the antibodies bound to the coating antigens on the test membrane by a laser light;
   obtaining a Raman spectrum from light scattered with a spectral analyzer from the labeled nano-structured probes having the antibodies bound to the coating antigens on the test membrane; and
   identifying a spectral signature related to the Raman markers in the Raman spectrum associated with the antibody-antigen pair, which enables detection and identification of at least one of the antibodies attached to the nano particles.

2. The method of claim 1, further comprising:
   receiving a competitive antigen by the chromatographic unit; and
   allowing the competitive antigen to diffuse through the test membrane, wherein the competitive antigen is configured to compete with the coating antigens to bind to the antibodies on the nano particles.

3. The method of claim 1, wherein the Raman markers in the labeled nano-structured probes are attached to the nano particles or the antibodies.

4. The method of claim 1, wherein the antigen is selected from a group consisting of clenbuterol, nitrofurans, organic phosphorus, organochlorine, pro terephthalate, a pesticide, a rodenticide, and a veterinary drug.

5. The method of claim 1, wherein the antigen is selected from a group consisting of melamine, sodium cyclamate, sodium cyclohexylsulfamate, cane sugar, starch, Sudan I, II, III and IV, malachite green, methomidophos, acephate, DDT, DDV, malathion, fenitrothion, deltamethrin, cypermethrin, methyl parathion, phosmet, dimethoate, nitrofuran, furanzolidole, chloramphenicol, chlortetracycline, ciprofloxacin, clenbuterol, and enorfloxacin.

6. The method of claim 1, wherein the nano particles have an average diameter in a range from 10 nm and 100 nm.

7. The method of claim 1, wherein the nano particles is selected from a group consisting of a material selected from a group consisting of a metal, a metal alloy, an oxide material, silicon, a polymeric material, a magnetic or ferromagnetic material, and a combination thereof, or comprises a material selected from a group consisting of Al, Ag, Au, Cu, Fe, Co, Ni, Cr, Zn, Sn, Pd, Pt, and a combination thereof.

8. The method of claim 1, wherein the coating antigens comprise clenbuterol, wherein the clenbuterol is bound to an OVA molecule to form an Ovalbumin-clenbuterol complex, the OVA-clenbuterol complex bound to the test membrane.

9. The method of claim 1, further comprising:
allowing a competitive antigen at a plurality of concentrations to diffuse through the test membrane; and
measuring intensities of the spectral signature related to the Raman markers in the Raman spectrum associated with the antibody-antigen pair at the plurality of concentrations of the competitive antigen to identify at least one of the antibodies attached to the nano particles.

10. The method of claim 1, further comprising:
identifying one of the coating antigens that matches at least one of the antibodies on the nano particles based on the spectral signature related to the Raman markers.

11. The method of claim 1, further comprising:
diagnosing a disease in the person based on the identification of the one of the coating antigens associated with the disease.

12. The method of claim 11, wherein the reagent comprises a body fluid obtained from a person.

13. The method of claim 11, wherein the disease is selected from the group consisting of a cancer, asthma, allergy, liver cirrhosis, a failing kidney, leukemia, Alzheimer's disease, Parkinson disease, diabetes, smoking addiction, arthritis, a cardiovascular disease, SARS, a flu, and human immunodeficiency virus (HIV).

* * * * *